US007745188B2

(12) United States Patent
Woodgate et al.

(10) Patent No.: US 7,745,188 B2
(45) Date of Patent: Jun. 29, 2010

(54) THERMOSTABLE Y-FAMILY POLYMERASES AND CHIMERAS

(75) Inventors: Roger Woodgate, Rockville, MD (US); John P. McDonald, Germantown, MD (US); Wei Yang, Silver Spring, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 634 days.

(21) Appl. No.: 11/596,783

(22) PCT Filed: May 20, 2005

(86) PCT No.: PCT/US2005/017941

§ 371 (c)(1),
(2), (4) Date: Nov. 17, 2006

(87) PCT Pub. No.: WO2005/113760

PCT Pub. Date: Dec. 1, 2005

(65) Prior Publication Data

US 2008/0193925 A1 Aug. 14, 2008

Related U.S. Application Data

(60) Provisional application No. 60/573,684, filed on May 20, 2004, provisional application No. 60/623,490, filed on Oct. 29, 2004.

(51) Int. Cl.
| | |
|---|---|
| *C12N 9/12* | (2006.01) |
| *C12N 9/10* | (2006.01) |
| *C07K 14/00* | (2006.01) |
| *C12Q 1/48* | (2006.01) |
| *C12Q 1/68* | (2006.01) |
| *C12N 15/00* | (2006.01) |
| *C12N 5/10* | (2006.01) |
| *C12N 1/21* | (2006.01) |
| *C12P 21/00* | (2006.01) |
| *C07H 21/00* | (2006.01) |

(52) U.S. Cl. .................. 435/194; 435/193; 435/15; 435/6; 435/320.1; 435/252.3; 435/325; 435/69.1; 530/350; 536/23.2

(58) Field of Classification Search .................. 435/193, 435/194, 69.1, 320.1, 15; 530/350; 536/23.2
See application file for complete search history.

(56) References Cited

U.S. PATENT DOCUMENTS

2005/0196392 A1  9/2005  Andersen
2006/0177867 A1  8/2006  Evans et al.

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Barnes et al., "PCR amplification of up to 35-kb DNA with high fidelity and high yield from λ bacteriophage templates," *Proc. Natl. Acad. Sci.* 91:2216-2220, Mar. 1994.
Bebenek and Kunkel, "Family growth: the eukaryotic DNA polymerase revolution," *CMLS, Cell, Mol. Life Sci.* 59:54-57, 2002.
Boudsocq et al., "Investigating the role of the little finger domain of Y-family DNA polymerases in low-fidelity synthesis and translesion replication," *JBC Papers in Press*, Manuscript M405249200, May 21, 2004.
Boudsocq et al., "*Sulfolobus solfataricus* P2 DNA polymerase IV (Dpo4): an archaeal DinB-like DNA polymerase with lesion-bypass properties akin to eukaryotic polη," *Nucleic Acids Research* 29(22):4607-4616, 2001.
Friedberg et al., "Error-Prone DNA Polymerases: Novel Structures and the Benefits of Infidelity," *Cell* 107:9-12, Oct. 5, 2001.
Friedberg et al., "Specialized DNA Polymerases, Cellular Survival, and the Genesis of Mutations," *Science* 296:1627-1630, May 31, 2002.
Goodman and Tippin, "Sloppier copier DNA polymerases involved in genome repair," *Curr. Opin. in Genetics and Development* 10:162-168, 2000.
Goodman and Tippin, "The Expanding Polymerase Universe," *Molecular Cell Biology* 1:101-109, Nov. 2000.
Grúz et al., "Processing of DNA lesions by archaeal DNA polymerases from *Sulfolobus solfataricus*," *Nucleic Acids Research* 31(14):4024-4030, 2003.
Johnson et al., "Deoxynucleotide Triphosphate Binding Mode Conserved in Y Family DNA Polymerases," *Molecular and Cellular Biology* 23(8):3008-3012, Apr. 2003.
Kokoska et al., "Low Fidelity DNA Synthesis by a Y Family DNA Polymerase Due to Misalignment in the Active Site," *J. Biological Chemistry* 277(22):19633-19638, 2002.
Kulaeva et al., "Indentification of a DinB / UmuC homolog in the archeon *Sulfolobus solfataricus*," *Mutation Research* 357:245-253, 1996.
Kusunoki et al., "Triptolide, an active compound identified in a traditional Chinese herb, induces apoptosis of rheumatoid synovial fibroblasts," *BMC Pharmacology* 4:2.
Ling et al., "Crystal Structure of a Y-Family DNA Polymerase in Action: A Mechanism for Error-Prone and Lesion-Bypass Replication," *Cell* 107:91-102, Oct. 5, 2001.
Ling et al., Snapshots of Replication through an Abasic Lesion: Structural Basis for Base Substitutions and Frameshifts, *Molecular Cell* 13:751-762, Mar. 12, 2004.
Masutani et al., "The *XPV* (xeroderma pigmentosum variant) gene encodes human DNA polyermase η," *Nature* 399:700-704, Jun. 17, 1999.
McDonald et al., "Novel thermostable Y-family polymerases: applications for the PCR amplification of damaged or ancient DNAs," *Nature Biotechnology, Letter*, Jul. 15, 2005.

(Continued)

*Primary Examiner*—Delia M Ramirez
(74) *Attorney, Agent, or Firm*—Klarquist Sparkman, LLP

(57) ABSTRACT

The present disclosure is related to thermostable Y-family polymerases, in particular several novel Y-family polymerases and chimeras made therefrom, as well as methods of identifying other Y-family polymerases, methods of generating other chimeric Y-family polymerases, methods of amplifying ancient or damaged DNA, and methods of incorporating fluorescent or modified nucleotides into a DNA molecule.

8 Claims, 18 Drawing Sheets

OTHER PUBLICATIONS

McKenzie et al., "SOS Mutator DNA Polymerase IV Functions in Adaptive Mutation and Not Adaptive Amplification," *Molecular Cell* 7:571-579, Mar. 2001.

Ohmori et al., "The Y-Family of DNA Polymerases," *Molecular Cell* 8:7-8, Jul. 2001.

Pavlov et al., "Recent developments in the optimization of thermostable DNA polymerases for efficient applications," *Trends in Biotechnology* 22(5):253-260, May 2004.

Rossi et al., "Extremophiles 2002," *J. Bacteriology* 185(13):3683-3689, Jul. 2003.

She et al., "The complete genome of the crenarcheon *Sulfolobus solfataricus* P2," *Cell Biology* 98(14):7835-7840, Jul. 3, 2001.

Tompkins et al., Error-Prone Polymerase, DNA Polymerase IV, is Responsible for Transient Hypermutation during Adaptive Mutation in *Escherichia coli, J. Bacteriology* 185(11):3469-3472, Jun. 2003.

Wang et al., "A novel strategy to engineer DNA polymerases for enhanced processivity and improved performance in vitro," *Nucleic Acids Research* 32(3):1197-1207, 2004.

Yang, "Damage repair DNA polymerase Y," *Current Opinion in Structural Biology* 13:23-30, 2003.

Yang et al., A novel strategy to engineer DNA polymerases for enhanced processivity and improved performance in vitro.

Yeiser et al., "SOS-induced DNA polymerases enhance long-term survival and evolutionary fitness," *PNAS* 99(13):8737-8741, Jun. 25, 2002.

\* cited by examiner

```
        M K P I H L S V G R F N I D I I V K I X K I P D I D E F X T   Majority
                  10              20              30
1     [   ] L [       ] G [ I ] [   ] A [   ] N [   P D L D E ] E [ ]  Sa_ribo
1     [ - - ] A [         ]         L D S [ L ] P [   ] S S H M        Ss_ribo
1     [                 ] N [ E ]  M [   ] T [       ] L [ ]           St_ribo T D X L E I M P G G A A V N Y A V A I T K L G H S X K L L A   Majority
                  40              50              60
31    [   ] T [   ] L [ G ] A [     ] A [   ] I [ ] N [ F G ] [ I ] I [ ] S   Sa_ribo
29    [   ] V [         ] G [   ] T [       ] V [   L ] A [       ]           Ss_ribo
31    [   ] L M [                                           ] S [         ]   St_ribo K V G K X X X V X S L M E X I A E M G V L D Y V E E T N X   Majority
                  70              80              90
61    [ K I G ] D S L [ ] S Y V L [ ] R [           G V G L D Y V E E ] [ ] L   Sa_ribo
59    [       ] S E V [ ] R [   ] K V V [ L         E V   L ] E                Ss_ribo
61    [       ] N T I T Q [     ] S [                             ] A          St_ribo P Q S M A L I F L R X N G X I S M V R K L G A S I L L T X E   Majority
                  100             110             120
91    [             ] R [     ] D [     ] S [           G S   L ] D K [ ]     Sa_ribo
89    K P [ ] A T [         ] N D [ ] T L [     R   G   I     ] R [ ]         Ss_ribo
91    [               ] K [   ] K [     M V         A   ] T [ ] I [ ] Q       St_ribo D V K K X F G L F D V I H F A S V S P N I V V R D P Y A K L   Majority
                  130             140             150
121   D I [   ] V [     ] L [     ] V [ ] F A [ ] I [   ] D [ ] V V R D [   A K ] [ ] Sa_ribo
119   D V [ ] R R [                   R E     S V     V N V   D   A K ] [ ]   Ss_ribo
121   [       ] Y [       ] T [         ] P [   V V R D   M   R ] [ ]         St_ribo I S Y D P G P X S K X I X E - - V D V D I L Y L N E K E S X   Majority
                  160             170             180
151   [ ] T [ ] D P G [ ] N [ ] S K [ ] P [ ] N F G N A [ I I     R ] [ ] T   Sa_ribo
149   V [ ] Y D [ ] G [ ] Q A [ ] N E S - - [       D I L ] V [     K ] Y E   Ss_ribo
151   [         D ] [   ] F [ ] D V N [ ] - - [         ] V [   I   K   ] K   St_ribo X I X X X X I R A R X I V I K M G X K G A K V I T E N E E C   Majority
                  190             200             210
181   K V K I E S L K [   ] L [ V ] I [ ] M G S [     Q A K V ] S [ M ] E [ ] Sa_ribo
177   M [ ] E D K N [     ] A F [   ] K [ ] K [   K G A K I ] T [ ] T [     ] Ss_ribo
179   A [ ] N L D K [     ] K I [       K M ] E [ K G A V   ] [ ] Q [       ] St_ribo Y V E P Y K V X X I V D T T G A G D V F D A A F N Y X Y X E   Majority
                  220             230             240
211   [ ] C [     K ] V [ ] Q T V L D T T G A G D V F D A A [ ] Y A [ ] V Q   Sa_ribo
207   S [     ] I Q [ ] E K [     T T G A G   T F D A A     ] V T [ ] S [ ]   Ss_ribo
209   [     ] A [   ] V [ ] D N [         G A G D     D A A     ] T [   ] S L [ ] St_ribo
```

FIG. 8

```
          - - - - M X X K X X X X X V X I I G X E E L I I I P I T R N X   Majority
                         10                  20                  30
 1        - - - - - - - - - P V   N   L   V               L             R   Sa_hypo
 1        - - - -   K I   L K S L   R V     E           A V     L A E   E   Ss_hypo
 1        M N I G   R V   I N A I A K     T                             G   St_hypo X Y V L X L N F Y E D V E G G R X A R L V L V X D K Y G E I   Majority
                         40                  50                  60
 21       E   L   S               P       M           L       N         Sa_hypo
 27       Y     E C                       Q       V   V             I   Ss_hypo
 31       D F     A                       L     F     Y   F             St_hypo

- X X X X T X I K G K K K X V X A X G I E E D F X K I S X X   Majority
                         70                  80                  90
 51       - M N D I     A       A V   E V S A   K   M D   L   K I       Sa_hypo
 57       R Q D Q V N F       T F D   I   V   D   R       N S V         Ss_hypo
 61       - D Y M E   I   R   D   I I   T   E             K       N L   St_hypo I K I D X X X X X X R I P L Y F D I E I L K D X D X S X R G   Majority
                         100                 110                 120
 80         H     N R S V T D         F                 V   T   Q       Sa_hypo
 87       L   L   R V A R M F K V             V E K P   V   K           Ss_hypo
 90             K Y L K S N       F V N   S V     A N I N E             St_hypo V R G F I N Y V X X X G X I D X X K K R N X V Q L X I E E X   Majority
                         130                 140                 150
110                       Y A Y   N P   L S   I L   S L     N V     I   Sa_hypo
117       I     L Y     L S V H K E     I G   L   G L     S         L   Ss_hypo
120         K           A K F   R     V T   V     V     T         N     St_hypo V                                                             Majority 140       R                                                             Sa_hypo
147                                                                     Ss_hypo
150                                                                     St_hypo
```

FIG. 9

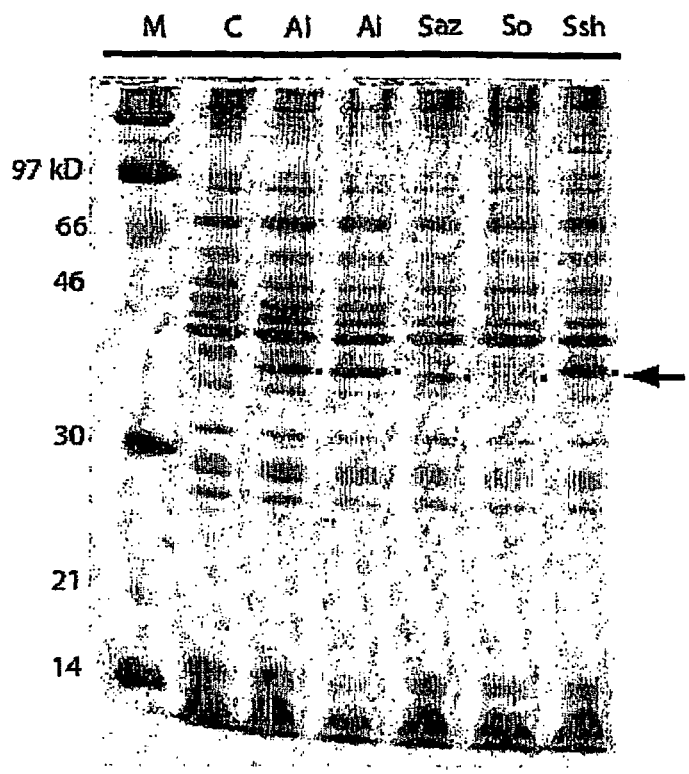
FIG. 11
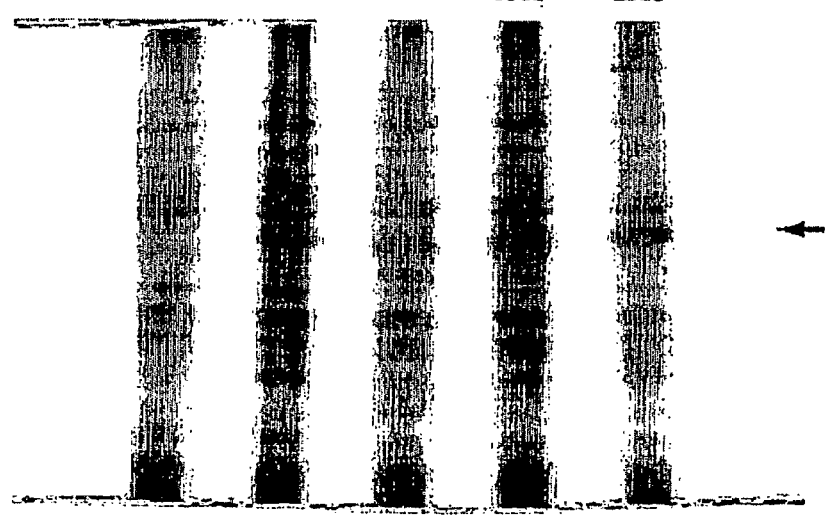
FIG. 12   * Grown in 0.01mM IPTG

|     | S K G K T F K H G I S K E T A Y K E A V E L L K Q I L E E D | Majority |
|-----|---|---|
|     |         310         320         330 | |
| 297 | S K G K K F K H G I S I D N A Y K V A E D L L R E L L V R D | Sa_dbh |
| 297 | S R G R T F P H G I S K E T A Y S E S W K L L Q K L E E D | Ss_dpo4 |
| 298 | S K S K F K T G I S K E R A Y T E S I L L K Q I L Q K D | St_dpo4 |
| 298 | S R E K N F G I S K D R A Y L E E K A E E I I K S D | Al_dpo4 |
| 297 | S K G K K F K H G I N K E K A Y E K F E L L K Q I L E E D | Saz_dpo4 |
| 296 | S K S K T F K S G I S K G R A Y T E S I E L K Q I L Q K D | So_dpo4 |
| 297 | S R G R F T H G I S K E T A Y K A V K L L Q K L L E E D | Ssh_dpo4 |
| 297 | S R G K F P H G I T K E T A Y K A S L E L L E K L L A E D | Ste_dpo4 |

|     | K R K   I R R I G V R F D K I F I S A G - L D V F F N S - | Majority |
|-----|---|---|
|     |         340         350 | |
| 327 | K R N V R R G V K L D N I I N K T N L S D F F D - I | Sa_dbh |
| 327 | E R K - I R R G V R S K - E Y E A I G L D K F F D T | Ss_dpo4 |
| 328 | S R L - V R V G V R D N Y K S K G - L D V F F N S | St_dpo4 |
| 328 | K R - L R R V G V R L G K Y K S T T - L D N F F N N V | Al_dpo4 |
| 327 | D R K - R R G V R L D D V I K T R G - L C Q F F | Saz_dpo4 |
| 326 | S R L - V R V G V R F D N Y K S K G - L D V F F N S | So_dpo4 |
| 327 | E R K - I R R G V R F S K - E I E A I G L D R F N T | Ssh_dpo4 |
| 327 | K R K - I R R G V R F S K - E I E A T S L D K F F Q F | Ste_dpo4 |

Decoration 'Decoration #1': Shade (with solid light gray) residues that match the Consensus exactly.

FIG. 15 (cont.)

SEQUENCE LISTING

<160> NUMBER OF SEQ ID NOS: 82

<210> SEQ ID NO 1
<211> LENGTH: 1062
<212> TYPE: DNA
<213> ORGANISM: Artificial Sequence
<220> FEATURE:
<223> OTHER INFORMATION: Chimeric polymerase Dpo4LFDbh.
<220> FEATURE:
<221> NAME/KEY: CDS
<222> LOCATION: (1)..(1062)

<400> SEQUENCE: 1

| | | | | | | | | | | | | | | | | |
|---|---|---|---|---|---|---|---|---|---|---|---|---|---|---|---|---|
| atg | att | gtt | ctt | ttc | gtt | gat | ttt | gac | tac | ttt | tac | gct | caa | gtt | gaa | 48 |
| Met | Ile | Val | Leu | Phe | Val | Asp | Phe | Asp | Tyr | Phe | Tyr | Ala | Gln | Val | Glu | |
| 1 | | | | 5 | | | | | 10 | | | | | 15 | | |

| gaa | gtt | tta | aat | ccg | tct | ttg | aaa | gga | aaa | cca | gtt | gtt | gtt | tgt | gta | 96 |
|---|---|---|---|---|---|---|---|---|---|---|---|---|---|---|---|---|
| Glu | Val | Leu | Asn | Pro | Ser | Leu | Lys | Gly | Lys | Pro | Val | Val | Val | Cys | Val | |
| | | | 20 | | | | | 25 | | | | | 30 | | | |

| ttt | tca | ggg | aga | ttt | gag | gat | agc | ggt | gct | gtg | gct | act | gca | aac | tat | 144 |
|---|---|---|---|---|---|---|---|---|---|---|---|---|---|---|---|---|
| Phe | Ser | Gly | Arg | Phe | Glu | Asp | Ser | Gly | Ala | Val | Ala | Thr | Ala | Asn | Tyr | |
| | | 35 | | | | | 40 | | | | | 45 | | | | |

| gaa | gct | aga | aaa | ttt | gga | gta | aaa | gct | gga | ata | cca | atc | gtt | gag | gct | 192 |
|---|---|---|---|---|---|---|---|---|---|---|---|---|---|---|---|---|
| Glu | Ala | Arg | Lys | Phe | Gly | Val | Lys | Ala | Gly | Ile | Pro | Ile | Val | Glu | Ala | |
| 50 | | | | | 55 | | | | | 60 | | | | | | |

| aag | aaa | ata | tta | cct | aat | gca | gtt | tac | tta | ccc | atg | aga | aag | gaa | gta | 240 |
|---|---|---|---|---|---|---|---|---|---|---|---|---|---|---|---|---|
| Lys | Lys | Ile | Leu | Pro | Asn | Ala | Val | Tyr | Leu | Pro | Met | Arg | Lys | Glu | Val | |
| 65 | | | | | 70 | | | | | 75 | | | | | 80 | |

| tat | cag | caa | gtt | tcc | agt | aga | ata | atg | aac | tta | cta | aga | gaa | tac | tcc | 288 |
|---|---|---|---|---|---|---|---|---|---|---|---|---|---|---|---|---|
| Tyr | Gln | Gln | Val | Ser | Ser | Arg | Ile | Met | Asn | Leu | Leu | Arg | Glu | Tyr | Ser | |
| | | | | 85 | | | | | 90 | | | | | 95 | | |

| gag | aag | atc | gag | att | gca | agt | ata | gat | gag | gct | tat | ctt | gat | atc | tca | 336 |
|---|---|---|---|---|---|---|---|---|---|---|---|---|---|---|---|---|
| Glu | Lys | Ile | Glu | Ile | Ala | Ser | Ile | Asp | Glu | Ala | Tyr | Leu | Asp | Ile | Ser | |
| | | | 100 | | | | | 105 | | | | | 110 | | | |

| gac | aaa | gtc | aga | gat | tat | aga | gag | gca | tat | aat | cta | ggt | ttg | gag | att | 384 |
|---|---|---|---|---|---|---|---|---|---|---|---|---|---|---|---|---|
| Asp | Lys | Val | Arg | Asp | Tyr | Arg | Glu | Ala | Tyr | Asn | Leu | Gly | Leu | Glu | Ile | |
| | | 115 | | | | | 120 | | | | | 125 | | | | |

| aag | aac | aaa | ata | ctt | gaa | aaa | gag | aaa | att | aca | gtt | act | gta | ggg | att | 432 |
|---|---|---|---|---|---|---|---|---|---|---|---|---|---|---|---|---|
| Lys | Asn | Lys | Ile | Leu | Glu | Lys | Glu | Lys | Ile | Thr | Val | Thr | Val | Gly | Ile | |
| 130 | | | | | 135 | | | | | 140 | | | | | | |

| tcc | aag | aat | aag | gta | ttt | gcg | aaa | att | gct | gct | gat | atg | gca | aag | cca | 480 |
|---|---|---|---|---|---|---|---|---|---|---|---|---|---|---|---|---|
| Ser | Lys | Asn | Lys | Val | Phe | Ala | Lys | Ile | Ala | Ala | Asp | Met | Ala | Lys | Pro | |
| 145 | | | | | 150 | | | | | 155 | | | | | 160 | |

| aat | gga | ata | aaa | gtt | att | gat | gat | gaa | gaa | gtt | aaa | aga | tta | ata | aga | 528 |
|---|---|---|---|---|---|---|---|---|---|---|---|---|---|---|---|---|
| Asn | Gly | Ile | Lys | Val | Ile | Asp | Asp | Glu | Glu | Val | Lys | Arg | Leu | Ile | Arg | |
| | | | | 165 | | | | | 170 | | | | | 175 | | |

| gag | cta | gat | ata | gcg | gat | gta | ccc | gga | ata | ggt | aat | ata | act | gcg | gag | 576 |
|---|---|---|---|---|---|---|---|---|---|---|---|---|---|---|---|---|
| Glu | Leu | Asp | Ile | Ala | Asp | Val | Pro | Gly | Ile | Gly | Asn | Ile | Thr | Ala | Glu | |
| | | | 180 | | | | | 185 | | | | | 190 | | | |

| aaa | cta | aag | aag | tta | ggt | att | aac | aag | cta | gtt | gat | acg | tta | agc | att | 624 |
|---|---|---|---|---|---|---|---|---|---|---|---|---|---|---|---|---|
| Lys | Leu | Lys | Lys | Leu | Gly | Ile | Asn | Lys | Leu | Val | Asp | Thr | Leu | Ser | Ile | |
| | | 195 | | | | | 200 | | | | | 205 | | | | |

| gaa | ttt | gat | aaa | cta | aag | gga | atg | ata | ggc | gaa | gct | aag | gct | aaa | tat | 672 |
|---|---|---|---|---|---|---|---|---|---|---|---|---|---|---|---|---|
| Glu | Phe | Asp | Lys | Leu | Lys | Gly | Met | Ile | Gly | Glu | Ala | Lys | Ala | Lys | Tyr | |
| 210 | | | | | 215 | | | | | 220 | | | | | | |

| ttg | atc | tct | ctg | gcc | aga | aat | aaa | tat | agt | gaa | cct | gta | gaa | aat | aaa | 720 |
|---|---|---|---|---|---|---|---|---|---|---|---|---|---|---|---|---|
| Leu | Ile | Ser | Leu | Ala | Arg | Asn | Lys | Tyr | Ser | Glu | Pro | Val | Glu | Asn | Lys | |
| 225 | | | | | 230 | | | | | 235 | | | | | 240 | |

| agt | aaa | att | cct | cat | gga | aga | tat | tta | act | tta | ccc | tat | aac | aca | aga | 768 |
|---|---|---|---|---|---|---|---|---|---|---|---|---|---|---|---|---|
| Ser | Lys | Ile | Pro | His | Gly | Arg | Tyr | Leu | Thr | Leu | Pro | Tyr | Asn | Thr | Arg | |

-continued

```
                         245                 250                 255
gat gtg aag gtt ata tta ccc tac cta aag aag gct att aat gaa gca    816
Asp Val Lys Val Ile Leu Pro Tyr Leu Lys Lys Ala Ile Asn Glu Ala
            260                 265                 270 tac aat aag gtt aat ggt att cca atg aga ata act gtt ata gct att    864
Tyr Asn Lys Val Asn Gly Ile Pro Met Arg Ile Thr Val Ile Ala Ile
            275                 280                 285 atg gaa gat cta gat att cta agt aag gga aaa aag ttt aag cat gga    912
Met Glu Asp Leu Asp Ile Leu Ser Lys Gly Lys Lys Phe Lys His Gly
        290                 295                 300 ata tct ata gat aat gct tat aaa gtt gct gag gat tta ctt aga gag    960
Ile Ser Ile Asp Asn Ala Tyr Lys Val Ala Glu Asp Leu Leu Arg Glu
305                 310                 315                 320 ttg ctg gtc aga gat aaa aga aga aat gta cga aga ata gga cta aaa   1008
Leu Leu Val Arg Asp Lys Arg Arg Asn Val Arg Arg Ile Gly Leu Lys
                325                 330                 335 tta gat aac ata ata atc aat aag aca aat tta tct gat ttc ttc gac   1056
Leu Asp Asn Ile Ile Ile Asn Lys Thr Asn Leu Ser Asp Phe Phe Asp
            340                 345                 350 att taa                                                           1062
Ile
```

<210> SEQ ID NO 2
<211> LENGTH: 353
<212> TYPE: PRT
<213> ORGANISM: Artificial Sequence
<220> FEATURE:
<223> OTHER INFORMATION: Synthetic Construct

<400> SEQUENCE: 2

```
Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
```

-continued

```
                210                 215                 220
Leu Ile Ser Leu Ala Arg Asn Lys Tyr Ser Glu Pro Val Glu Asn Lys
225                 230                 235                 240

Ser Lys Ile Pro His Gly Arg Tyr Leu Thr Leu Pro Tyr Asn Thr Arg
                245                 250                 255

Asp Val Lys Val Ile Leu Pro Tyr Leu Lys Lys Ala Ile Asn Glu Ala
                260                 265                 270

Tyr Asn Lys Val Asn Gly Ile Pro Met Arg Ile Thr Val Ile Ala Ile
            275                 280                 285

Met Glu Asp Leu Asp Ile Leu Ser Lys Gly Lys Lys Phe Lys His Gly
290                 295                 300

Ile Ser Ile Asp Asn Ala Tyr Lys Val Ala Glu Asp Leu Leu Arg Glu
305                 310                 315                 320

Leu Leu Val Arg Asp Lys Arg Arg Asn Val Arg Arg Ile Gly Leu Lys
                325                 330                 335

Leu Asp Asn Ile Ile Ile Asn Lys Thr Asn Leu Ser Asp Phe Phe Asp
                340                 345                 350

Ile
```

<210> SEQ ID NO 3
<211> LENGTH: 1062
<212> TYPE: DNA
<213> ORGANISM: Artificial Sequence
<220> FEATURE:
<223> OTHER INFORMATION: Chimeric polymerase DbhLFDpo4.
<220> FEATURE:
<221> NAME/KEY: CDS
<222> LOCATION: (1)..(1062)

<400> SEQUENCE: 3

```
atg ata gtg ata ttc gtt gat ttt gat tat ttc ttc gca caa gta gag      48
Met Ile Val Ile Phe Val Asp Phe Asp Tyr Phe Phe Ala Gln Val Glu
1               5                   10                  15 gaa gta tta aac cca caa tat aag gga aaa cca ctg gta gtt tgc gta      96
Glu Val Leu Asn Pro Gln Tyr Lys Gly Lys Pro Leu Val Val Cys Val
                20                  25                  30 tat tcc ggt aga acc aaa acg agt ggg gct gta gcc acc gcg aat tat     144
Tyr Ser Gly Arg Thr Lys Thr Ser Gly Ala Val Ala Thr Ala Asn Tyr
            35                  40                  45 gag gca aga aaa tta gga gta aag gcg gga atg cct atc ata aaa gct     192
Glu Ala Arg Lys Leu Gly Val Lys Ala Gly Met Pro Ile Ile Lys Ala
        50                  55                  60 atg cag att gca cct agc gca ata tat gtg cct atg aga aaa ccg att     240
Met Gln Ile Ala Pro Ser Ala Ile Tyr Val Pro Met Arg Lys Pro Ile
65                  70                  75                  80 tat gag gca ttc tca aat agg ata atg aac ttg tta aac aaa cat gct     288
Tyr Glu Ala Phe Ser Asn Arg Ile Met Asn Leu Leu Asn Lys His Ala
                85                  90                  95 gat aaa att gaa gta gcc agt ata gat gag gct tac tta gac gta act     336
Asp Lys Ile Glu Val Ala Ser Ile Asp Glu Ala Tyr Leu Asp Val Thr
                100                 105                 110 aat aaa gta gaa gga aac ttt gaa aat gga ata gaa tta gct agg aaa     384
Asn Lys Val Glu Gly Asn Phe Glu Asn Gly Ile Glu Leu Ala Arg Lys
            115                 120                 125 ata aag caa gag ata ctt gag aaa gaa aaa ata aca gtc act gtc gga     432
Ile Lys Gln Glu Ile Leu Glu Lys Glu Lys Ile Thr Val Thr Val Gly
        130                 135                 140 gtc gca cct aac aaa att ttg gca aaa ata att gct gac aaa agc aaa     480
Val Ala Pro Asn Lys Ile Leu Ala Lys Ile Ile Ala Asp Lys Ser Lys
```

```
                  145                 150                 155                 160
cct aat ggt ctt ggt gta att aga ccg aca gaa gta caa gat ttt ttg          528
Pro Asn Gly Leu Gly Val Ile Arg Pro Thr Glu Val Gln Asp Phe Leu
                165                 170                 175 aat gaa ttg gat att gac gaa att ccg gga ata gga agt gtt ttg gct          576
Asn Glu Leu Asp Ile Asp Glu Ile Pro Gly Ile Gly Ser Val Leu Ala
            180                 185                 190 agg aga cta aat gaa tta ggc ata cag aaa ttg aga gat att cta agt          624
Arg Arg Leu Asn Glu Leu Gly Ile Gln Lys Leu Arg Asp Ile Leu Ser
            195                 200                 205 aaa aat tac aat gaa ctt gag aag att acc gga aaa gca aaa gcc tta          672
Lys Asn Tyr Asn Glu Leu Glu Lys Ile Thr Gly Lys Ala Lys Ala Leu
    210                 215                 220 tat cta cta aag ttg gcc aga gac gag tat aac gag cct ata aga act          720
Tyr Leu Leu Lys Leu Ala Arg Asp Glu Tyr Asn Glu Pro Ile Arg Thr
225                 230                 235                 240 aga gta cga aag agt att ggg aga att gta acg atg aag aga aat agc          768
Arg Val Arg Lys Ser Ile Gly Arg Ile Val Thr Met Lys Arg Asn Ser
                245                 250                 255 agg aat ctg gag gaa ata aaa ccg tat tta ttt aga gca ata gaa gaa          816
Arg Asn Leu Glu Glu Ile Lys Pro Tyr Leu Phe Arg Ala Ile Glu Glu
            260                 265                 270 tca tat tat aag tta gat aag agg att cct aaa gct att cac gta gtc          864
Ser Tyr Tyr Lys Leu Asp Lys Arg Ile Pro Lys Ala Ile His Val Val
        275                 280                 285 gca gta acg gag gat tta gat atc gta agt aga gga aga acg ttc cct          912
Ala Val Thr Glu Asp Leu Asp Ile Val Ser Arg Gly Arg Thr Phe Pro
    290                 295                 300 cat gga ata agt aag gaa act gca tat agt gaa tca gta aaa tta tta          960
His Gly Ile Ser Lys Glu Thr Ala Tyr Ser Glu Ser Val Lys Leu Leu
305                 310                 315                 320 cag aag ata ttg gaa gag gat gag aga aag ata aga aga atc gga gta         1008
Gln Lys Ile Leu Glu Glu Asp Glu Arg Lys Ile Arg Arg Ile Gly Val
                325                 330                 335 agg ttc agt aaa ttt att gaa gca ata gga tta gac aag ttc ttc gat         1056
Arg Phe Ser Lys Phe Ile Glu Ala Ile Gly Leu Asp Lys Phe Phe Asp
            340                 345                 350 act taa                                                                 1062
Thr <210> SEQ ID NO 4
<211> LENGTH: 353
<212> TYPE: PRT
<213> ORGANISM: Artificial Sequence
<220> FEATURE:
<223> OTHER INFORMATION: Synthetic Construct

<400> SEQUENCE: 4

Met Ile Val Ile Phe Val Asp Phe Asp Tyr Phe Phe Ala Gln Val Glu
1               5                   10                  15

Glu Val Leu Asn Pro Gln Tyr Lys Gly Lys Pro Leu Val Val Cys Val
            20                  25                  30

Tyr Ser Gly Arg Thr Lys Thr Ser Gly Ala Val Ala Thr Ala Asn Tyr
        35                  40                  45

Glu Ala Arg Lys Leu Gly Val Lys Ala Gly Met Pro Ile Ile Lys Ala
    50                  55                  60

Met Gln Ile Ala Pro Ser Ala Ile Tyr Val Pro Met Arg Lys Pro Ile
65                  70                  75                  80

Tyr Glu Ala Phe Ser Asn Arg Ile Met Asn Leu Leu Asn Lys His Ala
```

```
                85                  90                  95
Asp Lys Ile Glu Val Ala Ser Ile Asp Glu Ala Tyr Leu Asp Val Thr
            100                 105                 110

Asn Lys Val Glu Gly Asn Phe Glu Asn Gly Ile Glu Leu Ala Arg Lys
            115                 120                 125

Ile Lys Gln Glu Ile Leu Glu Lys Glu Lys Ile Thr Val Thr Val Gly
        130                 135                 140

Val Ala Pro Asn Lys Ile Leu Ala Lys Ile Ile Ala Asp Lys Ser Lys
145                 150                 155                 160

Pro Asn Gly Leu Gly Val Ile Arg Pro Thr Glu Val Gln Asp Phe Leu
                165                 170                 175

Asn Glu Leu Asp Ile Asp Glu Ile Pro Gly Ile Gly Ser Val Leu Ala
            180                 185                 190

Arg Arg Leu Asn Glu Leu Gly Ile Gln Lys Leu Arg Asp Ile Leu Ser
        195                 200                 205

Lys Asn Tyr Asn Glu Leu Glu Lys Ile Thr Gly Lys Ala Lys Ala Leu
        210                 215                 220

Tyr Leu Leu Lys Leu Ala Arg Asp Glu Tyr Asn Glu Pro Ile Arg Thr
225                 230                 235                 240

Arg Val Arg Lys Ser Ile Gly Arg Ile Val Thr Met Lys Arg Asn Ser
                245                 250                 255

Arg Asn Leu Glu Glu Ile Lys Pro Tyr Leu Phe Arg Ala Ile Glu Glu
            260                 265                 270

Ser Tyr Tyr Lys Leu Asp Lys Arg Ile Pro Lys Ala Ile His Val Val
        275                 280                 285

Ala Val Thr Glu Asp Leu Asp Ile Val Ser Arg Gly Arg Thr Phe Pro
        290                 295                 300

His Gly Ile Ser Lys Glu Thr Ala Tyr Ser Glu Ser Val Lys Leu Leu
305                 310                 315                 320

Gln Lys Ile Leu Glu Glu Asp Glu Arg Lys Ile Arg Arg Ile Gly Val
                325                 330                 335

Arg Phe Ser Lys Phe Ile Glu Ala Ile Gly Leu Asp Lys Phe Phe Asp
            340                 345                 350

Thr

<210> SEQ ID NO 5
<211> LENGTH: 1065
<212> TYPE: DNA
<213> ORGANISM: Acidianus infernus
<220> FEATURE:
<221> NAME/KEY: CDS
<222> LOCATION: (1)..(1065)

<400> SEQUENCE: 5 atg att gta ctt ttc gtt gat ttt gat tac ttc ttt gct caa gtt gag      48
Met Ile Val Leu Phe Val Asp Phe Asp Tyr Phe Phe Ala Gln Val Glu
1               5                   10                  15 gaa gtc ctt aac cca gaa ctt aaa ggt aag cct gta gct gtt tgc gta      96
Glu Val Leu Asn Pro Glu Leu Lys Gly Lys Pro Val Ala Val Cys Val
            20                  25                  30 ttt tct ggt agg ttt aaa gat agt ggt gca ata gct aca gct aat tat     144
Phe Ser Gly Arg Phe Lys Asp Ser Gly Ala Ile Ala Thr Ala Asn Tyr
        35                  40                  45 gag gca aga aaa cta gga ata aaa tct ggc atg cca att cct aag gca     192
Glu Ala Arg Lys Leu Gly Ile Lys Ser Gly Met Pro Ile Pro Lys Ala
    50                  55                  60
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aag | gaa | atc | gct | cct | aac | gcg | ata | tat | tta | cct | att | aga | aag | gat | tta | 240  |
| Lys | Glu | Ile | Ala | Pro | Asn | Ala | Ile | Tyr | Leu | Pro | Ile | Arg | Lys | Asp | Leu |      |
| 65  |     |     |     | 70  |     |     |     |     | 75  |     |     |     |     | 80  |     |      |
| tat | aaa | caa | gtg | tca | gat | aga | ata | atg | tac | gga | ata | ctc | tct | aaa | tat | 288  |
| Tyr | Lys | Gln | Val | Ser | Asp | Arg | Ile | Met | Tyr | Gly | Ile | Leu | Ser | Lys | Tyr |      |
|     |     |     |     | 85  |     |     |     |     | 90  |     |     |     |     | 95  |     |      |
| tca | agt | aaa | att | gaa | att | gca | agt | ata | gat | gaa | gct | tac | ctt | gat | att | 336  |
| Ser | Ser | Lys | Ile | Glu | Ile | Ala | Ser | Ile | Asp | Glu | Ala | Tyr | Leu | Asp | Ile |      |
|     |     |     | 100 |     |     |     |     | 105 |     |     |     |     | 110 |     |     |      |
| act | gat | aga | gtg | aaa | gat | tat | tac | gag | gct | tac | caa | cta | ggt | aaa | aaa | 384  |
| Thr | Asp | Arg | Val | Lys | Asp | Tyr | Tyr | Glu | Ala | Tyr | Gln | Leu | Gly | Lys | Lys |      |
|     |     | 115 |     |     |     |     | 120 |     |     |     |     | 125 |     |     |     |      |
| ata | aag | gac | gaa | att | tat | cag | aaa | gaa | aaa | att | aca | gtt | act | att | gga | 432  |
| Ile | Lys | Asp | Glu | Ile | Tyr | Gln | Lys | Glu | Lys | Ile | Thr | Val | Thr | Ile | Gly |      |
| 130 |     |     |     |     | 135 |     |     |     |     | 140 |     |     |     |     |     |      |
| att | gct | cca | aat | aag | gtt | ttt | gct | aag | ata | ata | gcc | gaa | atg | aat | aaa | 480  |
| Ile | Ala | Pro | Asn | Lys | Val | Phe | Ala | Lys | Ile | Ile | Ala | Glu | Met | Asn | Lys |      |
| 145 |     |     |     |     | 150 |     |     |     |     | 155 |     |     |     |     | 160 |      |
| ccc | aac | ggt | tta | gga | att | tta | aag | cca | gag | gaa | gtg | gaa | gga | ttt | ata | 528  |
| Pro | Asn | Gly | Leu | Gly | Ile | Leu | Lys | Pro | Glu | Glu | Val | Glu | Gly | Phe | Ile |      |
|     |     |     |     | 165 |     |     |     |     | 170 |     |     |     |     | 175 |     |      |
| aga | tca | tta | ccg | ata | gag | gaa | gtg | cca | ggt | gta | gga | gat | tct | att | tat | 576  |
| Arg | Ser | Leu | Pro | Ile | Glu | Glu | Val | Pro | Gly | Val | Gly | Asp | Ser | Ile | Tyr |      |
|     |     |     | 180 |     |     |     |     | 185 |     |     |     |     | 190 |     |     |      |
| tct | aag | cta | aag | gaa | atg | gag | atc | aaa | tat | tta | tat | gat | gtt | cta | aaa | 624  |
| Ser | Lys | Leu | Lys | Glu | Met | Glu | Ile | Lys | Tyr | Leu | Tyr | Asp | Val | Leu | Lys |      |
|     |     | 195 |     |     |     |     | 200 |     |     |     |     | 205 |     |     |     |      |
| gtg | gat | ttt | gaa | aaa | tta | aaa | aaa | gaa | ata | gga | aaa | tct | aaa | gct | agt | 672  |
| Val | Asp | Phe | Glu | Lys | Leu | Lys | Lys | Glu | Ile | Gly | Lys | Ser | Lys | Ala | Ser |      |
|     | 210 |     |     |     |     | 215 |     |     |     |     | 220 |     |     |     |     |      |
| tac | ttg | tat | tct | tta | gca | aac | aat | acc | tat | gct | gaa | ccg | gta | aag | gaa | 720  |
| Tyr | Leu | Tyr | Ser | Leu | Ala | Asn | Asn | Thr | Tyr | Ala | Glu | Pro | Val | Lys | Glu |      |
| 225 |     |     |     |     | 230 |     |     |     |     | 235 |     |     |     |     | 240 |      |
| aaa | gta | agg | aag | cat | att | gga | aga | tat | gtt | aca | atg | aaa | aag | aac | tca | 768  |
| Lys | Val | Arg | Lys | His | Ile | Gly | Arg | Tyr | Val | Thr | Met | Lys | Lys | Asn | Ser |      |
|     |     |     |     | 245 |     |     |     |     | 250 |     |     |     |     | 255 |     |      |
| aga | gat | att | aaa | gag | ata | ctt | cca | tac | ttg | aag | agg | gca | ata | gac | gaa | 816  |
| Arg | Asp | Ile | Lys | Glu | Ile | Leu | Pro | Tyr | Leu | Lys | Arg | Ala | Ile | Asp | Glu |      |
|     |     |     | 260 |     |     |     |     | 265 |     |     |     |     | 270 |     |     |      |
| gct | tat | tct | aag | acc | aac | gga | ggt | ata | cca | aag | acc | tta | gcg | gtt | gtt | 864  |
| Ala | Tyr | Ser | Lys | Thr | Asn | Gly | Gly | Ile | Pro | Lys | Thr | Leu | Ala | Val | Val |      |
|     |     | 275 |     |     |     |     | 280 |     |     |     |     | 285 |     |     |     |      |
| gcg | ata | atg | gaa | gat | ctt | gat | att | gta | agt | agg | gaa | aaa | act | ttt | aac | 912  |
| Ala | Ile | Met | Glu | Asp | Leu | Asp | Ile | Val | Ser | Arg | Glu | Lys | Thr | Phe | Asn |      |
| 290 |     |     |     |     | 295 |     |     |     |     | 300 |     |     |     |     |     |      |
| ttt | ggc | ata | agt | aag | gac | agg | gcg | tat | tta | gaa | gct | gaa | aaa | ctc | ttg | 960  |
| Phe | Gly | Ile | Ser | Lys | Asp | Arg | Ala | Tyr | Leu | Glu | Ala | Glu | Lys | Leu | Leu |      |
| 305 |     |     |     | 310 |     |     |     |     | 315 |     |     |     |     | 320 |     |      |
| gaa | gaa | atc | ata | aaa | tct | gat | aaa | aga | aga | tta | aga | aga | gta | ggc | gta | 1008 |
| Glu | Glu | Ile | Ile | Lys | Ser | Asp | Lys | Arg | Arg | Leu | Arg | Arg | Val | Gly | Val |      |
|     |     |     |     | 325 |     |     |     |     | 330 |     |     |     |     | 335 |     |      |
| aga | ttg | ggt | aag | ata | tac | aaa | tcg | act | aca | cta | gac | aac | ttc | ttc | aat | 1056 |
| Arg | Leu | Gly | Lys | Ile | Tyr | Lys | Ser | Thr | Thr | Leu | Asp | Asn | Phe | Phe | Asn |      |
|     |     |     | 340 |     |     |     |     | 345 |     |     |     |     | 350 |     |     |      |
| aac | gtc | tag |     |     |     |     |     |     |     |     |     |     |     |     |     | 1065 |
| Asn | Val |     |     |     |     |     |     |     |     |     |     |     |     |     |     |      |

<210> SEQ ID NO 6
<211> LENGTH: 354
<212> TYPE: PRT

<213> ORGANISM: Acidianus infernus

<400> SEQUENCE: 6

```
Met Ile Val Leu Phe Val Asp Phe Asp Tyr Phe Ala Gln Val Glu
1               5                  10                  15

Glu Val Leu Asn Pro Glu Leu Lys Gly Lys Pro Val Ala Val Cys Val
            20                  25                  30

Phe Ser Gly Arg Phe Lys Asp Ser Gly Ala Ile Ala Thr Ala Asn Tyr
        35                  40                  45

Glu Ala Arg Lys Leu Gly Ile Lys Ser Gly Met Pro Ile Pro Lys Ala
    50                  55                  60

Lys Glu Ile Ala Pro Asn Ala Ile Tyr Leu Pro Ile Arg Lys Asp Leu
65                  70                  75                  80

Tyr Lys Gln Val Ser Asp Arg Ile Met Tyr Gly Ile Leu Ser Lys Tyr
                85                  90                  95

Ser Ser Lys Ile Glu Ile Ala Ser Ile Asp Glu Ala Tyr Leu Asp Ile
            100                 105                 110

Thr Asp Arg Val Lys Asp Tyr Tyr Glu Ala Tyr Gln Leu Gly Lys Lys
        115                 120                 125

Ile Lys Asp Glu Ile Tyr Gln Lys Glu Lys Ile Thr Val Thr Ile Gly
    130                 135                 140

Ile Ala Pro Asn Lys Val Phe Ala Lys Ile Ile Ala Glu Met Asn Lys
145                 150                 155                 160

Pro Asn Gly Leu Gly Ile Leu Lys Pro Glu Glu Val Glu Gly Phe Ile
                165                 170                 175

Arg Ser Leu Pro Ile Glu Glu Val Pro Gly Val Gly Asp Ser Ile Tyr
            180                 185                 190

Ser Lys Leu Lys Glu Met Glu Ile Lys Tyr Leu Tyr Asp Val Leu Lys
        195                 200                 205

Val Asp Phe Glu Lys Leu Lys Lys Glu Ile Gly Lys Ser Lys Ala Ser
    210                 215                 220

Tyr Leu Tyr Ser Leu Ala Asn Asn Thr Tyr Ala Glu Pro Val Lys Glu
225                 230                 235                 240

Lys Val Arg Lys His Ile Gly Arg Tyr Val Thr Met Lys Lys Asn Ser
                245                 250                 255

Arg Asp Ile Lys Glu Ile Leu Pro Tyr Leu Lys Arg Ala Ile Asp Glu
            260                 265                 270

Ala Tyr Ser Lys Thr Asn Gly Gly Ile Pro Lys Thr Leu Ala Val Val
        275                 280                 285

Ala Ile Met Glu Asp Leu Asp Ile Val Ser Arg Glu Lys Thr Phe Asn
    290                 295                 300

Phe Gly Ile Ser Lys Asp Arg Ala Tyr Leu Glu Ala Lys Leu Leu
305                 310                 315                 320

Glu Glu Ile Ile Lys Ser Asp Lys Arg Arg Leu Arg Arg Val Gly Val
                325                 330                 335

Arg Leu Gly Lys Ile Tyr Lys Ser Thr Thr Leu Asp Asn Phe Phe Asn
            340                 345                 350

Asn Val
```

<210> SEQ ID NO 7
<211> LENGTH: 1053
<212> TYPE: DNA
<213> ORGANISM: Stygiolobus azoricus
<220> FEATURE:
<221> NAME/KEY: CDS

<222> LOCATION: (1)..(1053)

<400> SEQUENCE: 7

```
atg att gtg ctc ttc gtg gac ttt gac tac ttt ttc gcc caa gta gaa      48
Met Ile Val Leu Phe Val Asp Phe Asp Tyr Phe Phe Ala Gln Val Glu
1               5                   10                  15 gag gta ctt aac ccc cag tat aag ggc agg ccg gta att gtc tgc gtt      96
Glu Val Leu Asn Pro Gln Tyr Lys Gly Arg Pro Val Ile Val Cys Val
            20                  25                  30 tac tcg gga agg act aag acc agt ggt gct gtg gct aca ggc aat tac     144
Tyr Ser Gly Arg Thr Lys Thr Ser Gly Ala Val Ala Thr Gly Asn Tyr
        35                  40                  45 gag gct aga aaa ctg gga gta aag gct ggg ata cca ata att aag gcg     192
Glu Ala Arg Lys Leu Gly Val Lys Ala Gly Ile Pro Ile Ile Lys Ala
    50                  55                  60 atg gag tta gcc cct tcc gct ata ttt tta ccc atg agg aag gag gtc     240
Met Glu Leu Ala Pro Ser Ala Ile Phe Leu Pro Met Arg Lys Glu Val
65                  70                  75                  80 tac caa gag gtt tct aat agg att atg aac gga ata ctc agg aaa tac     288
Tyr Gln Glu Val Ser Asn Arg Ile Met Asn Gly Ile Leu Arg Lys Tyr
                85                  90                  95 acc tca aag ctc gaa ata gcg agt att gac gaa gca tac tta aat ata     336
Thr Ser Lys Leu Glu Ile Ala Ser Ile Asp Glu Ala Tyr Leu Asn Ile
            100                 105                 110 aca gat aaa gtg aag gac ttt gat gaa gct tac gcc cta ggt aag aaa     384
Thr Asp Lys Val Lys Asp Phe Asp Glu Ala Tyr Ala Leu Gly Lys Lys
        115                 120                 125 ata aaa gag gag ata ttt gag aag gaa aaa cta aca gtg act ata gga     432
Ile Lys Glu Glu Ile Phe Glu Lys Glu Lys Leu Thr Val Thr Ile Gly
    130                 135                 140 att gcc cct aat aaa gta ttt gct aaa ata ata gct gat aag aat aaa     480
Ile Ala Pro Asn Lys Val Phe Ala Lys Ile Ile Ala Asp Lys Asn Lys
145                 150                 155                 160 ccg aat ggg tta gcc gtg cta aag cca gag gac gtt cag tct ttc ctc     528
Pro Asn Gly Leu Ala Val Leu Lys Pro Glu Asp Val Gln Ser Phe Leu
                165                 170                 175 caa agc ctg gac att gac gaa ata ccg ggg ata gga aag atg ttg act     576
Gln Ser Leu Asp Ile Asp Glu Ile Pro Gly Ile Gly Lys Met Leu Thr
            180                 185                 190 gac aaa ctg aaa gaa atg ggg gtt aac aag cta gtt gat gtc ttg aac     624
Asp Lys Leu Lys Glu Met Gly Val Asn Lys Leu Val Asp Val Leu Asn
        195                 200                 205 ttt gac ttc acg aag tta gaa agg gaa ata ggt agg tct aag gca act     672
Phe Asp Phe Thr Lys Leu Glu Arg Glu Ile Gly Arg Ser Lys Ala Thr
    210                 215                 220 tat ttg gtc aaa tta gct cag aac aga tac aat gaa ccg gtg gag gac     720
Tyr Leu Val Lys Leu Ala Gln Asn Arg Tyr Asn Glu Pro Val Glu Asp
225                 230                 235                 240 aag acc aaa aag cct cac ggt agg att tta aca tta ccg tat aat acg     768
Lys Thr Lys Lys Pro His Gly Arg Ile Leu Thr Leu Pro Tyr Asn Thr
                245                 250                 255 aga aag ccc gaa gta ata cta cct cac ctt aag aga gct gca gac gag     816
Arg Lys Pro Glu Val Ile Leu Pro His Leu Lys Arg Ala Ala Asp Glu
            260                 265                 270 gct tat agc aaa gtt caa ggc gtt cct atg aag ata aca gtt gtg gca     864
Ala Tyr Ser Lys Val Gln Gly Val Pro Met Lys Ile Thr Val Val Ala
        275                 280                 285 ata atg gag gac tta gac atc gta agc aaa gga aag aag ttt aaa cat     912
Ile Met Glu Asp Leu Asp Ile Val Ser Lys Gly Lys Lys Phe Lys His
    290                 295                 300
```

```
ggg atc aat aag gaa aaa gca tat gaa aaa gcg ttc gaa cta ctc aaa    960
Gly Ile Asn Lys Glu Lys Ala Tyr Glu Lys Ala Phe Glu Leu Leu Lys
305                 310                 315                 320 cag atc ctc gag gag gac gat aga aaa ata cgt aga ata gga gtt agg   1008
Gln Ile Leu Glu Glu Asp Asp Arg Lys Ile Arg Arg Ile Gly Val Arg
            325                 330                 335 tta gat gac gtg att aag acc aga ggg tta gac cag ttc ttc taa      1053
Leu Asp Asp Val Ile Lys Thr Arg Gly Leu Asp Gln Phe Phe
        340                 345                 350
```

<210> SEQ ID NO 8
<211> LENGTH: 350
<212> TYPE: PRT
<213> ORGANISM: Stygiolobus azoricus

<400> SEQUENCE: 8

```
Met Ile Val Leu Phe Val Asp Phe Asp Tyr Phe Phe Ala Gln Val Glu
1               5                   10                  15

Glu Val Leu Asn Pro Gln Tyr Lys Gly Arg Pro Val Ile Val Cys Val
            20                  25                  30

Tyr Ser Gly Arg Thr Lys Thr Ser Gly Ala Val Ala Thr Gly Asn Tyr
        35                  40                  45

Glu Ala Arg Lys Leu Gly Val Lys Ala Gly Ile Pro Ile Ile Lys Ala
    50                  55                  60

Met Glu Leu Ala Pro Ser Ala Ile Phe Leu Pro Met Arg Lys Glu Val
65                  70                  75                  80

Tyr Gln Glu Val Ser Asn Arg Ile Met Asn Gly Ile Leu Arg Lys Tyr
                85                  90                  95

Thr Ser Lys Leu Glu Ile Ala Ser Ile Asp Glu Ala Tyr Leu Asn Ile
            100                 105                 110

Thr Asp Lys Val Lys Asp Phe Asp Glu Ala Tyr Ala Leu Gly Lys Lys
        115                 120                 125

Ile Lys Glu Glu Ile Phe Glu Lys Glu Lys Leu Thr Val Thr Ile Gly
    130                 135                 140

Ile Ala Pro Asn Lys Val Phe Ala Lys Ile Ile Ala Asp Lys Asn Lys
145                 150                 155                 160

Pro Asn Gly Leu Ala Val Leu Lys Pro Glu Asp Val Gln Ser Phe Leu
                165                 170                 175

Gln Ser Leu Asp Ile Asp Glu Ile Pro Gly Ile Gly Lys Met Leu Thr
            180                 185                 190

Asp Lys Leu Lys Glu Met Gly Val Asn Lys Leu Val Asp Val Leu Asn
        195                 200                 205

Phe Asp Phe Thr Lys Leu Glu Arg Glu Ile Gly Arg Ser Lys Ala Thr
    210                 215                 220

Tyr Leu Val Lys Leu Ala Gln Asn Arg Tyr Asn Glu Pro Val Glu Asp
225                 230                 235                 240

Lys Thr Lys Lys Pro His Gly Arg Ile Leu Thr Leu Pro Tyr Asn Thr
                245                 250                 255

Arg Lys Pro Glu Val Ile Leu Pro His Leu Lys Arg Ala Ala Asp Glu
            260                 265                 270

Ala Tyr Ser Lys Val Gln Gly Val Pro Met Lys Ile Thr Val Val Ala
        275                 280                 285

Ile Met Glu Asp Leu Asp Ile Val Ser Lys Gly Lys Phe Lys His
    290                 295                 300

Gly Ile Asn Lys Glu Lys Ala Tyr Glu Lys Ala Phe Glu Leu Leu Lys
```

```
                305                 310                 315                 320
Gln Ile Leu Glu Glu Asp Asp Arg Lys Ile Arg Arg Ile Gly Val Arg
                    325                 330                 335

Leu Asp Asp Val Ile Lys Thr Arg Gly Leu Asp Gln Phe Phe
                340                 345                 350

<210> SEQ ID NO 9
<211> LENGTH: 1056
<212> TYPE: DNA
<213> ORGANISM: Sulfurisphaera ohwakuensis
<220> FEATURE:
<221> NAME/KEY: CDS
<222> LOCATION: (1)..(1056)

<400> SEQUENCE: 9 atg ata ata ttg ttt gtg gat ttt gat tat ttc ttt gct caa gta gag      48
Met Ile Ile Leu Phe Val Asp Phe Asp Tyr Phe Phe Ala Gln Val Glu
 1               5                  10                  15 gag gtt tta aat cct caa tat aaa gga aaa cct ctt ata gtc tgt gtt      96
Glu Val Leu Asn Pro Gln Tyr Lys Gly Lys Pro Leu Ile Val Cys Val
             20                  25                  30 tat tct ggt aga aat gag aaa agt gga gct gta gcg aca gct aat tat     144
Tyr Ser Gly Arg Asn Glu Lys Ser Gly Ala Val Ala Thr Ala Asn Tyr
         35                  40                  45 gaa gct agg aag ttg gga gta aaa gct gga atg cct ata tca aga gca     192
Glu Ala Arg Lys Leu Gly Val Lys Ala Gly Met Pro Ile Ser Arg Ala
     50                  55                  60 atg gaa ttg gca cca aat gca ata ttc gtt cca atg cac aaa gaa gta     240
Met Glu Leu Ala Pro Asn Ala Ile Phe Val Pro Met His Lys Glu Val
 65                  70                  75                  80 tat act gag gtt tct aat aga ata atg agc ata atc agt agc tat tcg     288
Tyr Thr Glu Val Ser Asn Arg Ile Met Ser Ile Ile Ser Ser Tyr Ser
                 85                  90                  95 gat aaa att gaa ata gct agc ata gac gag gcc tac att gat ata act     336
Asp Lys Ile Glu Ile Ala Ser Ile Asp Glu Ala Tyr Ile Asp Ile Thr
            100                 105                 110 agc aag gtg aaa aat ttt gaa gag gcg ata gaa tta gga aaa aaa tta     384
Ser Lys Val Lys Asn Phe Glu Glu Ala Ile Glu Leu Gly Lys Lys Leu
        115                 120                 125 aaa cga gaa ata atg gag aag gaa aag att aca gta aca gtt gga atc     432
Lys Arg Glu Ile Met Glu Lys Glu Lys Ile Thr Val Thr Val Gly Ile
    130                 135                 140 gca cca aat aag gtt ttt gca aaa atc att gca gat aga gta aaa cca     480
Ala Pro Asn Lys Val Phe Ala Lys Ile Ile Ala Asp Arg Val Lys Pro
145                 150                 155                 160 aat gga tta gga gta gta aaa cca gac gaa ata gag gag ttc atc aaa     528
Asn Gly Leu Gly Val Val Lys Pro Asp Glu Ile Glu Glu Phe Ile Lys
                165                 170                 175 agt att gat ata gat gag gtt cct ggt gta ggt aat gtt att tct gaa     576
Ser Ile Asp Ile Asp Glu Val Pro Gly Val Gly Asn Val Ile Ser Glu
            180                 185                 190 aga ctt cat tca tta ggt gta aat aag ttg ata gat att tta tct gtt     624
Arg Leu His Ser Leu Gly Val Asn Lys Leu Ile Asp Ile Leu Ser Val
        195                 200                 205 tca ttt gat aaa tta aaa gaa gag ata ggg gaa gct aag gca ttt tat     672
Ser Phe Asp Lys Leu Lys Glu Glu Ile Gly Glu Ala Lys Ala Phe Tyr
    210                 215                 220 ctt tat aga tta gcc aca aac tct tat ttt gag ccg gta tta aat aaa     720
Leu Tyr Arg Leu Ala Thr Asn Ser Tyr Phe Glu Pro Val Leu Asn Lys
225                 230                 235                 240
```

```
gaa agg gta ccg cat gga aga tat ttg aca tta cct aaa aat act aga    768
Glu Arg Val Pro His Gly Arg Tyr Leu Thr Leu Pro Lys Asn Thr Arg
            245                 250                 255 gat ata aaa gtg ata gaa cct tat ctg aaa aag gct ata gat gaa gca    816
Asp Ile Lys Val Ile Glu Pro Tyr Leu Lys Lys Ala Ile Asp Glu Ala
        260                 265                 270 tac aac aaa ata gaa ggt ata cct aag aga atg act gtg gta act atc    864
Tyr Asn Lys Ile Glu Gly Ile Pro Lys Arg Met Thr Val Val Thr Ile
    275                 280                 285 atg caa gac tta gac atc gta agt aaa agt aaa act ttt aaa tct ggt    912
Met Gln Asp Leu Asp Ile Val Ser Lys Ser Lys Thr Phe Lys Ser Gly
290                 295                 300 ata agc aaa gaa aga gct tat aca gaa tca att gaa tta tta aaa caa    960
Ile Ser Lys Glu Arg Ala Tyr Thr Glu Ser Ile Glu Leu Leu Lys Gln
305                 310                 315                 320 att tta caa aaa gat agt aga tta gtt aga aga gtt gga gta aga ttt    1008
Ile Leu Gln Lys Asp Ser Arg Leu Val Arg Arg Val Gly Val Arg Phe
                325                 330                 335 gat aat ata tac aaa tcg aag gga tta gac gtt ttc ttc aat agt taa    1056
Asp Asn Ile Tyr Lys Ser Lys Gly Leu Asp Val Phe Phe Asn Ser
            340                 345                 350

<210> SEQ ID NO 10
<211> LENGTH: 351
<212> TYPE: PRT
<213> ORGANISM: Sulfurisphaera ohwakuensis

<400> SEQUENCE: 10

Met Ile Ile Leu Phe Val Asp Phe Asp Tyr Phe Phe Ala Gln Val Glu
1               5                   10                  15

Glu Val Leu Asn Pro Gln Tyr Lys Gly Lys Pro Leu Ile Val Cys Val
            20                  25                  30

Tyr Ser Gly Arg Asn Glu Lys Ser Gly Ala Val Ala Thr Ala Asn Tyr
        35                  40                  45

Glu Ala Arg Lys Leu Gly Val Lys Ala Gly Met Pro Ile Ser Arg Ala
    50                  55                  60

Met Glu Leu Ala Pro Asn Ala Ile Phe Val Pro Met His Lys Glu Val
65                  70                  75                  80

Tyr Thr Glu Val Ser Asn Arg Ile Met Ser Ile Ser Ser Tyr Ser
            85                  90                  95

Asp Lys Ile Glu Ile Ala Ser Ile Asp Glu Ala Tyr Ile Asp Ile Thr
        100                 105                 110

Ser Lys Val Lys Asn Phe Glu Glu Ala Ile Glu Leu Gly Lys Lys Leu
    115                 120                 125

Lys Arg Glu Ile Met Glu Lys Glu Lys Ile Thr Val Thr Val Gly Ile
    130                 135                 140

Ala Pro Asn Lys Val Phe Ala Lys Ile Ile Ala Asp Arg Val Lys Pro
145                 150                 155                 160

Asn Gly Leu Gly Val Val Lys Pro Asp Glu Ile Glu Glu Phe Ile Lys
            165                 170                 175

Ser Ile Asp Ile Asp Glu Val Pro Gly Val Gly Asn Val Ile Ser Glu
        180                 185                 190

Arg Leu His Ser Leu Gly Val Asn Lys Leu Ile Asp Ile Leu Ser Val
    195                 200                 205

Ser Phe Asp Lys Leu Lys Glu Glu Ile Gly Glu Ala Lys Ala Phe Tyr
    210                 215                 220

Leu Tyr Arg Leu Ala Thr Asn Ser Tyr Phe Glu Pro Val Leu Asn Lys
```

```
                225                 230                 235                 240
Glu Arg Val Pro His Gly Arg Tyr Leu Thr Leu Pro Lys Asn Thr Arg
                    245                 250                 255

Asp Ile Lys Val Ile Glu Pro Tyr Leu Lys Lys Ala Ile Asp Glu Ala
                260                 265                 270

Tyr Asn Lys Ile Glu Gly Ile Pro Lys Arg Met Thr Val Val Thr Ile
            275                 280                 285

Met Gln Asp Leu Asp Ile Val Ser Lys Ser Lys Thr Phe Lys Ser Gly
        290                 295                 300

Ile Ser Lys Glu Arg Ala Tyr Thr Glu Ser Ile Glu Leu Leu Lys Gln
305                 310                 315                 320

Ile Leu Gln Lys Asp Ser Arg Leu Val Arg Arg Val Gly Val Arg Phe
                325                 330                 335

Asp Asn Ile Tyr Lys Ser Lys Gly Leu Asp Val Phe Phe Asn Ser
                340                 345                 350

<210> SEQ ID NO 11
<211> LENGTH: 1059
<212> TYPE: DNA
<213> ORGANISM: Sulfolobus shibatae
<220> FEATURE:
<221> NAME/KEY: CDS
<222> LOCATION: (1)..(1059)

<400> SEQUENCE: 11 atg atc att ctc ttc gtt gat ttt gac tac ttt tac gct caa gtt gag      48
Met Ile Ile Leu Phe Val Asp Phe Asp Tyr Phe Tyr Ala Gln Val Glu
1               5                   10                  15 gaa gtt tta gat aca tcc ttg aaa gga aag cca gtg gtc gtt tgt gta      96
Glu Val Leu Asp Thr Ser Leu Lys Gly Lys Pro Val Val Val Cys Val
                20                  25                  30 ttt tct ggt aga ttt gag gat agt ggg gct gtg gct act gcg aac tac     144
Phe Ser Gly Arg Phe Glu Asp Ser Gly Ala Val Ala Thr Ala Asn Tyr
            35                  40                  45 gaa gcc aga aaa ttt ggg ata aaa gct gga ata cca ata gtt gag gca     192
Glu Ala Arg Lys Phe Gly Ile Lys Ala Gly Ile Pro Ile Val Glu Ala
        50                  55                  60 aag aaa att ttg cca aat gca gtt tac ttg ccc atg aga aag gaa gtg     240
Lys Lys Ile Leu Pro Asn Ala Val Tyr Leu Pro Met Arg Lys Glu Val
65                  70                  75                  80 tat caa caa gtt tcc aat aga ata atg agg ttg cta cgg gag tac tct     288
Tyr Gln Gln Val Ser Asn Arg Ile Met Arg Leu Leu Arg Glu Tyr Ser
                85                  90                  95 gag aag atc gag att gcg agt ata gat gag gcc tat ctc gat atc tca     336
Glu Lys Ile Glu Ile Ala Ser Ile Asp Glu Ala Tyr Leu Asp Ile Ser
            100                 105                 110 gac aag gtt aag gat tat caa gag gca tat aat cta ggg ttg gag att     384
Asp Lys Val Lys Asp Tyr Gln Glu Ala Tyr Asn Leu Gly Leu Glu Ile
        115                 120                 125 aag aac aaa ata ctc gaa aaa gag aaa att aca gtt act gtt ggg att     432
Lys Asn Lys Ile Leu Glu Lys Glu Lys Ile Thr Val Thr Val Gly Ile
    130                 135                 140 tcc aag aat aag gta ttc gca aaa att gct gct gat atg gca aaa cca     480
Ser Lys Asn Lys Val Phe Ala Lys Ile Ala Ala Asp Met Ala Lys Pro
145                 150                 155                 160 aac ggg ata aag gtt att gat aat gat gaa gtt aaa agg ctg ata aga     528
Asn Gly Ile Lys Val Ile Asp Asn Asp Glu Val Lys Arg Leu Ile Arg
                165                 170                 175 gag cta gat ata ggt gat gta cca gga gtt ggt agt att act gct gag     576
Glu Leu Asp Ile Gly Asp Val Pro Gly Val Gly Ser Ile Thr Ala Glu
```

```
aaa cta aag aag tta ggc gtc aac aaa cta gtt gac acg tta aga gtt    624
Lys Leu Lys Lys Leu Gly Val Asn Lys Leu Val Asp Thr Leu Arg Val
        195                 200                 205 gaa ttt ggc gaa cta aaa aga ata att ggt gag gcg aaa gcc aaa tat    672
Glu Phe Gly Glu Leu Lys Arg Ile Ile Gly Glu Ala Lys Ala Lys Tyr
    210                 215                 220 ctg tac tct ttg gct aga gat gag tat aac gaa cct ata aga gct aga    720
Leu Tyr Ser Leu Ala Arg Asp Glu Tyr Asn Glu Pro Ile Arg Ala Arg
225                 230                 235                 240 gta cgg aag agt att ggg aga ata gta aca atg aag aga aat agc agg    768
Val Arg Lys Ser Ile Gly Arg Ile Val Thr Met Lys Arg Asn Ser Arg
                245                 250                 255 gac ttg gag gaa ata aaa ccg tat tta ttt aga gca ata gag gag gca    816
Asp Leu Glu Glu Ile Lys Pro Tyr Leu Phe Arg Ala Ile Glu Glu Ala
            260                 265                 270 tat cat aag tta gat aag aag att cct aaa gct att cac gta gtt gca    864
Tyr His Lys Leu Asp Lys Lys Ile Pro Lys Ala Ile His Val Val Ala
        275                 280                 285 ata acg gaa gat tta gat atc gta agt aga gga aga act ttt acc cat    912
Ile Thr Glu Asp Leu Asp Ile Val Ser Arg Gly Arg Thr Phe Thr His
    290                 295                 300 gga ata agt aag gag aca gct tat aag gaa gca gta aaa tta ctg caa    960
Gly Ile Ser Lys Glu Thr Ala Tyr Lys Glu Ala Val Lys Leu Leu Gln
305                 310                 315                 320 aaa ata ttg gaa gag gat gag aga aaa ata agg aga att gga gtg agg   1008
Lys Ile Leu Glu Glu Asp Glu Arg Lys Ile Arg Arg Ile Gly Val Arg
                325                 330                 335 ttt agt aaa ttc att gag gca ata ggg tta gat aga ttc ttc aat act   1056
Phe Ser Lys Phe Ile Glu Ala Ile Gly Leu Asp Arg Phe Phe Asn Thr
            340                 345                 350 taa                                                                1059
```

<210> SEQ ID NO 12
<211> LENGTH: 352
<212> TYPE: PRT
<213> ORGANISM: Sulfolobus shibatae

<400> SEQUENCE: 12

```
Met Ile Ile Leu Phe Val Asp Phe Asp Tyr Phe Tyr Ala Gln Val Glu
1               5                   10                  15

Glu Val Leu Asp Thr Ser Leu Lys Gly Lys Pro Val Val Cys Val
            20                  25                  30

Phe Ser Gly Arg Phe Glu Asp Ser Gly Ala Val Ala Thr Ala Asn Tyr
        35                  40                  45

Glu Ala Arg Lys Phe Gly Ile Lys Ala Gly Ile Pro Ile Val Glu Ala
    50                  55                  60

Lys Lys Ile Leu Pro Asn Ala Val Tyr Leu Pro Met Arg Lys Glu Val
65                  70                  75                  80

Tyr Gln Gln Val Ser Asn Arg Ile Met Arg Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Lys Asp Tyr Gln Glu Ala Tyr Asn Leu Gly Leu Glu Ile
        115                 120                 125

Lys Asn Lys Ile Leu Glu Lys Glu Lys Ile Thr Val Thr Val Gly Ile
    130                 135                 140
```

```
Ser Lys Asn Lys Val Phe Ala Lys Ile Ala Ala Asp Met Ala Lys Pro
145                 150                 155                 160

Asn Gly Ile Lys Val Ile Asp Asn Asp Glu Val Lys Arg Leu Ile Arg
                165                 170                 175

Glu Leu Asp Ile Gly Asp Val Pro Gly Val Gly Ser Ile Thr Ala Glu
            180                 185                 190

Lys Leu Lys Lys Leu Gly Val Asn Lys Leu Val Asp Thr Leu Arg Val
        195                 200                 205

Glu Phe Gly Glu Leu Lys Arg Ile Ile Gly Glu Ala Lys Ala Lys Tyr
    210                 215                 220

Leu Tyr Ser Leu Ala Arg Asp Glu Tyr Asn Glu Pro Ile Arg Ala Arg
225                 230                 235                 240

Val Arg Lys Ser Ile Gly Arg Ile Val Thr Met Lys Arg Asn Ser Arg
                245                 250                 255

Asp Leu Glu Glu Ile Lys Pro Tyr Leu Phe Arg Ala Ile Glu Glu Ala
            260                 265                 270

Tyr His Lys Leu Asp Lys Lys Ile Pro Lys Ala Ile His Val Val Ala
        275                 280                 285

Ile Thr Glu Asp Leu Asp Ile Val Ser Arg Gly Arg Thr Phe Thr His
    290                 295                 300

Gly Ile Ser Lys Glu Thr Ala Tyr Lys Glu Ala Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Arg Phe Phe Asn Thr
            340                 345                 350

<210> SEQ ID NO 13
<211> LENGTH: 1059
<212> TYPE: DNA
<213> ORGANISM: Sulfolobus tengchongensis
<220> FEATURE:
<221> NAME/KEY: CDS
<222> LOCATION: (1)..(1059)

<400> SEQUENCE: 13 atg att atc tta ttc gta gat ttc gac tat ttt tac gct caa gtt gaa     48
Met Ile Ile Leu Phe Val Asp Phe Asp Tyr Phe Tyr Ala Gln Val Glu
1               5                   10                  15 gaa gtc cta aac cca tca ctc aaa gga aaa cca gta gtt gtc tgc gta     96
Glu Val Leu Asn Pro Ser Leu Lys Gly Lys Pro Val Val Val Cys Val
            20                  25                  30 ttt tct gga aga act gag aat agt gga gca gta gct aca gct aat tat    144
Phe Ser Gly Arg Thr Glu Asn Ser Gly Ala Val Ala Thr Ala Asn Tyr
        35                  40                  45 gag gct aga aaa tta gga gtt aaa gca gga atg cct att gta aag gct    192
Glu Ala Arg Lys Leu Gly Val Lys Ala Gly Met Pro Ile Val Lys Ala
    50                  55                  60 aag gaa ata ctt cca gac gca att tat ttg cca atg aga aag gaa gtt    240
Lys Glu Ile Leu Pro Asp Ala Ile Tyr Leu Pro Met Arg Lys Glu Val
65                  70                  75                  80 tat caa caa gta tca aat aga att atg aat ata tta aga aaa tat tct    288
Tyr Gln Gln Val Ser Asn Arg Ile Met Asn Ile Leu Arg Lys Tyr Ser
                85                  90                  95 agg aaa att gag att gcc agc atc gat gag gcc tac ctg gat ata agc    336
Arg Lys Ile Glu Ile Ala Ser Ile Asp Glu Ala Tyr Leu Asp Ile Ser
            100                 105                 110
```

```
gat aaa gta aac aat tat act gat gcg tat aaa att gga tta cag att      384
Asp Lys Val Asn Asn Tyr Thr Asp Ala Tyr Lys Ile Gly Leu Gln Ile
        115                 120                 125 aag aat gaa att tat gaa aaa gag aaa ata acg gtg acg gtg ggc att      432
Lys Asn Glu Ile Tyr Glu Lys Glu Lys Ile Thr Val Thr Val Gly Ile
    130                 135                 140 tca aaa aat aaa gtg ttc gca aaa ata gca gct gaa atg gca aag ccc      480
Ser Lys Asn Lys Val Phe Ala Lys Ile Ala Ala Glu Met Ala Lys Pro
145                 150                 155                 160 aat gga ata aaa gta att gat gat aat gaa gtt aaa aag ttg ata agg      528
Asn Gly Ile Lys Val Ile Asp Asp Asn Glu Val Lys Lys Leu Ile Arg
                165                 170                 175 gaa ata gat ata ggg gaa ata ccg gga gta gga gaa att act act caa      576
Glu Ile Asp Ile Gly Glu Ile Pro Gly Val Gly Glu Ile Thr Thr Gln
            180                 185                 190 aaa ctc aaa tca tta ggt ata aat aaa ctt ata gat att tta aac ttt      624
Lys Leu Lys Ser Leu Gly Ile Asn Lys Leu Ile Asp Ile Leu Asn Phe
        195                 200                 205 gat ttt atg aaa ata aag aaa att gta gga gaa gct aag gct aat tac      672
Asp Phe Met Lys Ile Lys Lys Ile Val Gly Glu Ala Lys Ala Asn Tyr
    210                 215                 220 tta ttc tcg tta gcg aga gat gaa tat ttt gga cca gtt aag gaa agg      720
Leu Phe Ser Leu Ala Arg Asp Glu Tyr Phe Gly Pro Val Lys Glu Arg
225                 230                 235                 240 gtt aga aag agt ata ggg agg ata gtt act tta aag aaa aat agt agg      768
Val Arg Lys Ser Ile Gly Arg Ile Val Thr Leu Lys Lys Asn Ser Arg
                245                 250                 255 aat ata gaa gaa att aaa cca ttc tta gct aga tca cta gat gaa gct      816
Asn Ile Glu Glu Ile Lys Pro Phe Leu Ala Arg Ser Leu Asp Glu Ala
            260                 265                 270 ttt aat aaa tta aat ggt aaa ata cct aaa aca att tat cta gta gca      864
Phe Asn Lys Leu Asn Gly Lys Ile Pro Lys Thr Ile Tyr Leu Val Ala
        275                 280                 285 gtt atg gaa gat ttg gat ata att agt aga ggt aag aca ttc cct cac      912
Val Met Glu Asp Leu Asp Ile Ile Ser Arg Gly Lys Thr Phe Pro His
    290                 295                 300 gga ata act aaa gag acc gca tat aaa gca tcc tta gaa tta ttg gaa      960
Gly Ile Thr Lys Glu Thr Ala Tyr Lys Ala Ser Leu Glu Leu Leu Glu
305                 310                 315                 320 aaa cta ttg gct gag gat aag agg aag ata aga aga ata gga gtt aga     1008
Lys Leu Leu Ala Glu Asp Lys Arg Lys Ile Arg Arg Ile Gly Val Arg
                325                 330                 335 ttt agt aaa ttt att gag gct act agt tta gac aag ttc ttc caa ttc     1056
Phe Ser Lys Phe Ile Glu Ala Thr Ser Leu Asp Lys Phe Phe Gln Phe
            340                 345                 350 taa                                                                  1059
```

<210> SEQ ID NO 14
<211> LENGTH: 352
<212> TYPE: PRT
<213> ORGANISM: Sulfolobus tengchongensis

<400> SEQUENCE: 14

```
Met Ile Ile Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
                20                  25                  30

Phe Ser Gly Arg Thr Glu Asn Ser Gly Ala Val Ala Thr Ala Asn Tyr
        35                  40                  45
```

Glu Ala Arg Lys Leu Gly Val Lys Ala Gly Met Pro Ile Val Lys Ala
    50                  55                  60

Lys Glu Ile Leu Pro Asp Ala Ile Tyr Leu Pro Met Arg Lys Glu Val
65                  70                  75                  80

Tyr Gln Gln Val Ser Asn Arg Ile Met Asn Ile Leu Arg Lys Tyr Ser
                85                  90                  95

Arg Lys Ile Glu Ile Ala Ser Ile Asp Glu Ala Tyr Leu Asp Ile Ser
            100                 105                 110

Asp Lys Val Asn Asn Tyr Thr Asp Ala Tyr Lys Ile Gly Leu Gln Ile
        115                 120                 125

Lys Asn Glu Ile Tyr Glu Lys Glu Lys Ile Thr Val Thr Val Gly Ile
    130                 135                 140

Ser Lys Asn Lys Val Phe Ala Lys Ile Ala Ala Glu Met Ala Lys Pro
145                 150                 155                 160

Asn Gly Ile Lys Val Ile Asp Asp Asn Glu Val Lys Lys Leu Ile Arg
                165                 170                 175

Glu Ile Asp Ile Gly Glu Ile Pro Gly Val Gly Glu Ile Thr Thr Gln
            180                 185                 190

Lys Leu Lys Ser Leu Gly Ile Asn Lys Leu Ile Asp Ile Leu Asn Phe
        195                 200                 205

Asp Phe Met Lys Ile Lys Lys Ile Val Gly Glu Ala Lys Ala Asn Tyr
    210                 215                 220

Leu Phe Ser Leu Ala Arg Asp Glu Tyr Phe Gly Pro Val Lys Glu Arg
225                 230                 235                 240

Val Arg Lys Ser Ile Gly Arg Ile Val Thr Leu Lys Lys Asn Ser Arg
                245                 250                 255

Asn Ile Glu Glu Ile Lys Pro Phe Leu Ala Arg Ser Leu Asp Glu Ala
            260                 265                 270

Phe Asn Lys Leu Asn Gly Lys Ile Pro Lys Thr Ile Tyr Leu Val Ala
        275                 280                 285

Val Met Glu Asp Leu Asp Ile Ile Ser Arg Gly Lys Thr Phe Pro His
    290                 295                 300

Gly Ile Thr Lys Glu Thr Ala Tyr Lys Ala Ser Leu Glu Leu Leu Glu
305                 310                 315                 320

Lys Leu Leu Ala Glu Asp Lys Arg Lys Ile Arg Arg Ile Gly Val Arg
                325                 330                 335

Phe Ser Lys Phe Ile Glu Ala Thr Ser Leu Asp Lys Phe Phe Gln Phe
            340                 345                 350

<210> SEQ ID NO 15
<211> LENGTH: 16
<212> TYPE: DNA
<213> ORGANISM: Artificial Sequence
<220> FEATURE:
<223> OTHER INFORMATION: Oligonucleotide primer/probe.

<400> SEQUENCE: 15
cttgaaaaca tagcga                                                     16

<210> SEQ ID NO 16
<211> LENGTH: 23
<212> TYPE: DNA
<213> ORGANISM: Artificial Sequence
<220> FEATURE:
<223> OTHER INFORMATION: Oligonucleotide primer/probe.

<400> SEQUENCE: 16

```
gcggtgtaga gacgagtgcg gag                                              23

<210> SEQ ID NO 17
<211> LENGTH: 50
<212> TYPE: DNA
<213> ORGANISM: Artificial Sequence
<220> FEATURE:
<223> OTHER INFORMATION: Oligonucleotide primer/probe.

<400> SEQUENCE: 17
ctctcacaag cagccaggca agctccgcac tcgtctctac accgctccgc                 50

<210> SEQ ID NO 18
<211> LENGTH: 50
<212> TYPE: DNA
<213> ORGANISM: Artificial Sequence
<220> FEATURE:
<223> OTHER INFORMATION: Oligonucleotide primer/probe.

<400> SEQUENCE: 18
ctctcacaag cagccaggca ttctccgcac tcgtctctac accgctccgc                 50

<210> SEQ ID NO 19
<211> LENGTH: 50
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (22)..(22)
<223> OTHER INFORMATION: n is an abasic site.

<400> SEQUENCE: 19
ctctcacaag cagccaggca tnctccgcac tcgtctctac accgctccgc                 50

<210> SEQ ID NO 20
<211> LENGTH: 20
<212> TYPE: DNA
<213> ORGANISM: Artificial Sequence
<220> FEATURE:
<223> OTHER INFORMATION: Oligonucleotide primer/probe.

<400> SEQUENCE: 20
gtgtcggggc gagtgcgccg                                                  20

<210> SEQ ID NO 21
<211> LENGTH: 44
<212> TYPE: DNA
<213> ORGANISM: Artificial Sequence
<220> FEATURE:
<223> OTHER INFORMATION: Oligonucleotide primer/probe.

<400> SEQUENCE: 21
ctctcacaag cagctaagca gcggcgcact cgccccgaca ccgc                       44

<210> SEQ ID NO 22
<211> LENGTH: 7
<212> TYPE: PRT
<213> ORGANISM: Artificial Sequence
<220> FEATURE:
<223> OTHER INFORMATION: Y-family polymerase consensus region.

<400> SEQUENCE: 22

Asp Thr Thr Gly Ala Gly Asp
1               5
```

```
<210> SEQ ID NO 23
<211> LENGTH: 30
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (15)..(27)
<223> OTHER INFORMATION: n is inosine

<400> SEQUENCE: 23
ccggaattcg ayacnacngg ngcnggngay                                  30

<210> SEQ ID NO 24
<211> LENGTH: 36
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (13)..(34)
<223> OTHER INFORMATION: n is inosine

<400> SEQUENCE: 24
gccgctcgag tcnadrwang cytcrtcnay nswnry                           36

<210> SEQ ID NO 25
<211> LENGTH: 7
<212> TYPE: PRT
<213> ORGANISM: Artificial Sequence
<220> FEATURE:
<223> OTHER INFORMATION: Y-family polymerase consensus region.

<400> SEQUENCE: 25

Tyr Glu Asp Val Glu Gly Gly
1               5

<210> SEQ ID NO 26
<211> LENGTH: 35
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (12)..(33)
<223> OTHER INFORMATION: n is inosine

<400> SEQUENCE: 26
ccggaattcr ynwsnrtnga ygargcntwy htnga                            35

<210> SEQ ID NO 27
<211> LENGTH: 30
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (22)..(28)
<223> OTHER INFORMATION: n is inosine

<400> SEQUENCE: 27
gccgctcgag taygargayg tngarggngg                                  30

<210> SEQ ID NO 28
```

```
<211> LENGTH: 30
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (15)..(27)
<223> OTHER INFORMATION: n is inosine

<400> SEQUENCE: 28
ccggaattcg ayacnacngg ngcnggngay                                30

<210> SEQ ID NO 29
<211> LENGTH: 36
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (13)..(34)
<223> OTHER INFORMATION: n is inosine

<400> SEQUENCE: 29
gccgctcgag tcnadrwang cytcrtcnay nswnry                         36

<210> SEQ ID NO 30
<211> LENGTH: 35
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (12)..(33)
<223> OTHER INFORMATION: n is inosine

<400> SEQUENCE: 30
ccggaattcr ynwsnrtnga ygargcntwy htnga                          35

<210> SEQ ID NO 31
<211> LENGTH: 30
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (22)..(28)
<223> OTHER INFORMATION: n is inosine

<400> SEQUENCE: 31
gccgctcgag taygargayg tngarggngg                                30

<210> SEQ ID NO 32
<211> LENGTH: 38
<212> TYPE: DNA
<213> ORGANISM: Artificial Sequence
<220> FEATURE:
<223> OTHER INFORMATION: Oligonucleotide primer/probe.

<400> SEQUENCE: 32
cgcggatcct taaatgtcga agaaatcaga taaatttg                       38

<210> SEQ ID NO 33
<211> LENGTH: 31
<212> TYPE: DNA
<213> ORGANISM: Artificial Sequence
```

```
<220> FEATURE:
<223> OTHER INFORMATION: Oligonucleotide primer/probe.

<400> SEQUENCE: 33
catgtcatga tagtgatatt cgttgatttt g                              31

<210> SEQ ID NO 34
<211> LENGTH: 34
<212> TYPE: DNA
<213> ORGANISM: Artificial Sequence
<220> FEATURE:
<223> OTHER INFORMATION: Oligonucleotide primer/probe.

<400> SEQUENCE: 34
ctcgtctctg gccagagaga tcaaatattt agcc                           34

<210> SEQ ID NO 35
<211> LENGTH: 35
<212> TYPE: DNA
<213> ORGANISM: Artificial Sequence
<220> FEATURE:
<223> OTHER INFORMATION: Oligonucleotide primer/probe.

<400> SEQUENCE: 35
ttgatctctc tggccagaga cgagtataac gagcc                          35

<210> SEQ ID NO 36
<211> LENGTH: 30
<212> TYPE: DNA
<213> ORGANISM: Artificial Sequence
<220> FEATURE:
<223> OTHER INFORMATION: Oligonucleotide primer/probe.

<400> SEQUENCE: 36 gggggggcata tgatagtgat attcgttgat                               30

<210> SEQ ID NO 37
<211> LENGTH: 42
<212> TYPE: DNA
<213> ORGANISM: Artificial Sequence
<220> FEATURE:
<223> OTHER INFORMATION: Oligonucleotide primer/probe.

<400> SEQUENCE: 37 gggggggattc ttggccaact ttagtagata taaggctaag gc                 42

<210> SEQ ID NO 38
<211> LENGTH: 27
<212> TYPE: DNA
<213> ORGANISM: Artificial Sequence
<220> FEATURE:
<223> OTHER INFORMATION: Oligonucleotide primer/probe.

<400> SEQUENCE: 38
gggaagttgg ccagaaataa atatagt                                   27

<210> SEQ ID NO 39
<211> LENGTH: 33
<212> TYPE: DNA
<213> ORGANISM: Artificial Sequence
<220> FEATURE:
<223> OTHER INFORMATION: Oligonucleotide primer/probe.

<400> SEQUENCE: 39 cccccggat ccttaaatgt cgaagaaatc aga                             33
```

<210> SEQ ID NO 40
<211> LENGTH: 2040
<212> TYPE: DNA
<213> ORGANISM: Thermoascus aurantiacus
<220> FEATURE:
<221> NAME/KEY: CDS
<222> LOCATION: (1)..(2040)

<400> SEQUENCE: 40

```
atg tcg cgc tcc tcc tct ccc tcc ccg cag cct ttc gtc cca tcg tcg      48
Met Ser Arg Ser Ser Ser Pro Ser Pro Gln Pro Phe Val Pro Ser Ser
1               5                   10                  15 att gat gat tcc acg aag cgg tcc cgc ttc acc tac cgt cac ctg cag      96
Ile Asp Asp Ser Thr Lys Arg Ser Arg Phe Thr Tyr Arg His Leu Gln
            20                  25                  30 ctc ctt cgc cag agt tcg acc tcg agc ccc ctc cgt gtg att gcc cat     144
Leu Leu Arg Gln Ser Ser Thr Ser Ser Pro Leu Arg Val Ile Ala His
        35                  40                  45 atc gat ctt gat gcc ttc tac gcg cag tgt gag atg gtg cgc ctg ggg     192
Ile Asp Leu Asp Ala Phe Tyr Ala Gln Cys Glu Met Val Arg Leu Gly
    50                  55                  60 gtc ccg cac acg acc ccg ctc gca gtc cag caa tgg gac tcg ctc att     240
Val Pro His Thr Thr Pro Leu Ala Val Gln Gln Trp Asp Ser Leu Ile
65                  70                  75                  80 gcg atc aac tac gct gcg cgt ccg ttt ggc gtg agc agg atg cta tcc     288
Ala Ile Asn Tyr Ala Ala Arg Pro Phe Gly Val Ser Arg Met Leu Ser
                85                  90                  95 gtg gct gag gcc aag aag cgc tgt ccc gaa ttg atc aca cag cat gtg     336
Val Ala Glu Ala Lys Lys Arg Cys Pro Glu Leu Ile Thr Gln His Val
            100                 105                 110 gcg acc ttc cgg gaa ggg gag ggt ggg aaa tgg gca tac cgg gat gat     384
Ala Thr Phe Arg Glu Gly Glu Gly Gly Lys Trp Ala Tyr Arg Asp Asp
        115                 120                 125 gcg gcc acg agc atc aag aca gat aag gtg tca ttg gat ccc tat cgg     432
Ala Ala Thr Ser Ile Lys Thr Asp Lys Val Ser Leu Asp Pro Tyr Arg
    130                 135                 140 gcc gaa tct agg aag atc ctg ggc gtg gta aag gag gaa ctg tct aga     480
Ala Glu Ser Arg Lys Ile Leu Gly Val Val Lys Glu Glu Leu Ser Arg
145                 150                 155                 160 tgg agg gag agt gta atg atg gat gtc gaa cga agt tca cag gtc cag     528
Trp Arg Glu Ser Val Met Met Asp Val Glu Arg Ser Ser Gln Val Gln
                165                 170                 175 gtg caa cct gcc aag ctg gag aag gcg agc atc gac gaa gtc ttt atc     576
Val Gln Pro Ala Lys Leu Glu Lys Ala Ser Ile Asp Glu Val Phe Ile
            180                 185                 190 gat ctg tcg tct ttg gtt ttt ggt gtc tta ctt cag cgg tat cct caa     624
Asp Leu Ser Ser Leu Val Phe Gly Val Leu Leu Gln Arg Tyr Pro Gln
        195                 200                 205 ctg cag aag gat ccc agt agt gaa gac aga ata gct gca ctg ccg ctt     672
Leu Gln Lys Asp Pro Ser Ser Glu Asp Arg Ile Ala Ala Leu Pro Leu
    210                 215                 220 cct ccg aga acg gca cta ggc tgg aac gca gaa gat gca ttg gta gac     720
Pro Pro Arg Thr Ala Leu Gly Trp Asn Ala Glu Asp Ala Leu Val Asp
225                 230                 235                 240 tta gat gaa aat gga tca gag gat gat gat cca gag tgg gat gac gtt     768
Leu Asp Glu Asn Gly Ser Glu Asp Asp Asp Pro Glu Trp Asp Asp Val
                245                 250                 255 gca gtg tcg ata ggc tca gag atc ata cgg tcc att cgc aag gct gtc     816
Ala Val Ser Ile Gly Ser Glu Ile Ile Arg Ser Ile Arg Lys Ala Val
            260                 265                 270
```

-continued

| | | |
|---|---|---|
| tgg gag caa ttg agc tat act tgc tct gca ggc att gca agg aac aag<br>Trp Glu Gln Leu Ser Tyr Thr Cys Ser Ala Gly Ile Ala Arg Asn Lys<br>275                   280                  285 | 864 |
| atg ata gcg aaa ctg ggg agc gcc tgc aac aag ccg aat aag cag act<br>Met Ile Ala Lys Leu Gly Ser Ala Cys Asn Lys Pro Asn Lys Gln Thr<br>290                     295                  300 | 912 |
| gtt gta cgg aat cgt gca gta cag aag ttt ctt agt gga tat aag ttc<br>Val Val Arg Asn Arg Ala Val Gln Lys Phe Leu Ser Gly Tyr Lys Phe<br>305                   310                 315              320 | 960 |
| acc aag att agg atg ctt gga ggg aaa ctg ggg gat caa gtt acc gcg<br>Thr Lys Ile Arg Met Leu Gly Gly Lys Leu Gly Asp Gln Val Thr Ala<br>                  325                  330              335 | 1008 |
| ttg ttt gga aca gaa caa gtg agt gag ctt ctg aag gtt ccc att gaa<br>Leu Phe Gly Thr Glu Gln Val Ser Glu Leu Leu Lys Val Pro Ile Glu<br>                    340                345              350 | 1056 |
| gag ctg aag gca aaa ttg gat gac ggt act gct gcc tgg ctg tac ggc<br>Glu Leu Lys Ala Lys Leu Asp Asp Gly Thr Ala Ala Trp Leu Tyr Gly<br>355                     360                  365 | 1104 |
| att atc cgc gga gag gat cat agc gag gtc aat ccc agg acg cag atc<br>Ile Ile Arg Gly Glu Asp His Ser Glu Val Asn Pro Arg Thr Gln Ile<br>370                   375                 380 | 1152 |
| aaa tcc atg ctc tca gca aag tct ttc cgg ccg agt atc aac tct gcc<br>Lys Ser Met Leu Ser Ala Lys Ser Phe Arg Pro Ser Ile Asn Ser Ala<br>385                   390                 395              400 | 1200 |
| gaa cag gca gaa aag tgg ctg cga att ttc gcg gcc gac atc tac ggg<br>Glu Gln Ala Glu Lys Trp Leu Arg Ile Phe Ala Ala Asp Ile Tyr Gly<br>                    405                410              415 | 1248 |
| cgc cta gtt gag gat ggt gtc ctt gga aat agg cgc cgt cca aag acg<br>Arg Leu Val Glu Asp Gly Val Leu Gly Asn Arg Arg Arg Pro Lys Thr<br>                    420                425              430 | 1296 |
| att act ttg cac cac aga tat gga gat caa gtg cga tcc cgt cag ata<br>Ile Thr Leu His His Arg Tyr Gly Asp Gln Val Arg Ser Arg Gln Ile<br>435                     440                 445 | 1344 |
| cct ata cct gga gga aaa ccc att gat gaa ttg ctc ctc ttt gag ctc<br>Pro Ile Pro Gly Gly Lys Pro Ile Asp Glu Leu Leu Leu Phe Glu Leu<br>450                   455                 460 | 1392 |
| gcc aaa act ctc ctc ggg caa gtg atc gct gat ggg cga gta tgg cct<br>Ala Lys Thr Leu Leu Gly Gln Val Ile Ala Asp Gly Arg Val Trp Pro<br>465                   470                 475              480 | 1440 |
| tgc gcg aac ttg tcg ctc agc gta ggt ggt ttt gaa gac ggt atc acg<br>Cys Ala Asn Leu Ser Leu Ser Val Gly Gly Phe Glu Asp Gly Ile Thr<br>                    485                490              495 | 1488 |
| aat aat cga gca atc gac ggt ttc ctc ata cga gga gat gaa gct aaa<br>Asn Asn Arg Ala Ile Asp Gly Phe Leu Ile Arg Gly Asp Glu Ala Lys<br>                  500                505              510 | 1536 |
| tcc atg aat act cca gtc agg ggt cct gat acc tcc ggt aat cag gaa<br>Ser Met Asn Thr Pro Val Arg Gly Pro Asp Thr Ser Gly Asn Gln Glu<br>515                     520                 525 | 1584 |
| gac gga caa aga gta gag aag aga agg aag atc gag ggc ata gag cgt<br>Asp Gly Gln Arg Val Glu Lys Arg Arg Lys Ile Glu Gly Ile Glu Arg<br>530                   535                 540 | 1632 |
| ttc ttt acg aag gcg act tct aat cca gat gta gag tcc gca act gac<br>Phe Phe Thr Lys Ala Thr Ser Asn Pro Asp Val Glu Ser Ala Thr Asp<br>545                   550                 555              560 | 1680 |
| caa cag aac ctg aat aat tcg gaa ttg gaa gac gtt tcc agg caa ttg<br>Gln Gln Asn Leu Asn Asn Ser Glu Leu Glu Asp Val Ser Arg Gln Leu<br>                    565                570              575 | 1728 |
| aac gaa tat ggg gat gaa aac gta cat gga gaa cag gct gtt cca gac<br>Asn Glu Tyr Gly Asp Glu Asn Val His Gly Glu Gln Ala Val Pro Asp<br>                  580                585              590 | 1776 |

```
tac ccg cta gat caa gat act tct tgg gtc tgc aat cga tgc gga aag      1824
Tyr Pro Leu Asp Gln Asp Thr Ser Trp Val Cys Asn Arg Cys Gly Lys
        595                 600                 605 tcc ttt cct gag ttt gag agg atc gaa cac gaa gac tgg cac ttt gcc      1872
Ser Phe Pro Glu Phe Glu Arg Ile Glu His Glu Asp Trp His Phe Ala
    610                 615                 620 aaa gat ctt gag agc caa gaa agg caa gcc gcc agg gct tcc cag aac      1920
Lys Asp Leu Glu Ser Gln Glu Arg Gln Ala Ala Arg Ala Ser Gln Asn
625                 630                 635                 640 ata caa agc gct aca tcg cat ttt tcg agc gtt cca ggg aag cgg aaa      1968
Ile Gln Ser Ala Thr Ser His Phe Ser Ser Val Pro Gly Lys Arg Lys
                645                 650                 655 gct ggt agt gta ggt ggt ggg cgg ggt cat ggg aga cca gaa aag ggg      2016
Ala Gly Ser Val Gly Gly Gly Arg Gly His Gly Arg Pro Glu Lys Gly
            660                 665                 670 cag acg cgg ctt acc ttt gga tga                                      2040
Gln Thr Arg Leu Thr Phe Gly
        675

<210> SEQ ID NO 41
<211> LENGTH: 679
<212> TYPE: PRT
<213> ORGANISM: Thermoascus aurantiacus

<400> SEQUENCE: 41

Met Ser Arg Ser Ser Pro Ser Pro Gln Pro Phe Val Pro Ser Ser
1               5                   10                  15

Ile Asp Asp Ser Thr Lys Arg Ser Arg Phe Thr Tyr Arg His Leu Gln
            20                  25                  30

Leu Leu Arg Gln Ser Ser Thr Ser Ser Pro Leu Arg Val Ile Ala His
        35                  40                  45

Ile Asp Leu Asp Ala Phe Tyr Ala Gln Cys Glu Met Val Arg Leu Gly
    50                  55                  60

Val Pro His Thr Thr Pro Leu Ala Val Gln Gln Trp Asp Ser Leu Ile
65                  70                  75                  80

Ala Ile Asn Tyr Ala Ala Arg Pro Phe Gly Val Ser Arg Met Leu Ser
                85                  90                  95

Val Ala Glu Ala Lys Lys Arg Cys Pro Glu Leu Ile Thr Gln His Val
            100                 105                 110

Ala Thr Phe Arg Glu Gly Glu Gly Gly Lys Trp Ala Tyr Arg Asp Asp
        115                 120                 125

Ala Ala Thr Ser Ile Lys Thr Asp Lys Val Ser Leu Asp Pro Tyr Arg
    130                 135                 140

Ala Glu Ser Arg Lys Ile Leu Gly Val Val Lys Glu Glu Leu Ser Arg
145                 150                 155                 160

Trp Arg Glu Ser Val Met Met Asp Val Glu Arg Ser Ser Gln Val Gln
                165                 170                 175

Val Gln Pro Ala Lys Leu Glu Lys Ala Ser Ile Asp Glu Val Phe Ile
            180                 185                 190

Asp Leu Ser Ser Leu Val Phe Gly Val Leu Leu Gln Arg Tyr Pro Gln
        195                 200                 205

Leu Gln Lys Asp Pro Ser Ser Glu Asp Arg Ile Ala Ala Leu Pro Leu
    210                 215                 220

Pro Pro Arg Thr Ala Leu Gly Trp Asn Ala Glu Asp Ala Leu Val Asp
225                 230                 235                 240

Leu Asp Glu Asn Gly Ser Glu Asp Asp Pro Glu Trp Asp Asp Val
```

```
                        245                 250                 255
Ala Val Ser Ile Gly Ser Glu Ile Ile Arg Ser Ile Arg Lys Ala Val
            260                 265                 270

Trp Glu Gln Leu Ser Tyr Thr Cys Ser Ala Gly Ile Ala Arg Asn Lys
            275                 280                 285

Met Ile Ala Lys Leu Gly Ser Ala Cys Asn Lys Pro Asn Lys Gln Thr
            290                 295                 300

Val Val Arg Asn Arg Ala Val Gln Lys Phe Leu Ser Gly Tyr Lys Phe
305                 310                 315                 320

Thr Lys Ile Arg Met Leu Gly Lys Leu Gly Asp Gln Val Thr Ala
                325                 330                 335

Leu Phe Gly Thr Glu Gln Val Ser Glu Leu Leu Lys Val Pro Ile Glu
            340                 345                 350

Glu Leu Lys Ala Lys Leu Asp Asp Gly Thr Ala Ala Trp Leu Tyr Gly
            355                 360                 365

Ile Ile Arg Gly Glu Asp His Ser Glu Val Asn Pro Arg Thr Gln Ile
            370                 375                 380

Lys Ser Met Leu Ser Ala Lys Ser Phe Arg Pro Ser Ile Asn Ser Ala
385                 390                 395                 400

Glu Gln Ala Glu Lys Trp Leu Arg Ile Phe Ala Ala Asp Ile Tyr Gly
            405                 410                 415

Arg Leu Val Glu Asp Gly Val Leu Gly Asn Arg Arg Pro Lys Thr
            420                 425                 430

Ile Thr Leu His His Arg Tyr Gly Asp Gln Val Arg Ser Arg Gln Ile
            435                 440                 445

Pro Ile Pro Gly Gly Lys Pro Ile Asp Glu Leu Leu Leu Phe Glu Leu
450                 455                 460

Ala Lys Thr Leu Leu Gly Gln Val Ile Ala Asp Gly Arg Val Trp Pro
465                 470                 475                 480

Cys Ala Asn Leu Ser Leu Ser Val Gly Gly Phe Glu Asp Gly Ile Thr
                485                 490                 495

Asn Asn Arg Ala Ile Asp Gly Phe Leu Ile Arg Gly Asp Glu Ala Lys
            500                 505                 510

Ser Met Asn Thr Pro Val Arg Gly Pro Asp Thr Ser Gly Asn Gln Glu
            515                 520                 525

Asp Gly Gln Arg Val Glu Lys Arg Lys Ile Glu Gly Ile Glu Arg
            530                 535                 540

Phe Phe Thr Lys Ala Thr Ser Asn Pro Asp Val Glu Ser Ala Thr Asp
545                 550                 555                 560

Gln Gln Asn Leu Asn Asn Ser Glu Leu Glu Asp Val Ser Arg Gln Leu
                565                 570                 575

Asn Glu Tyr Gly Asp Glu Asn Val His Gly Glu Gln Ala Val Pro Asp
            580                 585                 590

Tyr Pro Leu Asp Gln Asp Thr Ser Trp Val Cys Asn Arg Cys Gly Lys
            595                 600                 605

Ser Phe Pro Glu Phe Glu Arg Ile Glu His Glu Asp Trp His Phe Ala
            610                 615                 620

Lys Asp Leu Glu Ser Gln Glu Arg Gln Ala Arg Ala Ser Gln Asn
625                 630                 635                 640

Ile Gln Ser Ala Thr Ser His Phe Ser Val Pro Gly Lys Arg Lys
                645                 650                 655

Ala Gly Ser Val Gly Gly Gly Arg Gly His Gly Arg Pro Glu Lys Gly
            660                 665                 670
```

Gln Thr Arg Leu Thr Phe Gly
        675

<210> SEQ ID NO 42
<211> LENGTH: 1914
<212> TYPE: DNA
<213> ORGANISM: Thermomyces lanuginosus
<220> FEATURE:
<221> NAME/KEY: CDS
<222> LOCATION: (1)..(1914)

<400> SEQUENCE: 42

```
atg tcc tcg acc tct tcc ccg agt tat atc aag tcg tcc tct cta gac      48
Met Ser Ser Thr Ser Ser Pro Ser Tyr Ile Lys Ser Ser Ser Leu Asp
1               5                   10                  15 aga gac ttc aag caa tcg cga ttc aca tat cga cat ctt caa ctc cct      96
Arg Asp Phe Lys Gln Ser Arg Phe Thr Tyr Arg His Leu Gln Leu Pro
                20                  25                  30 gcc caa aat gtg ccc ttg agt ccc ttg aga gta gtt gcg cat atc gac     144
Ala Gln Asn Val Pro Leu Ser Pro Leu Arg Val Val Ala His Ile Asp
            35                  40                  45 ttg gat gcg ttt tat gca caa tgt gag atg gtg cgc ttg gga gtc tcc     192
Leu Asp Ala Phe Tyr Ala Gln Cys Glu Met Val Arg Leu Gly Val Ser
    50                  55                  60 cgc gag act cca ctc gct gtg caa caa tgg gac gcc ctg att gcc gtt     240
Arg Glu Thr Pro Leu Ala Val Gln Gln Trp Asp Ala Leu Ile Ala Val
65                  70                  75                  80 aat tac gcg gcg cga cca ttc ggc atc tcg cgt atg ata tcc gtc gct     288
Asn Tyr Ala Ala Arg Pro Phe Gly Ile Ser Arg Met Ile Ser Val Ala
                85                  90                  95 gaa gcg aag aaa aga tgt ccc aat ctt att cta caa cat gtt gca act     336
Glu Ala Lys Lys Arg Cys Pro Asn Leu Ile Leu Gln His Val Ala Thr
                100                 105                 110 ttt cgg gaa gga gag ggt ggt cga tgg gcg tat cgc gaa gac gcc gcg     384
Phe Arg Glu Gly Glu Gly Gly Arg Trp Ala Tyr Arg Glu Asp Ala Ala
            115                 120                 125 cag aat atc ggg acc gac aag gtg tcg ctg gat ccg tac cgg aaa gag     432
Gln Asn Ile Gly Thr Asp Lys Val Ser Leu Asp Pro Tyr Arg Lys Glu
    130                 135                 140 tcc cga aaa atc ctt ggt ctc att cac gac gaa ctc tcg aag tgg agg     480
Ser Arg Lys Ile Leu Gly Leu Ile His Asp Glu Leu Ser Lys Trp Arg
145                 150                 155                 160 gat ctc cta acg tct tca gat tct cgt gat ggg aat ctt cag ccg gcg     528
Asp Leu Leu Thr Ser Ser Asp Ser Arg Asp Gly Asn Leu Gln Pro Ala
                165                 170                 175 aag gtt gag aaa gct tcg gtc gat gag gta ttc atc gat ttg tct tcc     576
Lys Val Glu Lys Ala Ser Val Asp Glu Val Phe Ile Asp Leu Ser Ser
                180                 185                 190 att gtc tat gga gtt ctg cgc gat cga tat gct gaa ctg agg aac att     624
Ile Val Tyr Gly Val Leu Arg Asp Arg Tyr Ala Glu Leu Arg Asn Ile
            195                 200                 205 tct tca ata gag gat aag tcg aag cca ctt cct ccg ctg cca aca acc     672
Ser Ser Ile Glu Asp Lys Ser Lys Pro Leu Pro Pro Leu Pro Thr Thr
    210                 215                 220 gtt cta gaa tgg tca ccg gag gat ggc tta gtg gac tta gac aag gca     720
Val Leu Glu Trp Ser Pro Glu Asp Gly Leu Val Asp Leu Asp Lys Ala
225                 230                 235                 240 gaa atg gag gag gac aac cct gat tgg gac gac atg gca atg ctg ata     768
Glu Met Glu Glu Asp Asn Pro Asp Trp Asp Asp Met Ala Met Leu Ile
                245                 250                 255
```

```
gga gcg gag gtt atc cgt tct gtt cgg gaa gcg ata tac gcc aag ttg    816
Gly Ala Glu Val Ile Arg Ser Val Arg Glu Ala Ile Tyr Ala Lys Leu
        260                 265                 270 ggc tac act tgc tct gcc gga atc tcc agg aac aag atg ata gcc aag    864
Gly Tyr Thr Cys Ser Ala Gly Ile Ser Arg Asn Lys Met Ile Ala Lys
            275                 280                 285 cta ggc agt ggg cga aac aag cct aac aaa cag acc att gtc cgc aac    912
Leu Gly Ser Gly Arg Asn Lys Pro Asn Lys Gln Thr Ile Val Arg Asn
    290                 295                 300 cgg gct atc caa aat ttc ctc agt caa ttc aag ttt acc cag ata cgg    960
Arg Ala Ile Gln Asn Phe Leu Ser Gln Phe Lys Phe Thr Gln Ile Arg
305                 310                 315                 320 atg ctt ggg gga aag ctt ggt gat cag gtc tct tcg cac ttt gga acc   1008
Met Leu Gly Gly Lys Leu Gly Asp Gln Val Ser Ser His Phe Gly Thr
                325                 330                 335 gac caa gtt acc gag ttg ctc aag gtg ccc ctg gag caa ttc aaa gca   1056
Asp Gln Val Thr Glu Leu Leu Lys Val Pro Leu Glu Gln Phe Lys Ala
            340                 345                 350 aag ttc gat gat gac act gcc att tgg ctc tat ggg atc att cgc ggc   1104
Lys Phe Asp Asp Asp Thr Ala Ile Trp Leu Tyr Gly Ile Ile Arg Gly
    355                 360                 365 gtg gac cac agt gaa gtt aat act cgg act caa atc aag tcc atg ctt   1152
Val Asp His Ser Glu Val Asn Thr Arg Thr Gln Ile Lys Ser Met Leu
370                 375                 380 tcg gcc aag tca ttt aca cgc aac atc agt tct gtt gac caa gcc gag   1200
Ser Ala Lys Ser Phe Thr Arg Asn Ile Ser Ser Val Asp Gln Ala Glu
385                 390                 395                 400 aaa tgg cta cga ata ttt gct gct gac ctc tat ggc cga ctt gta gga   1248
Lys Trp Leu Arg Ile Phe Ala Ala Asp Leu Tyr Gly Arg Leu Val Gly
                405                 410                 415 gat ggc atc ctc gag cat aga cgt cgc ccc aag acc atc act ctt cac   1296
Asp Gly Ile Leu Glu His Arg Arg Arg Pro Lys Thr Ile Thr Leu His
            420                 425                 430 aat cgc tcg cgc tct gag aca cat tca aaa cag ctg ccg att ccc ggc   1344
Asn Arg Ser Arg Ser Glu Thr His Ser Lys Gln Leu Pro Ile Pro Gly
    435                 440                 445 ggg aag acc att gat gaa gat ctt ttg ttt gat ctt gcg cgg act ttg   1392
Gly Lys Thr Ile Asp Glu Asp Leu Leu Phe Asp Leu Ala Arg Thr Leu
450                 455                 460 ctc gca caa att ata agc gag ggg cgt gca tgg cca agt cag cac ctt   1440
Leu Ala Gln Ile Ile Ser Glu Gly Arg Ala Trp Pro Ser Gln His Leu
465                 470                 475                 480 tcg ctc agc gta agt ggc ttc gag gaa ggg ccg acc aac aat cgg gcc   1488
Ser Leu Ser Val Ser Gly Phe Glu Glu Gly Pro Thr Asn Asn Arg Ala
                485                 490                 495 att gat ggc ttt ctg gtg cga ggt cca gcg gcg ctc gag ttg aat acg   1536
Ile Asp Gly Phe Leu Val Arg Gly Pro Ala Ala Leu Glu Leu Asn Thr
            500                 505                 510 ttg aat gcc caa aat cgc gat tct gag agt gga aga agt ccc gga gaa   1584
Leu Asn Ala Gln Asn Arg Asp Ser Glu Ser Gly Arg Ser Pro Gly Glu
    515                 520                 525 tca ggg aag aaa aga aag gcg gat gac ggg gca cta caa aga tat ttc   1632
Ser Gly Lys Lys Arg Lys Ala Asp Asp Gly Ala Leu Gln Arg Tyr Phe
530                 535                 540 aaa aag agc gtg ccg agg gac agc agt aca ccg caa cca gag act gag   1680
Lys Lys Ser Val Pro Arg Asp Ser Ser Thr Pro Gln Pro Glu Thr Glu
545                 550                 555                 560 ccc gac gtt gcc ggc tac caa tgc cct cga tgc aat aaa ctc atg ccc   1728
Pro Asp Val Ala Gly Tyr Gln Cys Pro Arg Cys Asn Lys Leu Met Pro
                565                 570                 575
```

```
gaa gac gaa cgg ggc gaa cat gag gat tgg cat ttt gcc aaa gac tta      1776
Glu Asp Glu Arg Gly Glu His Glu Asp Trp His Phe Ala Lys Asp Leu
            580                 585                 590 tcg atg caa gac atg caa ggg gca act gca atc ttc gct gtc aaa ccc      1824
Ser Met Gln Asp Met Gln Gly Ala Thr Ala Ile Phe Ala Val Lys Pro
        595                 600                 605 aag cat tac acg agc ctg cgg caa gaa tac cac ggc cgg cgc gga tct      1872
Lys His Tyr Thr Ser Leu Arg Gln Glu Tyr His Gly Arg Arg Gly Ser
    610                 615                 620 ggc aag ccc gaa cta aag caa aca cgc ctg acg ttc aaa tga              1914
Gly Lys Pro Glu Leu Lys Gln Thr Arg Leu Thr Phe Lys
625                 630                 635

<210> SEQ ID NO 43
<211> LENGTH: 637
<212> TYPE: PRT
<213> ORGANISM: Thermomyces lanuginosus

<400> SEQUENCE: 43

Met Ser Ser Thr Ser Pro Ser Tyr Ile Lys Ser Ser Leu Asp
1               5                   10                  15

Arg Asp Phe Lys Gln Ser Arg Phe Thr Tyr Arg His Leu Gln Leu Pro
                20                  25                  30

Ala Gln Asn Val Pro Leu Ser Pro Leu Arg Val Val Ala His Ile Asp
            35                  40                  45

Leu Asp Ala Phe Tyr Ala Gln Cys Glu Met Val Arg Leu Gly Val Ser
        50                  55                  60

Arg Glu Thr Pro Leu Ala Val Gln Gln Trp Asp Ala Leu Ile Ala Val
65                  70                  75                  80

Asn Tyr Ala Ala Arg Pro Phe Gly Ile Ser Arg Met Ile Ser Val Ala
                85                  90                  95

Glu Ala Lys Lys Arg Cys Pro Asn Leu Ile Leu Gln His Val Ala Thr
            100                 105                 110

Phe Arg Glu Gly Glu Gly Gly Arg Trp Ala Tyr Arg Glu Asp Ala Ala
        115                 120                 125

Gln Asn Ile Gly Thr Asp Lys Val Ser Leu Asp Pro Tyr Arg Lys Glu
    130                 135                 140

Ser Arg Lys Ile Leu Gly Leu Ile His Asp Glu Leu Ser Lys Trp Arg
145                 150                 155                 160

Asp Leu Leu Thr Ser Ser Asp Ser Arg Asp Gly Asn Leu Gln Pro Ala
                165                 170                 175

Lys Val Glu Lys Ala Ser Val Asp Glu Val Phe Ile Asp Leu Ser Ser
            180                 185                 190

Ile Val Tyr Gly Val Leu Arg Asp Arg Tyr Ala Glu Leu Arg Asn Ile
        195                 200                 205

Ser Ser Ile Glu Asp Lys Ser Lys Pro Leu Pro Pro Leu Pro Thr Thr
    210                 215                 220

Val Leu Glu Trp Ser Pro Glu Asp Gly Leu Val Asp Leu Asp Lys Ala
225                 230                 235                 240

Glu Met Glu Glu Asp Asn Pro Asp Trp Asp Asp Met Ala Met Leu Ile
                245                 250                 255

Gly Ala Glu Val Ile Arg Ser Val Arg Glu Ala Ile Tyr Ala Lys Leu
            260                 265                 270

Gly Tyr Thr Cys Ser Ala Gly Ile Ser Arg Asn Lys Met Ile Ala Lys
        275                 280                 285
```

```
Leu Gly Ser Gly Arg Asn Lys Pro Asn Lys Gln Thr Ile Val Arg Asn
            290                 295                 300

Arg Ala Ile Gln Asn Phe Leu Ser Gln Phe Lys Phe Thr Gln Ile Arg
305                 310                 315                 320

Met Leu Gly Gly Lys Leu Gly Asp Gln Val Ser Ser His Phe Gly Thr
                325                 330                 335

Asp Gln Val Thr Glu Leu Leu Lys Val Pro Leu Glu Gln Phe Lys Ala
            340                 345                 350

Lys Phe Asp Asp Thr Ala Ile Trp Leu Tyr Gly Ile Ile Arg Gly
                355                 360                 365

Val Asp His Ser Glu Val Asn Thr Arg Thr Gln Ile Lys Ser Met Leu
            370                 375                 380

Ser Ala Lys Ser Phe Thr Arg Asn Ile Ser Ser Val Asp Gln Ala Glu
385                 390                 395                 400

Lys Trp Leu Arg Ile Phe Ala Ala Asp Leu Tyr Gly Arg Leu Val Gly
                405                 410                 415

Asp Gly Ile Leu Glu His Arg Arg Pro Lys Thr Ile Thr Leu His
            420                 425                 430

Asn Arg Ser Arg Ser Glu Thr His Ser Lys Gln Leu Pro Ile Pro Gly
            435                 440                 445

Gly Lys Thr Ile Asp Glu Asp Leu Leu Phe Asp Leu Ala Arg Thr Leu
450                 455                 460

Leu Ala Gln Ile Ile Ser Glu Gly Arg Ala Trp Pro Ser Gln His Leu
465                 470                 475                 480

Ser Leu Ser Val Ser Gly Phe Glu Glu Gly Pro Thr Asn Asn Arg Ala
                485                 490                 495

Ile Asp Gly Phe Leu Val Arg Gly Pro Ala Ala Leu Glu Leu Asn Thr
            500                 505                 510

Leu Asn Ala Gln Asn Arg Asp Ser Glu Ser Gly Arg Ser Pro Gly Glu
            515                 520                 525

Ser Gly Lys Lys Arg Lys Ala Asp Asp Gly Ala Leu Gln Arg Tyr Phe
530                 535                 540

Lys Lys Ser Val Pro Arg Asp Ser Ser Thr Pro Gln Pro Glu Thr Glu
545                 550                 555                 560

Pro Asp Val Ala Gly Tyr Gln Cys Pro Arg Cys Asn Lys Leu Met Pro
                565                 570                 575

Glu Asp Glu Arg Gly Glu His Glu Asp Trp His Phe Ala Lys Asp Leu
            580                 585                 590

Ser Met Gln Asp Met Gln Gly Ala Thr Ala Ile Phe Ala Val Lys Pro
            595                 600                 605

Lys His Tyr Thr Ser Leu Arg Gln Glu Tyr His Gly Arg Arg Gly Ser
            610                 615                 620

Gly Lys Pro Glu Leu Lys Gln Thr Arg Leu Thr Phe Lys
625                 630                 635

<210> SEQ ID NO 44
<211> LENGTH: 1460
<212> TYPE: DNA
<213> ORGANISM: Thermomyces lanuginosus
<220> FEATURE:
<221> NAME/KEY: CDS
<222> LOCATION: (2)..(1459)

<400> SEQUENCE: 44 c atc atc cac ttt gat tat gat tgc ttc tat gca tcc gta ttg gag gca      49
  Ile Ile His Phe Asp Tyr Asp Cys Phe Tyr Ala Ser Val Leu Glu Ala
```

```
                1                  5                      10                      15
        gag aac ccg gcg ctc aag tcg ctg cct ctg gcc atc cag cag aag caa         97
        Glu Asn Pro Ala Leu Lys Ser Leu Pro Leu Ala Ile Gln Gln Lys Gln
                        20                  25                  30 atc atc gtc acc tgc aac tat gaa gcc cgg cgg cgc ggc ctg agg aag        145
        Ile Ile Val Thr Cys Asn Tyr Glu Ala Arg Arg Arg Gly Leu Arg Lys
                        35                  40                  45 ctc cag ctc gtc aag gaa gcc aag aag att tgt cca gac gtc gtc atc        193
        Leu Gln Leu Val Lys Glu Ala Lys Lys Ile Cys Pro Asp Val Val Ile
                50                  55                  60 atc ctg ggc gaa gat ttg acc aag ttt cgc gat gcc tcc aag agc ctg        241
        Ile Leu Gly Glu Asp Leu Thr Lys Phe Arg Asp Ala Ser Lys Ser Leu
        65                  70                  75                  80 tac gct tat ctg cgc ggc ttt ctg tgg ggt tct aag att gaa agg ctt        289
        Tyr Ala Tyr Leu Arg Gly Phe Leu Trp Gly Ser Lys Ile Glu Arg Leu
                        85                  90                  95 ggc ttt gac gag gtg ttt ctt gac gtc act gat atg ata gac tac aat        337
        Gly Phe Asp Glu Val Phe Leu Asp Val Thr Asp Met Ile Asp Tyr Asn
                        100                 105                 110 gtc gcg ctg ctg agc cac cat gac ttg cag cat tca ttc ttc tgc ttg        385
        Val Ala Leu Leu Ser His His Asp Leu Gln His Ser Phe Phe Cys Leu
                        115                 120                 125 gat agg gag gac cca acc aag ggc ttc gag ttt gac gcg act cgg tac        433
        Asp Arg Glu Asp Pro Thr Lys Gly Phe Glu Phe Asp Ala Thr Arg Tyr
                130                 135                 140 tgc ggt cct acg tat ccg cca tcg ccg gat gcc act ggc gtc gac ctt        481
        Cys Gly Pro Thr Tyr Pro Pro Ser Pro Asp Ala Thr Gly Val Asp Leu
        145                 150                 155                 160 tct gat ccg ttg agt cgg cgt ctt atc ctg ggc tca cat ctg gcc ttc        529
        Ser Asp Pro Leu Ser Arg Arg Leu Ile Leu Gly Ser His Leu Ala Phe
                        165                 170                 175 cac atg cgt atg cga cta gat gcc gag cgg ggt tac acg gcc acc gta        577
        His Met Arg Met Arg Leu Asp Ala Glu Arg Gly Tyr Thr Ala Thr Val
                        180                 185                 190 gga gtg tcc acg aac aag ttg ctg gcc aag ctc gtc ggc agc gtg aac        625
        Gly Val Ser Thr Asn Lys Leu Leu Ala Lys Leu Val Gly Ser Val Asn
                        195                 200                 205 aaa cca aac aac caa aca acg ctg att cca ccg tat tcc gta gac aga        673
        Lys Pro Asn Asn Gln Thr Thr Leu Ile Pro Pro Tyr Ser Val Asp Arg
                210                 215                 220 gat gac gag ggt tgc agc agt aat gtg acc aag ctt atg gac tct cac        721
        Asp Asp Glu Gly Cys Ser Ser Asn Val Thr Lys Leu Met Asp Ser His
        225                 230                 235                 240 gag ctt ggc aaa gtg ccc ggg atc ggg ttc aag acg gcg cag aaa ctg        769
        Glu Leu Gly Lys Val Pro Gly Ile Gly Phe Lys Thr Ala Gln Lys Leu
                        245                 250                 255 cgc acg cat gtt ctc ggc cgt gaa cca aca ttc cag ccc tat gtt gag        817
        Arg Thr His Val Leu Gly Arg Glu Pro Thr Phe Gln Pro Tyr Val Glu
                        260                 265                 270 cgc agt caa gat gcc cag gtc act gtt cga gac gtg cgg cag ttt cca        865
        Arg Ser Gln Asp Ala Gln Val Thr Val Arg Asp Val Arg Gln Phe Pro
                        275                 280                 285 gga atg ggc ccg gct atg ctg acc tca att ctc gtt ggg cct ggc acc        913
        Gly Met Gly Pro Ala Met Leu Thr Ser Ile Leu Val Gly Pro Gly Thr
                290                 295                 300 gct aaa gat att gga gtt cgg gta tgg gaa ctg ctc cac gga gtg gat        961
        Ala Lys Asp Ile Gly Val Arg Val Trp Glu Leu Leu His Gly Val Asp
        305                 310                 315                 320 aat tct gag gtt ctc gaa gcg aga acc att ccc act caa atc agc atc       1009
```

```
                                                               -continued

Asn Ser Glu Val Leu Glu Ala Arg Thr Ile Pro Thr Gln Ile Ser Ile
            325                 330                 335 gag gac tcc tac aag gga tca ccc cac aac gat gca gtc agg agg gaa      1057
Glu Asp Ser Tyr Lys Gly Ser Pro His Asn Asp Ala Val Arg Arg Glu
            340                 345                 350 ctc tgt cac ctc gcc gcc agc ctg atc cgg cgt atg cgt gcc gac ctg      1105
Leu Cys His Leu Ala Ala Ser Leu Ile Arg Arg Met Arg Ala Asp Leu
            355                 360                 365 aca aag atg gac gag acg gga tcg gga cgg cta cgc tgg ctc gcc cgt      1153
Thr Lys Met Asp Glu Thr Gly Ser Gly Arg Leu Arg Trp Leu Ala Arg
    370                 375                 380 ccc cgt acc gtc cga ctc tct aca cgg ctc cgg tcg ccc aaa atg cct      1201
Pro Arg Thr Val Arg Leu Ser Thr Arg Leu Arg Ser Pro Lys Met Pro
385                 390                 395                 400 gat ggc tca cgg aac tac agc ttc atg aat cgg cgt gtg tca cgc tct      1249
Asp Gly Ser Arg Asn Tyr Ser Phe Met Asn Arg Arg Val Ser Arg Ser
                405                 410                 415 ggc cca gca cct tcc atc ttc tct ctc gat gac gac atc gac gct          1297
Gly Pro Ala Pro Ser Phe Ile Phe Ser Leu Asp Asp Asp Ile Asp Ala
            420                 425                 430 ctc gcg act cgt ctt gtg gat gaa ctg ctt ctg tca atg ttc cgc cgg      1345
Leu Ala Thr Arg Leu Val Asp Glu Leu Leu Leu Ser Met Phe Arg Arg
            435                 440                 445 tcg ttc ccg gcg cga tcc ctg gag gaa ttg gcc ctg atc aac gtc gca      1393
Ser Phe Pro Ala Arg Ser Leu Glu Glu Leu Ala Leu Ile Asn Val Ala
450                 455                 460 gtg acc aat atg acg gac gcc gag ccg aag caa aac cgc ggg ccg caa      1441
Val Thr Asn Met Thr Asp Ala Glu Pro Lys Gln Asn Arg Gly Pro Gln
465                 470                 475                 480 cat cgc caa cat gct cga g                                             1460
His Arg Gln His Ala Arg
            485

<210> SEQ ID NO 45
<211> LENGTH: 486
<212> TYPE: PRT
<213> ORGANISM: Thermomyces lanuginosus

<400> SEQUENCE: 45

Ile Ile His Phe Asp Tyr Asp Cys Phe Tyr Ala Ser Val Leu Glu Ala
1               5                   10                  15

Glu Asn Pro Ala Leu Lys Ser Leu Pro Leu Ala Ile Gln Gln Lys Gln
            20                  25                  30

Ile Ile Val Thr Cys Asn Tyr Glu Ala Arg Arg Gly Leu Arg Lys
            35                  40                  45

Leu Gln Leu Val Lys Glu Ala Lys Lys Ile Cys Pro Asp Val Val Ile
    50                  55                  60

Ile Leu Gly Glu Asp Leu Thr Lys Phe Arg Asp Ala Ser Lys Ser Leu
65                  70                  75                  80

Tyr Ala Tyr Leu Arg Gly Phe Leu Trp Gly Ser Lys Ile Glu Arg Leu
                85                  90                  95

Gly Phe Asp Glu Val Phe Leu Asp Val Thr Asp Met Ile Asp Tyr Asn
            100                 105                 110

Val Ala Leu Leu Ser His His Asp Leu Gln His Ser Phe Phe Cys Leu
            115                 120                 125

Asp Arg Glu Asp Pro Thr Lys Gly Phe Glu Phe Asp Ala Thr Arg Tyr
    130                 135                 140

Cys Gly Pro Thr Tyr Pro Pro Ser Pro Asp Ala Thr Gly Val Asp Leu
```

```
             145                 150                 155                 160
Ser Asp Pro Leu Ser Arg Arg Leu Ile Leu Gly Ser His Leu Ala Phe
             165                 170                 175

His Met Arg Met Arg Leu Asp Ala Glu Arg Gly Tyr Thr Ala Thr Val
             180                 185                 190

Gly Val Ser Thr Asn Lys Leu Leu Ala Lys Leu Val Gly Ser Val Asn
             195                 200                 205

Lys Pro Asn Asn Gln Thr Thr Leu Ile Pro Pro Tyr Ser Val Asp Arg
             210                 215                 220

Asp Asp Glu Gly Cys Ser Ser Asn Val Thr Lys Leu Met Asp Ser His
225                  230                 235                 240

Glu Leu Gly Lys Val Pro Gly Ile Gly Phe Lys Thr Ala Gln Lys Leu
             245                 250                 255

Arg Thr His Val Leu Gly Arg Glu Pro Thr Phe Gln Pro Tyr Val Glu
             260                 265                 270

Arg Ser Gln Asp Ala Gln Val Thr Val Arg Asp Val Arg Gln Phe Pro
             275                 280                 285

Gly Met Gly Pro Ala Met Leu Thr Ser Ile Leu Val Gly Pro Gly Thr
             290                 295                 300

Ala Lys Asp Ile Gly Val Arg Val Trp Glu Leu Leu His Gly Val Asp
305                  310                 315                 320

Asn Ser Glu Val Leu Glu Ala Arg Thr Ile Pro Thr Gln Ile Ser Ile
             325                 330                 335

Glu Asp Ser Tyr Lys Gly Ser Pro His Asn Asp Ala Val Arg Arg Glu
             340                 345                 350

Leu Cys His Leu Ala Ala Ser Leu Ile Arg Arg Met Arg Ala Asp Leu
             355                 360                 365

Thr Lys Met Asp Glu Thr Gly Ser Gly Arg Leu Arg Trp Leu Ala Arg
             370                 375                 380

Pro Arg Thr Val Arg Leu Ser Thr Arg Leu Arg Ser Pro Lys Met Pro
385                  390                 395                 400

Asp Gly Ser Arg Asn Tyr Ser Phe Met Asn Arg Arg Val Ser Arg Ser
             405                 410                 415

Gly Pro Ala Pro Ser Phe Ile Phe Ser Leu Asp Asp Ile Asp Ala
             420                 425                 430

Leu Ala Thr Arg Leu Val Asp Glu Leu Leu Leu Ser Met Phe Arg Arg
             435                 440                 445

Ser Phe Pro Ala Arg Ser Leu Glu Glu Leu Ala Leu Ile Asn Val Ala
             450                 455                 460

Val Thr Asn Met Thr Asp Ala Glu Pro Lys Gln Asn Arg Gly Pro Gln
465                  470                 475                 480

His Arg Gln His Ala Arg
             485

<210> SEQ ID NO 46
<211> LENGTH: 1020
<212> TYPE: DNA
<213> ORGANISM: Thermoascus aurantiacus
<220> FEATURE:
<221> NAME/KEY: CDS
<222> LOCATION: (1)..(1020)

<400> SEQUENCE: 46 gat tat gat tgt ttc tat gcc tca gtg ttt gag gcg gag aat ccg gcg      48
Asp Tyr Asp Cys Phe Tyr Ala Ser Val Phe Glu Ala Glu Asn Pro Ala
1               5                   10                  15
```

```
ctg aaa tca ctc ccc ctt gcc gta aag cag aag caa att gtc gtg aca    96
Leu Lys Ser Leu Pro Leu Ala Val Lys Gln Lys Gln Ile Val Val Thr
         20                  25                  30 tgc aac tac gag gcc cgt cgg cgg ggg ctg cgc aag ctg cag ctg atc   144
Cys Asn Tyr Glu Ala Arg Arg Arg Gly Leu Arg Lys Leu Gln Leu Ile
             35                  40                  45 agc gaa gcc aag aag gtc tgt cca gat gtg gag atc gtt ctg gga gaa   192
Ser Glu Ala Lys Lys Val Cys Pro Asp Val Glu Ile Val Leu Gly Glu
 50                  55                  60 gac ctc acc aag ttc cgc gac gcg tcg aag gcg ctg tat agc ttc ctc   240
Asp Leu Thr Lys Phe Arg Asp Ala Ser Lys Ala Leu Tyr Ser Phe Leu
 65                  70                  75                  80 aag tca ttc gtc tgg ggg gac cgc gtc gag aaa cta ggc ttt gac gag   288
Lys Ser Phe Val Trp Gly Asp Arg Val Glu Lys Leu Gly Phe Asp Glu
             85                  90                  95 gtg ttt cta gac gtc aca gaa atg atc gag tac aac gtg gag ctg ttg   336
Val Phe Leu Asp Val Thr Glu Met Ile Glu Tyr Asn Val Glu Leu Leu
            100                 105                 110 aac agc cac gac ctg gcc aat tcg ttc ttc cat cta gac aag ctt gat   384
Asn Ser His Asp Leu Ala Asn Ser Phe Phe His Leu Asp Lys Leu Asp
            115                 120                 125 cct acc gtt ggc ttt gcc tat gac gcc aca acg ttc tgc ggt ccg act   432
Pro Thr Val Gly Phe Ala Tyr Asp Ala Thr Thr Phe Cys Gly Pro Thr
130                 135                 140 tat cct cct ttc ccg gaa ggt caa ccc gga gcg atg att acc tcc tcg   480
Tyr Pro Pro Phe Pro Glu Gly Gln Pro Gly Ala Met Ile Thr Ser Ser
145                 150                 155                 160 tct ttt ccc tct gac gca ctg cgt gtg cga ctc ctt gtt gcc tcc cat   528
Ser Phe Pro Ser Asp Ala Leu Arg Val Arg Leu Leu Val Ala Ser His
                165                 170                 175 ctc gcc cgt tac ctc cgg gac caa ctt gaa caa cag aag ggt tac gct   576
Leu Ala Arg Tyr Leu Arg Asp Gln Leu Glu Gln Gln Lys Gly Tyr Ala
            180                 185                 190 gcc aca gtc ggt gta tcc aca tcc aag ctt ctt tca aag ctg gtt ggc   624
Ala Thr Val Gly Val Ser Thr Ser Lys Leu Leu Ser Lys Leu Val Gly
        195                 200                 205 agt gtc cat aag cca aat aac caa acg aca ctc ctt ccg ccc tac gct   672
Ser Val His Lys Pro Asn Asn Gln Thr Thr Leu Leu Pro Pro Tyr Ala
210                 215                 220 gct gga ggg cca ggc gaa gag agc aat gtt acg cgt ttc ctc gat gcc   720
Ala Gly Gly Pro Gly Glu Glu Ser Asn Val Thr Arg Phe Leu Asp Ala
225                 230                 235                 240 tat gag att ggc aag gtc cct gga atc ggg ttt aag ctt gat cat aag   768
Tyr Glu Ile Gly Lys Val Pro Gly Ile Gly Phe Lys Leu Asp His Lys
                245                 250                 255 ctc agg gct cac atc ctc ggc cgg gaa ccg aac tct gac tcc tac cat   816
Leu Arg Ala His Ile Leu Gly Arg Glu Pro Asn Ser Asp Ser Tyr His
            260                 265                 270 gca gtt gcg gcg gac gac aag gtc acc gtt cga cag gtc cgt ttg ttt   864
Ala Val Ala Ala Asp Asp Lys Val Thr Val Arg Gln Val Arg Leu Phe
        275                 280                 285 cct gga atg gga cct ccc ttg ctg gaa aag atc ctt ggc aga ccg ggg   912
Pro Gly Met Gly Pro Pro Leu Leu Glu Lys Ile Leu Gly Arg Pro Gly
290                 295                 300 tct cct aga gat atc ggc gtg aag gta tgg ggt ctg ata aat gga gtt   960
Ser Pro Arg Asp Ile Gly Val Lys Val Trp Gly Leu Ile Asn Gly Val
305                 310                 315                 320 gac tct tcc gaa gtc tcg aaa gcc aga gct acg ccc atc cag att gcc  1008
Asp Ser Ser Glu Val Ser Lys Ala Arg Ala Thr Pro Ile Gln Ile Ala
```

```
                        325                 330                 335
atc gaa ctc gag                                                               1020
Ile Glu Leu Glu
        340

<210> SEQ ID NO 47
<211> LENGTH: 340
<212> TYPE: PRT
<213> ORGANISM: Thermoascus aurantiacus

<400> SEQUENCE: 47

Asp Tyr Asp Cys Phe Tyr Ala Ser Val Phe Glu Ala Glu Asn Pro Ala
1               5                   10                  15

Leu Lys Ser Leu Pro Leu Ala Val Lys Gln Lys Gln Ile Val Val Thr
            20                  25                  30

Cys Asn Tyr Glu Ala Arg Arg Arg Gly Leu Arg Lys Leu Gln Leu Ile
        35                  40                  45

Ser Glu Ala Lys Lys Val Cys Pro Asp Val Glu Ile Val Leu Gly Glu
    50                  55                  60

Asp Leu Thr Lys Phe Arg Asp Ala Ser Lys Ala Leu Tyr Ser Phe Leu
65                  70                  75                  80

Lys Ser Phe Val Trp Gly Asp Arg Val Glu Lys Leu Gly Phe Asp Glu
                85                  90                  95

Val Phe Leu Asp Val Thr Glu Met Ile Glu Tyr Asn Val Glu Leu Leu
            100                 105                 110

Asn Ser His Asp Leu Ala Asn Ser Phe Phe His Leu Asp Lys Leu Asp
        115                 120                 125

Pro Thr Val Gly Phe Ala Tyr Asp Ala Thr Thr Phe Cys Gly Pro Thr
    130                 135                 140

Tyr Pro Pro Phe Pro Glu Gly Gln Pro Gly Ala Met Ile Thr Ser Ser
145                 150                 155                 160

Ser Phe Pro Ser Asp Ala Leu Arg Val Arg Leu Leu Val Ala Ser His
                165                 170                 175

Leu Ala Arg Tyr Leu Arg Asp Gln Leu Glu Gln Gln Lys Gly Tyr Ala
            180                 185                 190

Ala Thr Val Gly Val Ser Thr Ser Lys Leu Leu Ser Lys Leu Val Gly
        195                 200                 205

Ser Val His Lys Pro Asn Asn Gln Thr Thr Leu Leu Pro Pro Tyr Ala
    210                 215                 220

Ala Gly Gly Pro Gly Glu Glu Ser Asn Val Thr Arg Phe Leu Asp Ala
225                 230                 235                 240

Tyr Glu Ile Gly Lys Val Pro Gly Ile Gly Phe Lys Leu Asp His Lys
                245                 250                 255

Leu Arg Ala His Ile Leu Gly Arg Glu Pro Asn Ser Asp Ser Tyr His
            260                 265                 270

Ala Val Ala Ala Asp Asp Lys Val Thr Val Arg Gln Val Arg Leu Phe
        275                 280                 285

Pro Gly Met Gly Pro Leu Leu Glu Lys Ile Leu Gly Arg Pro Gly
    290                 295                 300

Ser Pro Arg Asp Ile Gly Val Lys Val Trp Gly Leu Ile Asn Gly Val
305                 310                 315                 320

Asp Ser Ser Glu Val Ser Lys Ala Arg Ala Thr Pro Ile Gln Ile Ala
                325                 330                 335

Ile Glu Leu Glu
        340
```

<210> SEQ ID NO 48
<211> LENGTH: 8
<212> TYPE: PRT
<213> ORGANISM: Artificial sequence
<220> FEATURE:
<223> OTHER INFORMATION: Amino acid sequence for designing PCR primer.
<220> FEATURE:
<221> NAME/KEY: MISC_FEATURE
<222> LOCATION: (2)..(2)
<223> OTHER INFORMATION: Xaa is Ala or Cys
<220> FEATURE:
<221> NAME/KEY: MISC_FEATURE
<222> LOCATION: (4)..(4)
<223> OTHER INFORMATION: Xaa is Phe or Tyr

<400> SEQUENCE: 48

Asx Xaa Phe Xaa Ala Gln Cys Glu
1               5

<210> SEQ ID NO 49
<211> LENGTH: 7
<212> TYPE: PRT
<213> ORGANISM: Artificial sequence
<220> FEATURE:
<223> OTHER INFORMATION: Amino acid sequence for designing PCR primer.
<220> FEATURE:
<221> NAME/KEY: MISC_FEATURE
<222> LOCATION: (5)..(5)
<223> OTHER INFORMATION: Xaa is Ile or Met

<400> SEQUENCE: 49

Asp Glu Val Phe Xaa Asp Leu
1               5

<210> SEQ ID NO 50
<211> LENGTH: 7
<212> TYPE: PRT
<213> ORGANISM: Artificial sequence
<220> FEATURE:
<223> OTHER INFORMATION: Amino acid sequence for designing PCR primer.
<220> FEATURE:
<221> NAME/KEY: MISC_FEATURE
<222> LOCATION: (6)..(6)
<223> OTHER INFORMATION: Xaa is Glu or Asp

<400> SEQUENCE: 50

Gly Gly Lys Leu Gly Xaa Gln
1               5

<210> SEQ ID NO 51
<211> LENGTH: 7
<212> TYPE: PRT
<213> ORGANISM: Artificial sequence
<220> FEATURE:
<223> OTHER INFORMATION: Amino acid sequence for designing PCR primer.
<220> FEATURE:
<221> NAME/KEY: MISC_FEATURE
<222> LOCATION: (6)..(6)
<223> OTHER INFORMATION: Xaa is Val, Thr, or Ile
<220> FEATURE:
<221> NAME/KEY: MISC_FEATURE
<222> LOCATION: (7)..(7)
<223> OTHER INFORMATION: Xaa is Thr, Ser, or Asn

<400> SEQUENCE: 51

Gly Phe Glu Asp Gly Xaa Xaa
1               5

<210> SEQ ID NO 52

```
<211> LENGTH: 7
<212> TYPE: PRT
<213> ORGANISM: Artificial sequence
<220> FEATURE:
<223> OTHER INFORMATION: Amino acid sequence for designing PCR primer.

<400> SEQUENCE: 52

Asp Tyr Asp Cys Phe Tyr Ala
1               5

<210> SEQ ID NO 53
<211> LENGTH: 7
<212> TYPE: PRT
<213> ORGANISM: Artificial sequence
<220> FEATURE:
<223> OTHER INFORMATION: Amino acid sequence for designing PCR primer.
<220> FEATURE:
<221> NAME/KEY: MISC_FEATURE
<222> LOCATION: (6)..(6)
<223> OTHER INFORMATION: Xaa is Arg, Lys, or Pro

<400> SEQUENCE: 53

Gly Glu Asp Leu Thr Xaa Phe
1               5

<210> SEQ ID NO 54
<211> LENGTH: 23
<212> TYPE: DNA
<213> ORGANISM: Artificial sequence
<220> FEATURE:
<223> OTHER INFORMATION: Oligonucleotide primer/probe.

<400> SEQUENCE: 54
gcggtgtaga gacgagtgcg gag                                              23

<210> SEQ ID NO 55
<211> LENGTH: 50
<212> TYPE: DNA
<213> ORGANISM: Artificial Sequence
<220> FEATURE:
<223> OTHER INFORMATION: Oligonucleotide primer/probe.
<220> FEATURE:
<221> NAME/KEY: misc_feature
<222> LOCATION: (21)..(22)
<223> OTHER INFORMATION: n at these positions is thymine, a
      thymine-thymine cyclobutane pyrimidine dimer or thymine paired
      with an abasic site.

<400> SEQUENCE: 55
ctctcacaag cagccaggca nnctccgcac tcgtctctac accgctccgc                 50

<210> SEQ ID NO 56
<211> LENGTH: 1062
<212> TYPE: DNA
<213> ORGANISM: Artificial Sequence
<220> FEATURE:
<223> OTHER INFORMATION: Chimeric polymerase AiLFSte (AiDpo4/SteDpo4LF).
<220> FEATURE:
<221> NAME/KEY: CDS
<222> LOCATION: (1)..(1059)

<400> SEQUENCE: 56 atg att gta ctt ttc gtt gat ttt gat tac ttc ttt gct caa gtt gag       48
Met Ile Val Leu Phe Val Asp Phe Asp Tyr Phe Phe Ala Gln Val Glu
1               5                   10                  15 gaa gtc ctt aac cca gaa ctt aaa ggt aag cct gta gct gtt tgc gta       96
Glu Val Leu Asn Pro Glu Leu Lys Gly Lys Pro Val Ala Val Cys Val
            20                  25                  30
```

-continued

| | | |
|---|---|---|
| ttt tct ggt agg ttt aaa gat agt ggt gca ata gct aca gct aat tat<br>Phe Ser Gly Arg Phe Lys Asp Ser Gly Ala Ile Ala Thr Ala Asn Tyr<br>35                    40                   45 | 144 |
| gag gca aga aaa cta gga ata aaa tct ggc atg cca att cct aag gca<br>Glu Ala Arg Lys Leu Gly Ile Lys Ser Gly Met Pro Ile Pro Lys Ala<br>   50                    55                   60 | 192 |
| aag gaa atc gct cct aac gcg ata tat tta cct att aga aag gat tta<br>Lys Glu Ile Ala Pro Asn Ala Ile Tyr Leu Pro Ile Arg Lys Asp Leu<br>65                    70                   75                 80 | 240 |
| tat aaa caa gtg tca gat aga ata atg tac gga ata ctc tct aaa tat<br>Tyr Lys Gln Val Ser Asp Arg Ile Met Tyr Gly Ile Leu Ser Lys Tyr<br>                  85                   90                 95 | 288 |
| tca agt aaa att gaa att gca agt ata gat gaa gct tac ctt gat att<br>Ser Ser Lys Ile Glu Ile Ala Ser Ile Asp Glu Ala Tyr Leu Asp Ile<br>             100                   105              110 | 336 |
| act gat aga gtg aaa gat tat tac gag gct tac caa cta ggt aaa aaa<br>Thr Asp Arg Val Lys Asp Tyr Tyr Glu Ala Tyr Gln Leu Gly Lys Lys<br>        115                   120              125 | 384 |
| ata aag gac gaa att tat cag aaa gaa aaa att aca gtt act att gga<br>Ile Lys Asp Glu Ile Tyr Gln Lys Glu Lys Ile Thr Val Thr Ile Gly<br>130                    135                   140 | 432 |
| att gct cca aat aag gtt ttt gct aag ata ata gcc gaa atg aat aaa<br>Ile Ala Pro Asn Lys Val Phe Ala Lys Ile Ile Ala Glu Met Asn Lys<br>145                    150                   155              160 | 480 |
| ccc aac ggt tta gga att tta aag cca gag gaa gtg gaa gga ttt ata<br>Pro Asn Gly Leu Gly Ile Leu Lys Pro Glu Glu Val Glu Gly Phe Ile<br>                  165               170                 175 | 528 |
| aga tca tta ccg ata gag gaa gtg cca ggt gta gga gat tct att tat<br>Arg Ser Leu Pro Ile Glu Glu Val Pro Gly Val Gly Asp Ser Ile Tyr<br>            180                   185              190 | 576 |
| tct aag cta aag gaa atg gag atc aaa tat tta tat gat gtt cta aaa<br>Ser Lys Leu Lys Glu Met Glu Ile Lys Tyr Leu Tyr Asp Val Leu Lys<br>        195                   200              205 | 624 |
| gtg gat ttt gaa aaa tta aaa aaa gaa ata gga aaa tct aaa gct agt<br>Val Asp Phe Glu Lys Leu Lys Lys Glu Ile Gly Lys Ser Lys Ala Ser<br>210                    215                   220 | 672 |
| tac ttg tat tct ctg gcc aga gat gaa tat ttt gaa cca gtt aag gaa<br>Tyr Leu Tyr Ser Leu Ala Arg Asp Glu Tyr Phe Glu Pro Val Lys Glu<br>225                    230                   235              240 | 720 |
| agg gtt aga aag agt ata ggg agg ata gtt act tta aag aaa aat agt<br>Arg Val Arg Lys Ser Ile Gly Arg Ile Val Thr Leu Lys Lys Asn Ser<br>                  245               250                 255 | 768 |
| agg aat ata gaa gaa att aaa cca ttc tta gct aga tca cta gat gaa<br>Arg Asn Ile Glu Glu Ile Lys Pro Phe Leu Ala Arg Ser Leu Asp Glu<br>            260                   265              270 | 816 |
| gct ttt aat aaa tta aat ggt aaa ata cct aaa aca att tat cta gta<br>Ala Phe Asn Lys Leu Asn Gly Lys Ile Pro Lys Thr Ile Tyr Leu Val<br>        275                   280              285 | 864 |
| gca gtt atg gaa gat ttg gat ata att agt aga ggt aag aca ttc cct<br>Ala Val Met Glu Asp Leu Asp Ile Ile Ser Arg Gly Lys Thr Phe Pro<br>290                    295                   300 | 912 |
| cac gga ata act aaa gag acc gca tat aaa gca tcc tta gaa tta ttg<br>His Gly Ile Thr Lys Glu Thr Ala Tyr Lys Ala Ser Leu Glu Leu Leu<br>305                    310                   315              320 | 960 |
| gaa aaa cta ttg gct gag gat aag agg aag ata aga aga ata gga gtt<br>Glu Lys Leu Leu Ala Glu Asp Lys Arg Lys Ile Arg Arg Ile Gly Val<br>                  325               330                 335 | 1008 |
| aga ttt agt aaa ttt att gag gct act agt tta gac aag ttc ttc caa<br>Arg Phe Ser Lys Phe Ile Glu Ala Thr Ser Leu Asp Lys Phe Phe Gln<br>            340                   345              350 | 1056 | ttc taa                                                                1062
Phe

<210> SEQ ID NO 57
<211> LENGTH: 353
<212> TYPE: PRT
<213> ORGANISM: Artificial Sequence
<220> FEATURE:
<223> OTHER INFORMATION: Synthetic Construct

<400> SEQUENCE: 57

Met Ile Val Leu Phe Val Asp Phe Asp Tyr Phe Phe Ala Gln Val Glu
1               5                   10                  15

Glu Val Leu Asn Pro Glu Leu Lys Gly Lys Pro Val Ala Val Cys Val
            20                  25                  30

Phe Ser Gly Arg Phe Lys Asp Ser Gly Ala Ile Ala Thr Ala Asn Tyr
        35                  40                  45

Glu Ala Arg Lys Leu Gly Ile Lys Ser Gly Met Pro Ile Pro Lys Ala
    50                  55                  60

Lys Glu Ile Ala Pro Asn Ala Ile Tyr Leu Pro Ile Arg Lys Asp Leu
65                  70                  75                  80

Tyr Lys Gln Val Ser Asp Arg Ile Met Tyr Gly Ile Leu Ser Lys Tyr
                85                  90                  95

Ser Ser Lys Ile Glu Ile Ala Ser Ile Asp Glu Ala Tyr Leu Asp Ile
            100                 105                 110

Thr Asp Arg Val Lys Asp Tyr Tyr Glu Ala Tyr Gln Leu Gly Lys Lys
        115                 120                 125

Ile Lys Asp Glu Ile Tyr Gln Lys Glu Lys Ile Thr Val Thr Ile Gly
    130                 135                 140

Ile Ala Pro Asn Lys Val Phe Ala Lys Ile Ala Glu Met Asn Lys
145                 150                 155                 160

Pro Asn Gly Leu Gly Ile Leu Lys Pro Glu Glu Val Glu Gly Phe Ile
                165                 170                 175

Arg Ser Leu Pro Ile Glu Glu Val Pro Gly Val Gly Asp Ser Ile Tyr
            180                 185                 190

Ser Lys Leu Lys Glu Met Glu Ile Lys Tyr Leu Tyr Asp Val Leu Lys
        195                 200                 205

Val Asp Phe Glu Lys Leu Lys Lys Glu Ile Gly Lys Ser Lys Ala Ser
    210                 215                 220

Tyr Leu Tyr Ser Leu Ala Arg Asp Glu Tyr Phe Glu Pro Val Lys Glu
225                 230                 235                 240

Arg Val Arg Lys Ser Ile Gly Arg Ile Val Thr Leu Lys Lys Asn Ser
                245                 250                 255

Arg Asn Ile Glu Glu Ile Lys Pro Phe Leu Ala Arg Ser Leu Asp Glu
            260                 265                 270

Ala Phe Asn Lys Leu Asn Gly Lys Ile Pro Lys Thr Ile Tyr Leu Val
        275                 280                 285

Ala Val Met Glu Asp Leu Asp Ile Ile Ser Arg Gly Lys Thr Phe Pro
    290                 295                 300

His Gly Ile Thr Lys Glu Thr Ala Tyr Lys Ala Ser Leu Glu Leu Leu
305                 310                 315                 320

Glu Lys Leu Leu Ala Glu Asp Lys Arg Lys Ile Arg Arg Ile Gly Val
                325                 330                 335

Arg Phe Ser Lys Phe Ile Glu Ala Thr Ser Leu Asp Lys Phe Phe Gln
            340                 345                 350

Phe

<210> SEQ ID NO 58
<211> LENGTH: 1062
<212> TYPE: DNA
<213> ORGANISM: Artificial Sequence
<220> FEATURE:
<223> OTHER INFORMATION: Chimeric polymerase AiLFDpo4 (AiDpo4/SsDpo4LF).
<220> FEATURE:
<221> NAME/KEY: CDS
<222> LOCATION: (1)..(1059)

<400> SEQUENCE: 58

| atg | att | gta | ctt | ttc | gtt | gat | ttt | gat | tac | ttc | ttt | gct | caa | gtt | gag | 48 |
| Met | Ile | Val | Leu | Phe | Val | Asp | Phe | Asp | Tyr | Phe | Phe | Ala | Gln | Val | Glu | |
| 1 | | | | 5 | | | | | 10 | | | | | 15 | | |

| gaa | gtc | ctt | aac | cca | gaa | ctt | aaa | ggt | aag | cct | gta | gct | gtt | tgc | gta | 96 |
| Glu | Val | Leu | Asn | Pro | Glu | Leu | Lys | Gly | Lys | Pro | Val | Ala | Val | Cys | Val | |
| | | | 20 | | | | | 25 | | | | | 30 | | | |

| ttt | tct | ggt | agg | ttt | aaa | gat | agt | ggt | gca | ata | gct | aca | gct | aat | tat | 144 |
| Phe | Ser | Gly | Arg | Phe | Lys | Asp | Ser | Gly | Ala | Ile | Ala | Thr | Ala | Asn | Tyr | |
| | | 35 | | | | | 40 | | | | | 45 | | | | |

| gag | gca | aga | aaa | cta | gga | ata | aaa | tct | ggc | atg | cca | att | cct | aag | gca | 192 |
| Glu | Ala | Arg | Lys | Leu | Gly | Ile | Lys | Ser | Gly | Met | Pro | Ile | Pro | Lys | Ala | |
| 50 | | | | | 55 | | | | | 60 | | | | | | |

| aag | gaa | atc | gct | cct | aac | gcg | ata | tat | tta | cct | att | aga | aag | gat | tta | 240 |
| Lys | Glu | Ile | Ala | Pro | Asn | Ala | Ile | Tyr | Leu | Pro | Ile | Arg | Lys | Asp | Leu | |
| 65 | | | | | 70 | | | | | 75 | | | | | 80 | |

| tat | aaa | caa | gtg | tca | gat | aga | ata | atg | tac | gga | ata | ctc | tct | aaa | tat | 288 |
| Tyr | Lys | Gln | Val | Ser | Asp | Arg | Ile | Met | Tyr | Gly | Ile | Leu | Ser | Lys | Tyr | |
| | | | | 85 | | | | | 90 | | | | | 95 | | |

| tca | agt | aaa | att | gaa | att | gca | agt | ata | gat | gaa | gct | tac | ctt | gat | att | 336 |
| Ser | Ser | Lys | Ile | Glu | Ile | Ala | Ser | Ile | Asp | Glu | Ala | Tyr | Leu | Asp | Ile | |
| | | | 100 | | | | | 105 | | | | | 110 | | | |

| act | gat | aga | gtg | aaa | gat | tat | tac | gag | gct | tac | caa | cta | ggt | aaa | aaa | 384 |
| Thr | Asp | Arg | Val | Lys | Asp | Tyr | Tyr | Glu | Ala | Tyr | Gln | Leu | Gly | Lys | Lys | |
| | | 115 | | | | | 120 | | | | | 125 | | | | |

| ata | aag | gac | gaa | att | tat | cag | aaa | gaa | aaa | att | aca | gtt | act | att | gga | 432 |
| Ile | Lys | Asp | Glu | Ile | Tyr | Gln | Lys | Glu | Lys | Ile | Thr | Val | Thr | Ile | Gly | |
| 130 | | | | | 135 | | | | | 140 | | | | | | |

| att | gct | cca | aat | aag | gtt | ttt | gct | aag | ata | ata | gcc | gaa | atg | aat | aaa | 480 |
| Ile | Ala | Pro | Asn | Lys | Val | Phe | Ala | Lys | Ile | Ile | Ala | Glu | Met | Asn | Lys | |
| 145 | | | | | 150 | | | | | 155 | | | | | 160 | |

| ccc | aac | ggt | tta | gga | att | tta | aag | cca | gag | gaa | gtg | gaa | gga | ttt | ata | 528 |
| Pro | Asn | Gly | Leu | Gly | Ile | Leu | Lys | Pro | Glu | Glu | Val | Glu | Gly | Phe | Ile | |
| | | | | 165 | | | | | 170 | | | | | 175 | | |

| aga | tca | tta | ccg | ata | gag | gaa | gtg | cca | ggt | gta | gga | gat | tct | att | tat | 576 |
| Arg | Ser | Leu | Pro | Ile | Glu | Glu | Val | Pro | Gly | Val | Gly | Asp | Ser | Ile | Tyr | |
| | | 180 | | | | | 185 | | | | | 190 | | | | |

| tct | aag | cta | aag | gaa | atg | gag | atc | aaa | tat | tta | tat | gat | gtt | cta | aaa | 624 |
| Ser | Lys | Leu | Lys | Glu | Met | Glu | Ile | Lys | Tyr | Leu | Tyr | Asp | Val | Leu | Lys | |
| | | | 195 | | | | | 200 | | | | | 205 | | | |

| gtg | gat | ttt | gaa | aaa | tta | aaa | aaa | gaa | ata | gga | aaa | tct | aaa | gct | agt | 672 |
| Val | Asp | Phe | Glu | Lys | Leu | Lys | Lys | Glu | Ile | Gly | Lys | Ser | Lys | Ala | Ser | |
| | | 210 | | | | | 215 | | | | | 220 | | | | |

| tac | ttg | tat | tct | ctg | gcc | aga | gac | gag | tat | aac | gag | cct | ata | aga | act | 720 |
| Tyr | Leu | Tyr | Ser | Leu | Ala | Arg | Asp | Glu | Tyr | Asn | Glu | Pro | Ile | Arg | Thr | |
| 225 | | | | | 230 | | | | | 235 | | | | | 240 | |

| aga | gta | cga | aag | agt | att | ggg | aga | att | gta | acg | atg | aag | aga | aat | agc | 768 |
| Arg | Val | Arg | Lys | Ser | Ile | Gly | Arg | Ile | Val | Thr | Met | Lys | Arg | Asn | Ser | |
| | | | | 245 | | | | | 250 | | | | | 255 | | |

-continued

```
agg aat ctg gag gaa ata aaa ccg tat tta ttt aga gca ata gaa gaa    816
Arg Asn Leu Glu Glu Ile Lys Pro Tyr Leu Phe Arg Ala Ile Glu Glu
            260                 265                 270 tca tat tat aag tta gat aag agg att cct aaa gct att cac gta gtc    864
Ser Tyr Tyr Lys Leu Asp Lys Arg Ile Pro Lys Ala Ile His Val Val
            275                 280                 285 gca gta acg gag gat tta gat atc gta agt aga gga aga acg ttc cct    912
Ala Val Thr Glu Asp Leu Asp Ile Val Ser Arg Gly Arg Thr Phe Pro
            290                 295                 300 cat gga ata agt aag gaa act gca tat agt gaa tca gta aaa tta tta    960
His Gly Ile Ser Lys Glu Thr Ala Tyr Ser Glu Ser Val Lys Leu Leu
305                 310                 315                 320 cag aag ata ttg gaa gag gat gag aga aag ata aga aga atc gga gta   1008
Gln Lys Ile Leu Glu Glu Asp Glu Arg Lys Ile Arg Arg Ile Gly Val
                325                 330                 335 agg ttc agt aaa ttt att gaa gca ata gga tta gac aag ttc ttc gat   1056
Arg Phe Ser Lys Phe Ile Glu Ala Ile Gly Leu Asp Lys Phe Phe Asp
                340                 345                 350 act taa                                                            1062
Thr
```

<210> SEQ ID NO 59
<211> LENGTH: 353
<212> TYPE: PRT
<213> ORGANISM: Artificial Sequence
<220> FEATURE:
<223> OTHER INFORMATION: Synthetic Construct

<400> SEQUENCE: 59

```
Met Ile Val Leu Phe Val Asp Phe Asp Tyr Phe Phe Ala Gln Val Glu
1               5                   10                  15

Glu Val Leu Asn Pro Glu Leu Lys Gly Lys Pro Val Ala Val Cys Val
                20                  25                  30

Phe Ser Gly Arg Phe Lys Asp Ser Gly Ala Ile Ala Thr Ala Asn Tyr
            35                  40                  45

Glu Ala Arg Lys Leu Gly Ile Lys Ser Gly Met Pro Ile Pro Lys Ala
    50                  55                  60

Lys Glu Ile Ala Pro Asn Ala Ile Tyr Leu Pro Ile Arg Lys Asp Leu
65                  70                  75                  80

Tyr Lys Gln Val Ser Asp Arg Ile Met Tyr Gly Ile Leu Ser Lys Tyr
                85                  90                  95

Ser Ser Lys Ile Glu Ile Ala Ser Ile Asp Glu Ala Tyr Leu Asp Ile
            100                 105                 110

Thr Asp Arg Val Lys Asp Tyr Tyr Glu Ala Tyr Gln Leu Gly Lys Lys
        115                 120                 125

Ile Lys Asp Glu Ile Tyr Gln Lys Glu Lys Ile Thr Val Thr Ile Gly
    130                 135                 140

Ile Ala Pro Asn Lys Val Phe Ala Lys Ile Ala Glu Met Asn Lys
145                 150                 155                 160

Pro Asn Gly Leu Gly Ile Leu Lys Pro Glu Glu Val Glu Gly Phe Ile
                165                 170                 175

Arg Ser Leu Pro Ile Glu Glu Val Pro Gly Val Gly Asp Ser Ile Tyr
            180                 185                 190

Ser Lys Leu Lys Glu Met Glu Ile Lys Tyr Leu Tyr Asp Val Leu Lys
        195                 200                 205

Val Asp Phe Glu Lys Leu Lys Lys Glu Ile Gly Lys Ser Lys Ala Ser
    210                 215                 220
```

```
Tyr Leu Tyr Ser Leu Ala Arg Asp Glu Tyr Asn Glu Pro Ile Arg Thr
225                 230                 235                 240

Arg Val Arg Lys Ser Ile Gly Arg Ile Val Thr Met Lys Arg Asn Ser
            245                 250                 255

Arg Asn Leu Glu Glu Ile Lys Pro Tyr Leu Phe Arg Ala Ile Glu Glu
        260                 265                 270

Ser Tyr Tyr Lys Leu Asp Lys Arg Ile Pro Lys Ala Ile His Val Val
    275                 280                 285

Ala Val Thr Glu Asp Leu Asp Ile Val Ser Arg Gly Arg Thr Phe Pro
290                 295                 300

His Gly Ile Ser Lys Glu Thr Ala Tyr Ser Glu Ser Val Lys Leu Leu
305                 310                 315                 320

Gln Lys Ile Leu Glu Glu Asp Glu Arg Lys Ile Arg Ile Gly Val
            325                 330                 335

Arg Phe Ser Lys Phe Ile Glu Ala Ile Gly Leu Asp Lys Phe Phe Asp
                340                 345                 350

Thr

<210> SEQ ID NO 60
<211> LENGTH: 375
<212> TYPE: DNA
<213> ORGANISM: Thermomyces lanuginosus
<220> FEATURE:
<221> NAME/KEY: CDS
<222> LOCATION: (1)..(375)

<400> SEQUENCE: 60 ggg gtg ctg acg acg tgt aat tac gtg gcc cgc aaa tat gga tgt cgc     48
Gly Val Leu Thr Thr Cys Asn Tyr Val Ala Arg Lys Tyr Gly Cys Arg
1               5                   10                  15 agt ggg atg gct gcc ttc gta gcg aaa agg ctc tgt ccg gat ttg atc     96
Ser Gly Met Ala Ala Phe Val Ala Lys Arg Leu Cys Pro Asp Leu Ile
            20                  25                  30 gtg atc ccc caa aac tac gag aag tac acc gcc aaa gcg cgt gag atc    144
Val Ile Pro Gln Asn Tyr Glu Lys Tyr Thr Ala Lys Ala Arg Glu Ile
        35                  40                  45 cgt gcg atc ctg gcc gag tac gac cct tgc ttc gag agc gcc agc att    192
Arg Ala Ile Leu Ala Glu Tyr Asp Pro Cys Phe Glu Ser Ala Ser Ile
    50                  55                  60 gat gaa gct tat cta aac att acg gcc ttc tgc gat gag aac cga atg    240
Asp Glu Ala Tyr Leu Asn Ile Thr Ala Phe Cys Asp Glu Asn Arg Met
65                  70                  75                  80 gat ccg cag gaa gcc gtg cag cag atg cgg gcg cgg atc tta gaa gaa    288
Asp Pro Gln Glu Ala Val Gln Gln Met Arg Ala Arg Ile Leu Glu Glu
                85                  90                  95 acc aag att tcc gtg tcg gct ggc att gcg ccc aac gcc aaa ctc gcc    336
Thr Lys Ile Ser Val Ser Ala Gly Ile Ala Pro Asn Ala Lys Leu Ala
            100                 105                 110 aag gtt gcg tcc aac aaa aat aaa ccc aat ggc caa ttt                375
Lys Val Ala Ser Asn Lys Asn Lys Pro Asn Gly Gln Phe
        115                 120                 125

<210> SEQ ID NO 61
<211> LENGTH: 125
<212> TYPE: PRT
<213> ORGANISM: Thermomyces lanuginosus

<400> SEQUENCE: 61

Gly Val Leu Thr Thr Cys Asn Tyr Val Ala Arg Lys Tyr Gly Cys Arg
```

```
                1               5                  10                  15
Ser Gly Met Ala Ala Phe Val Ala Lys Arg Leu Cys Pro Asp Leu Ile
                20                  25                  30

Val Ile Pro Gln Asn Tyr Glu Lys Tyr Thr Ala Lys Ala Arg Glu Ile
            35                  40                  45

Arg Ala Ile Leu Ala Glu Tyr Asp Pro Cys Phe Glu Ser Ala Ser Ile
        50                  55                  60

Asp Glu Ala Tyr Leu Asn Ile Thr Ala Phe Cys Asp Glu Asn Arg Met
65                  70                  75                  80

Asp Pro Gln Glu Ala Val Gln Gln Met Arg Ala Arg Ile Leu Glu Glu
                85                  90                  95

Thr Lys Ile Ser Val Ser Ala Gly Ile Ala Pro Asn Ala Lys Leu Ala
            100                 105                 110

Lys Val Ala Ser Asn Lys Asn Lys Pro Asn Gly Gln Phe
        115                 120                 125
```

<210> SEQ ID NO 62
<211> LENGTH: 22
<212> TYPE: DNA
<213> ORGANISM: Artificial Sequence
<220> FEATURE:
<223> OTHER INFORMATION: Oligonucleotide template.
<220> FEATURE:
<221> NAME/KEY: misc_feature
<222> LOCATION: (10)..(10)
<223> OTHER INFORMATION: n is a thymine or a 5-hydroxy-5-methyl hydantoin adduct.

<400> SEQUENCE: 62
cacttcggan cgtgactgat ct                                              22

<210> SEQ ID NO 63
<211> LENGTH: 12
<212> TYPE: DNA
<213> ORGANISM: Artificial Sequence
<220> FEATURE:
<223> OTHER INFORMATION: Oligonucleotide primer.

<400> SEQUENCE: 63
agatcagtca cg                                                         12

<210> SEQ ID NO 64
<211> LENGTH: 287
<212> TYPE: PRT
<213> ORGANISM: Sulfolobus acidocaldarius

<400> SEQUENCE: 64

```
Met Lys Pro Leu His Leu Ser Val Gly Arg Ile Asn Ile Asp Ile Ile
1               5                  10                  15

Ala Lys Ile Asn Lys Ile Pro Asp Ile Asp Glu Phe Glu Thr Thr Asp
            20                  25                  30

Thr Leu Glu Ile Leu Pro Gly Gly Ala Ala Val Asn Tyr Ala Val Ala
        35                  40                  45

Ile Asn Lys Phe Gly His Ser Ile Lys Ile Leu Ser Lys Ile Gly Lys
    50                  55                  60

Asp Ser Leu Val Ser Tyr Val Leu Glu Arg Ile Ala Glu Met Gly Val
65                  70                  75                  80

Gly Leu Asp Tyr Val Glu Glu Thr Asn Leu Pro Gln Ser Met Ala Leu
                85                  90                  95

Ile Phe Leu Arg Asp Asn Gly Ser Ile Ser Met Val Arg Lys Leu Gly
```

```
                    100                 105                 110
Ser Ser Ile Leu Leu Asp Lys Glu Asp Ile Lys Lys Val Phe Gly Leu
            115                 120                 125

Phe Asp Val Ile His Phe Ala Ser Ile Ser Pro Asp Ile Val Val Arg
        130                 135                 140

Asp Pro Tyr Ala Lys Leu Ile Thr Tyr Asp Pro Gly Pro Asn Ser Ser
145                 150                 155                 160

Lys Ile Pro Glu Asn Phe Gly Asn Ala Asp Ile Ile Tyr Leu Asn Glu
                165                 170                 175

Arg Glu Ser Thr Lys Val Lys Ile Glu Ser Leu Lys Ala Arg Leu Ile
            180                 185                 190

Val Ile Lys Met Gly Ser Lys Gly Ala Lys Val Ile Ser Glu Asn Glu
        195                 200                 205

Glu Cys Tyr Cys Glu Pro Tyr Lys Val Gln Thr Val Leu Asp Thr Thr
    210                 215                 220

Gly Ala Gly Asp Val Phe Asp Ala Ala Phe Asn Tyr Ala Tyr Val Gln
225                 230                 235                 240

Gly Tyr Ser Ile Glu Asp Thr Leu Arg Phe Ala Val Thr Ala Ser Ala
                245                 250                 255

Leu Lys Val Met Arg Ile Gly Gly Ile Asn Ser Pro Thr Arg Glu Glu
            260                 265                 270

Val Met Asn Ala Leu Asn Ala Tyr Thr Pro Asn Thr Lys Cys Lys
        275                 280                 285

<210> SEQ ID NO 65
<211> LENGTH: 283
<212> TYPE: PRT
<213> ORGANISM: Sulfolobus solfataricus

<400> SEQUENCE: 65

Met Ile His Leu Ala Val Gly Arg Phe Asn Ile Asp Ile Ile Val Lys
1               5                   10                  15

Leu Asp Ser Ile Pro Pro Ile Asp Ser Ser His Met Thr Asp Val Leu
            20                  25                  30

Glu Ile Met Pro Gly Gly Ala Ala Thr Asn Tyr Ala Val Ala Val Thr
        35                  40                  45

Lys Leu Gly His Ser Ala Lys Leu Leu Ala Lys Val Gly Lys Ser Glu
    50                  55                  60

Val Val Arg Ser Leu Met Glu Lys Val Val Glu Leu Gly Val Gly Leu
65                  70                  75                  80

Glu Tyr Val Glu Glu Leu Asn Glu Lys Pro Ser Ala Thr Leu Ile Phe
                85                  90                  95

Leu Arg Asn Asp Gly Thr Leu Ser Met Val Arg Arg Leu Gly Ala Ser
            100                 105                 110

Ile Leu Leu Thr Arg Glu Asp Val Lys Arg Arg Phe Gly Leu Phe Asp
        115                 120                 125

Val Ile His Phe Ala Ser Val Ser Pro Asn Val Val Arg Asp Pro
    130                 135                 140

Tyr Ala Lys Leu Val Ser Tyr Asp Pro Gly Pro Gln Ala Lys Asn Ile
145                 150                 155                 160

Glu Ser Val Asp Val Asp Ile Leu Tyr Val Asn Glu Lys Glu Tyr Glu
                165                 170                 175

Met Ile Glu Asp Lys Asn Ile Arg Ala Arg Phe Ile Val Ile Lys Met
            180                 185                 190
```

```
Gly Lys Lys Gly Ala Lys Ile Ile Thr Glu Thr Glu Glu Cys Ser Val
            195                 200                 205

Glu Pro Ile Gln Val Glu Lys Ile Val Asp Thr Thr Gly Ala Gly Asp
        210                 215                 220

Thr Phe Asp Ala Ala Phe Asn Val Thr Tyr Ser Glu Asp Lys Asp Ile
225                 230                 235                 240

Val Lys Ser Leu Gln Val Ala Ser Val Ala Ser Gly Leu Lys Val Ser
                245                 250                 255

Arg Ile Gly Gly Ile Ser Ser Pro Thr Leu Glu Glu Val Arg Glu Tyr
                260                 265                 270

Leu Arg Lys Lys Pro Asn Val Ile Cys Lys
            275                 280
```

<210> SEQ ID NO 66
<211> LENGTH: 285
<212> TYPE: PRT
<213> ORGANISM: Sulfolobus tokodaii

<400> SEQUENCE: 66

```
Met Lys Pro Ile His Leu Ser Val Gly Arg Phe Asn Ile Asp Ile Ile
1               5                   10                  15

Val Asn Ile Glu Lys Met Pro Asp Thr Asp Glu Phe Leu Thr Thr Asp
            20                  25                  30

Leu Met Glu Ile Met Pro Gly Gly Ala Ala Val Asn Tyr Ala Val Ala
        35                  40                  45

Ile Thr Lys Leu Gly His Ser Ser Lys Leu Leu Ala Lys Val Gly Lys
    50                  55                  60

Asn Thr Ile Thr Gln Ser Leu Met Glu Ser Ile Ala Glu Met Gly Val
65                  70                  75                  80

Gly Leu Asp Tyr Val Glu Glu Thr Asn Ala Pro Gln Ser Met Ala Leu
                85                  90                  95

Ile Phe Leu Arg Lys Asn Gly Lys Ile Ser Met Val Arg Lys Leu Gly
            100                 105                 110

Ala Ser Thr Leu Ile Thr Gln Glu Asp Val Lys Lys Tyr Phe Gly Leu
        115                 120                 125

Phe Asp Thr Ile His Phe Ala Ser Val Pro Pro Asn Ile Val Val Arg
130                 135                 140

Asp Pro Met Ala Arg Leu Ile Ser Tyr Asp Pro Gly Pro Phe Ser Lys
145                 150                 155                 160

Asp Val Asn Glu Val Asp Val Asp Val Leu Tyr Leu Asn Glu Lys Glu
                165                 170                 175

Ser Lys Ala Ile Asn Leu Asp Lys Ile Arg Ala Lys Ile Ile Val Ile
            180                 185                 190

Lys Met Gly Glu Lys Gly Ala Lys Val Ile Thr Glu Asn Gln Glu Cys
        195                 200                 205

Tyr Val Glu Ala Tyr Lys Val Asp Asn Ile Val Asp Thr Thr Gly Ala
    210                 215                 220

Gly Asp Val Phe Asp Ala Thr Phe Asn Tyr Ser Leu Leu Glu Gly Leu
225                 230                 235                 240

Ser Ile Glu Glu Gly Leu Lys Leu Ala Val Thr Ala Ser Ala Ile Lys
                245                 250                 255

Ile Gln Arg Leu Gly Gly Ile Ser Ser Pro Asn Leu Asn Glu Val His
            260                 265                 270

Glu Ala Leu Lys Ile Tyr Glu Pro Lys Val Lys Cys Ile
        275                 280                 285
```

<210> SEQ ID NO 67
<211> LENGTH: 140
<212> TYPE: PRT
<213> ORGANISM: Sulfolobus acidocaldarius

<400> SEQUENCE: 67

Pro Val Asn Ile Leu Gly Val Glu Glu Leu Ile Ile Leu Pro Ile
1               5                   10                  15

Thr Arg Asn Arg Glu Tyr Leu Leu Ser Leu Asn Phe Tyr Glu Asp Val
            20                  25                  30

Pro Gly Gly Arg Met Ala Arg Leu Val Leu Val Leu Asp Lys Tyr Asn
        35                  40                  45

Glu Ile Met Asn Asp Ile Thr Ala Ile Lys Gly Lys Lys Ala Val Val
50                  55                  60

Glu Val Ser Ala Ile Lys Glu Asp Met Asp Lys Leu Ser Lys Ile Ile
65                  70                  75                  80

His Ile Asp Asn Arg Ser Val Thr Asp Arg Ile Pro Phe Tyr Phe Asp
                85                  90                  95

Ile Glu Ile Leu Lys Asp Val Asp Thr Ser Gln Arg Gly Val Arg Gly
            100                 105                 110

Phe Ile Asn Tyr Val Tyr Ala Tyr Gly Asn Pro Asp Leu Ser Lys Ile
        115                 120                 125

Leu Asn Ser Leu Gln Leu Asn Val Glu Glu Ile Arg
    130                 135                 140

<210> SEQ ID NO 68
<211> LENGTH: 147
<212> TYPE: PRT
<213> ORGANISM: Sulfolobus solfataricus

<400> SEQUENCE: 68

Met Lys Ile Lys Leu Lys Ser Leu Val Arg Val Ile Gly Glu Glu Glu
1               5                   10                  15

Leu Ala Val Ile Pro Leu Ala Glu Asn Glu Tyr Tyr Val Glu Cys Leu
            20                  25                  30

Asn Phe Tyr Glu Asp Val Glu Gly Gly Arg Gln Ala Arg Leu Val Val
        35                  40                  45

Val Val Asp Lys Tyr Gly Ile Ile Arg Gln Asp Gln Val Asn Phe Ile
50                  55                  60

Lys Gly Lys Lys Thr Phe Val Asp Ala Ile Gly Val Glu Asp Asp Phe
65                  70                  75                  80

Arg Lys Ile Asn Ser Val Leu Lys Leu Asp Arg Val Ala Arg Met Phe
                85                  90                  95

Lys Val Pro Leu Tyr Phe Asp Ile Glu Ile Val Glu Lys Pro Asp Val
            100                 105                 110

Ser Lys Arg Gly Ile Arg Gly Leu Tyr Asn Tyr Leu Ser Val His Lys
        115                 120                 125

Glu Ile Asp Ile Gly Lys Leu Arg Gly Leu Val Asn Leu Ser Ile Glu
    130                 135                 140

Glu Leu Val
145

<210> SEQ ID NO 69
<211> LENGTH: 150
<212> TYPE: PRT
<213> ORGANISM: Sulfolobus tokodaii

<400> SEQUENCE: 69

```
Met Asn Ile Gly Met Arg Val Lys Ile Asn Ala Ile Ala Lys Ile Ile
1               5                   10                  15

Gly Thr Glu Glu Leu Ile Ile Pro Ile Thr Arg Asn Gly Asp Phe
            20                  25                  30

Val Leu Ala Leu Asn Phe Tyr Glu Asp Val Glu Gly Gly Arg Leu Ala
        35                  40                  45

Arg Phe Val Leu Val Tyr Asp Lys Phe Gly Glu Ile Asp Tyr Met Glu
    50                  55                  60

Thr Ile Ile Arg Gly Asp Lys Ile Ile Val Thr Ala Glu Gly Ile Glu
65                  70                  75                  80

Glu Asp Phe Lys Lys Ile Ser Asn Leu Ile Lys Ile Asp Lys Tyr Leu
                85                  90                  95

Lys Ser Asn Arg Ile Pro Leu Phe Val Asn Ile Ser Val Leu Lys Asp
            100                 105                 110

Ala Asn Ile Asn Glu Arg Gly Val Lys Gly Phe Ile Asn Tyr Val Ala
        115                 120                 125

Lys Phe Gly Arg Ile Asp Val Thr Lys Val Arg Asn Val Val Gln Leu
    130                 135                 140

Thr Ile Glu Glu Asn Val
145                 150
```

<210> SEQ ID NO 70
<211> LENGTH: 354
<212> TYPE: PRT
<213> ORGANISM: Sulfolobus acidocaldarius

<400> SEQUENCE: 70

```
Met Ile Val Ile Phe Val Asp Phe Asp Tyr Phe Phe Ala Gln Val Glu
1               5                   10                  15

Glu Val Leu Asn Pro Gln Tyr Lys Gly Lys Pro Leu Val Val Cys Val
            20                  25                  30

Tyr Ser Gly Arg Thr Lys Thr Ser Gly Ala Val Ala Thr Ala Asn Tyr
        35                  40                  45

Glu Ala Arg Lys Leu Gly Val Lys Ala Gly Met Pro Ile Ile Lys Ala
    50                  55                  60

Met Gln Ile Ala Pro Ser Ala Ile Tyr Val Pro Met Arg Lys Pro Ile
65                  70                  75                  80

Tyr Glu Ala Phe Ser Asn Arg Ile Met Asn Leu Leu Asn Lys His Ala
                85                  90                  95

Asp Lys Ile Glu Val Ala Ser Ile Asp Glu Ala Tyr Leu Asp Val Thr
            100                 105                 110

Asn Lys Val Glu Gly Asn Phe Glu Asn Gly Ile Glu Leu Ala Arg Lys
        115                 120                 125

Ile Lys Gln Glu Ile Leu Glu Lys Glu Lys Ile Thr Val Thr Val Gly
    130                 135                 140

Val Ala Pro Asn Lys Ile Leu Ala Lys Ile Ala Asp Lys Ser Lys
145                 150                 155                 160

Pro Asn Gly Leu Gly Val Ile Arg Pro Thr Glu Val Gln Asp Phe Leu
                165                 170                 175

Asn Glu Leu Asp Ile Asp Glu Ile Pro Gly Ile Gly Ser Val Leu Ala
            180                 185                 190

Arg Arg Leu Asn Glu Leu Gly Ile Gln Lys Leu Arg Asp Ile Leu Ser
    195                 200                 205
```

```
Lys Asn Tyr Asn Glu Leu Glu Lys Ile Thr Gly Lys Ala Lys Ala Leu
    210                 215                 220

Tyr Leu Leu Lys Leu Ala Gln Asn Lys Tyr Ser Glu Pro Val Glu Asn
225                 230                 235                 240

Lys Ser Lys Ile Pro His Gly Arg Tyr Leu Thr Leu Pro Tyr Asn Thr
                245                 250                 255

Arg Asp Val Lys Val Ile Leu Pro Tyr Leu Lys Ala Ile Asn Glu
            260                 265                 270

Ala Tyr Asn Lys Val Asn Gly Ile Pro Met Arg Ile Thr Val Ile Ala
            275                 280                 285

Ile Met Glu Asp Leu Asp Ile Leu Ser Lys Gly Lys Phe Lys His
    290                 295                 300

Gly Ile Ser Ile Asp Asn Ala Tyr Lys Val Ala Glu Asp Leu Leu Arg
305                 310                 315                 320

Glu Leu Leu Val Arg Asp Lys Arg Arg Asn Val Arg Arg Ile Gly Val
                325                 330                 335

Lys Leu Asp Asn Ile Ile Ile Asn Lys Thr Asn Leu Ser Asp Phe Phe
                340                 345                 350

Asp Ile

<210> SEQ ID NO 71
<211> LENGTH: 352
<212> TYPE: PRT
<213> ORGANISM: Sulfolobus solfataricus

<400> SEQUENCE: 71

Met Ile Val Leu Phe Val Asp Phe Asp Tyr Phe Tyr Ala Gln Val Glu
1               5                   10                  15

Glu Val Leu Asn Pro Ser Leu Lys Gly Lys Pro Val Val Cys Val
                20                  25                  30

Phe Ser Gly Arg Phe Glu Asp Ser Gly Ala Val Ala Thr Ala Asn Tyr
            35                  40                  45

Glu Ala Arg Lys Phe Gly Val Lys Ala Gly Ile Pro Ile Val Glu Ala
        50                  55                  60

Lys Lys Ile Leu Pro Asn Ala Val Tyr Leu Pro Met Arg Lys Glu Val
65                  70                  75                  80

Tyr Gln Gln Val Ser Ser Arg Ile Met Asn Leu Leu Arg Glu Tyr Ser
                85                  90                  95

Glu Lys Ile Glu Ile Ala Ser Ile Asp Glu Ala Tyr Leu Asp Ile Ser
            100                 105                 110

Asp Lys Val Arg Asp Tyr Arg Glu Ala Tyr Asn Leu Gly Leu Glu Ile
            115                 120                 125

Lys Asn Lys Ile Leu Glu Lys Glu Lys Ile Thr Val Thr Val Gly Ile
            130                 135                 140

Ser Lys Asn Lys Val Phe Ala Lys Ile Ala Ala Asp Met Ala Lys Pro
145                 150                 155                 160

Asn Gly Ile Lys Val Ile Asp Asp Glu Glu Val Lys Arg Leu Ile Arg
                165                 170                 175

Glu Leu Asp Ile Ala Asp Val Pro Gly Ile Gly Asn Ile Thr Ala Glu
            180                 185                 190

Lys Leu Lys Lys Leu Gly Ile Asn Lys Leu Val Asp Thr Leu Ser Ile
        195                 200                 205

Glu Phe Asp Lys Leu Lys Gly Met Ile Gly Glu Ala Lys Ala Lys Tyr
    210                 215                 220
```

-continued

Leu Ile Ser Leu Ala Arg Asp Glu Tyr Asn Glu Pro Ile Arg Thr Arg
225                 230                 235                 240

Val Arg Lys Ser Ile Gly Arg Ile Val Thr Met Lys Arg Asn Ser Arg
            245                 250                 255

Asn Leu Glu Glu Ile Lys Pro Tyr Leu Phe Arg Ala Ile Glu Glu Ser
        260                 265                 270

Tyr Tyr Lys Leu Asp Lys Arg Ile Pro Lys Ala Ile His Val Val Ala
    275                 280                 285

Val Thr Glu Asp Leu Asp Ile Val Ser Arg Gly Arg Thr Phe Pro His
290                 295                 300

Gly Ile Ser Lys Glu Thr Ala Tyr Ser Glu Ser Val Lys Leu Leu Gln
305                 310                 315                 320

Lys Ile Leu Glu Glu Asp Glu Arg Lys Ile Arg Arg Ile Gly Val Arg
                325                 330                 335

Phe Ser Lys Phe Ile Glu Ala Ile Gly Leu Asp Lys Phe Phe Asp Thr
            340                 345                 350

<210> SEQ ID NO 72
<211> LENGTH: 353
<212> TYPE: PRT
<213> ORGANISM: Sulfolobus tokodaii

<400> SEQUENCE: 72

Met Tyr Met Ile Ile Leu Phe Val Asp Phe Asp Tyr Phe Phe Ala Gln
1               5                   10                  15

Val Glu Glu Val Leu Asn Pro Gln Tyr Lys Gly Lys Pro Leu Ile Val
            20                  25                  30

Cys Val Tyr Ser Gly Arg Asn Glu Lys Ser Gly Ala Val Ala Thr Ala
        35                  40                  45

Asn Tyr Glu Ala Arg Lys Leu Gly Val Lys Ala Gly Met Pro Ile Ser
    50                  55                  60

Arg Ala Met Glu Leu Ala Pro Asn Ala Ile Phe Val Pro Met His Lys
65                  70                  75                  80

Glu Val Tyr Thr Glu Val Ser Asn Arg Ile Met Ser Ile Ile Ser Ser
                85                  90                  95

Tyr Ser Asp Lys Ile Glu Ile Ala Ser Ile Asp Glu Ala Tyr Ile Asp
            100                 105                 110

Ile Thr Ser Lys Val Lys Asn Phe Glu Glu Ala Ile Glu Leu Gly Lys
        115                 120                 125

Lys Leu Lys Arg Glu Ile Met Glu Lys Glu Lys Ile Thr Val Thr Val
    130                 135                 140

Gly Ile Ala Pro Asn Lys Val Phe Ala Lys Ile Ala Asp Arg Val
145                 150                 155                 160

Lys Pro Asn Gly Leu Gly Val Val Lys Pro Glu Glu Ile Glu Glu Phe
                165                 170                 175

Ile Lys Ser Ile Asp Ile Asp Glu Val Pro Gly Val Gly Asn Val Ile
            180                 185                 190

Ser Glu Arg Leu His Ser Leu Gly Val Asn Lys Leu Ile Asp Ile Leu
        195                 200                 205

Ser Val Ser Phe Asp Lys Leu Lys Glu Glu Ile Gly Glu Ala Lys Ala
    210                 215                 220

Phe Tyr Leu Tyr Arg Leu Ala Thr Asn Ser Tyr Phe Glu Pro Val Leu
225                 230                 235                 240

Asn Lys Glu Arg Val Pro His Gly Arg Tyr Leu Thr Leu Pro Lys Asn

-continued

```
                    245                 250                 255
Thr Arg Asp Ile Lys Val Ile Glu Leu Tyr Leu Lys Lys Ala Ile Asp
            260                 265                 270
Glu Ala Tyr Asn Lys Ile Glu Gly Ile Pro Lys Arg Met Thr Val Val
        275                 280                 285
Thr Ile Met Gln Asp Leu Asp Ile Val Ser Lys Ser Lys Thr Phe Lys
    290                 295                 300
Thr Gly Ile Ser Lys Glu Arg Ala Tyr Thr Glu Ser Ile Glu Leu Leu
305                 310                 315                 320
Lys Gln Ile Leu Gln Lys Asp Ser Arg Leu Val Arg Arg Val Gly Val
            325                 330                 335
Arg Phe Asp Asn Ile Tyr Lys Ser Lys Gly Leu Asp Val Phe Phe Asn
            340                 345                 350
Ser
```

```
<210> SEQ ID NO 73
<211> LENGTH: 33
<212> TYPE: DNA
<213> ORGANISM: Artificial Sequence
<220> FEATURE:
<223> OTHER INFORMATION: Oligonucleotide primer.

<400> SEQUENCE: 73
tattctctgg ccaacaatac ctatgctgaa ccg                                33

<210> SEQ ID NO 74
<211> LENGTH: 33
<212> TYPE: DNA
<213> ORGANISM: Artificial Sequence
<220> FEATURE:
<223> OTHER INFORMATION: Oligonucleotide primer.

<400> SEQUENCE: 74
ggtattgttg gccagagaat acaagtaact agc                                33

<210> SEQ ID NO 75
<211> LENGTH: 33
<212> TYPE: DNA
<213> ORGANISM: Artificial Sequence
<220> FEATURE:
<223> OTHER INFORMATION: Oligonucleotide primer.

<400> SEQUENCE: 75
ttctcgctgg ccagagatga atattttgaa cca                                33

<210> SEQ ID NO 76
<211> LENGTH: 33
<212> TYPE: DNA
<213> ORGANISM: Artificial Sequence
<220> FEATURE:
<223> OTHER INFORMATION: Oligonucleotide primer.

<400> SEQUENCE: 76
ttcatctctg gccagcgaga ataagtaatt agc                                33

<210> SEQ ID NO 77
<211> LENGTH: 8
<212> TYPE: PRT
<213> ORGANISM: Artificial Sequence
<220> FEATURE:
<223> OTHER INFORMATION: Amino acid sequence for designing PCR primer.

<400> SEQUENCE: 77
```

Gly Val Leu Thr Thr Cys Asn Tyr
1               5

<210> SEQ ID NO 78
<211> LENGTH: 33
<212> TYPE: DNA
<213> ORGANISM: Artificial Sequence
<220> FEATURE:
<223> OTHER INFORMATION: Oligonucleotide primer.
<220> FEATURE:
<221> NAME/KEY: misc_feature
<222> LOCATION: (12)..(24)
<223> OTHER INFORMATION: n is inosine

<400> SEQUENCE: 78
ccggaattcg gngtnytnac nacntgyaay tay                              33

<210> SEQ ID NO 79
<211> LENGTH: 7
<212> TYPE: PRT
<213> ORGANISM: Artificial Sequence
<220> FEATURE:
<223> OTHER INFORMATION: Amino acid sequence for designing PCR primer.
<220> FEATURE:
<221> NAME/KEY: MISC_FEATURE
<222> LOCATION: (7)..(7)
<223> OTHER INFORMATION: Xaa is Phe or Tyr.

<400> SEQUENCE: 79

Asn Lys Pro Asn Gly Gln Xaa
1               5

<210> SEQ ID NO 80
<211> LENGTH: 31
<212> TYPE: DNA
<213> ORGANISM: Artificial Sequence
<220> FEATURE:
<223> OTHER INFORMATION: Oligonucleotide primer.
<220> FEATURE:
<221> NAME/KEY: misc_feature
<222> LOCATION: (17)..(23)
<223> OTHER INFORMATION: n is inosine

<400> SEQUENCE: 80
gccgctcgag rwaytgnccr ttnggyttrt t                                31

<210> SEQ ID NO 81
<211> LENGTH: 27
<212> TYPE: DNA
<213> ORGANISM: Artificial Sequence
<220> FEATURE:
<223> OTHER INFORMATION: Oligonucleotide primer.

<400> SEQUENCE: 81
aaaaaccaaa agttatatgc atatgat                                     27

<210> SEQ ID NO 82
<211> LENGTH: 26
<212> TYPE: DNA
<213> ORGANISM: Artificial Sequence
<220> FEATURE:
<223> OTHER INFORMATION: Oligonucleotide primer.

<400> SEQUENCE: 82
ttacctcaag gatcctaagg aaattg                                      26

THERMOSTABLE Y-FAMILY POLYMERASES AND CHIMERAS

CROSS REFERENCE TO RELATED APPLICATIONS

This application is the U.S. National Stage of International Application No. PCT/US2005/017941, filed May 20, 2005, which was published in English under PCT Article 21(2), which claims the benefit U.S. Provisional Application No. 60/623,490 filed Oct. 29, 2004, and U.S. Provisional Application No. 60/573,684 filed May 20, 2004. These applications are incorporated by reference herein in their entirety.

FIELD

The present disclosure is related to thermostable Y-family polymerases and their use, in particular several novel Y-family polymerases and chimeras made therefrom, as well as methods of identifying other Y-family polymerases and methods of generating other chimeric Y-family polymerases.

BACKGROUND

Remarkable progress has been made in the past few years in understanding the molecular mechanisms of damage-induced mutagenesis. It has been suggested that a significant proportion of mutations arise when damaged genomic DNA is replicated in an error-prone manner by one or more low-fidelity polymerases (Goodman et al., *Annu. Rev. Biochem.* 71:17-50, 2002). These polymerases appear to have evolved to specifically facilitate replication of a wide variety of DNA lesions that might otherwise block the high fidelity replication machinery. Most of these specialized polymerases are phylogenetically related to each other and have been collectively termed "Y-family" polymerases (Ohmori et al., *Mol. Cell.* 8:7-8, 2001).

The Y-family polymerases are ubiquitous and are found in all three kingdoms of life, with many organisms often possessing more than one family member. This suggests that Y-family polymerases play important roles in cellular survival or evolutionary "fitness" (Friedberg et al., *Science* 296: 1627-30, 2002; Yeiser et al., *Proc. Natl. Acad. Sci. USA* 99:8737-41, 2002). Indeed, defects in human Polη result in the sunlight-sensitive and cancer prone xeroderma pigmentosum variant (XP-V) syndrome (Masutani et al., *Nature* 399:700-04, 1999; Johnson et al., *Science* 285:263-65, 1999), whilst mutations in *Escherichia coli* dinB reduces the cell's ability to undergo adaptive mutagenesis in stationary phase (McKenzie et al., *Mol. Cell.* 7:571-79, 2001; Tompkins et al., *J. Bacteriol.* 185:3469-72, 2003).

In vivo, DNA polymerases participate in a spectrum of DNA synthetic processes including DNA replication, DNA repair, recombination, and gene amplification (Kornberg and Baker, *DNA Replication*, pp. 929, W. H. Freeman and Co., New York, 1992). In vitro, DNA polymerases are used for DNA amplification techniques, for example polymerase chain reaction (PCR). DNA polymerases, particularly thermostable polymerases, are the key to a large number of techniques in recombinant DNA studies and in medical diagnosis of disease.

Due to the importance of Y-family polymerases in biotechnology and medicine, it would be advantageous to identify other thermostable Y-family polymerases and to create chimeric Y-family polymerases in order to optimize polymerase characteristics such as thermostability, fidelity, processivity, and translesion synthesis.

SUMMARY

Disclosed herein are novel Y-family polymerases: *Acidianus infernus* Dpo4 (SEQ ID NO: 6), *Stygiolobus azoricus* Dpo4 (SEQ ID NO: 8), *Sulfurisphaera ohwakuensis* Dpo4 (SEQ ID NO: 10), *Sulfolobus shibatae* Dpo4 (SEQ ID NO: 12), *Sulfolobus tengchongensis* Dpo4 (SEQ ID NO: 14), *Thermoascus aurantiacus* Pol eta (SEQ ID NO: 41), *Thermomyces lanuginosus* Pol eta (SEQ ID NO: 43), *Thermomyces lanuginosus* Pol iota (SEQ ID NO: 45), *Thermoascus aurantiacus* Pol iota (SEQ ID NO: 47), and *Thermomyces lanuginosus* Pol kappa (SEQ ID NO: 61). Also encompassed by this disclosure are Y-family polymerase amino acid sequences having at least 95% sequence identity to SEQ ID NO: 6, SEQ ID NO: 8, SEQ ID NO: 10, SEQ ID NO: 12, SEQ ID NO: 14, SEQ ID NO: 41, SEQ ID NO: 43, SEQ ID NO: 45, SEQ ID NO: 47, or SEQ ID NO: 61, as well as conservative variants of SEQ ID NO: 6, SEQ ID NO: 8, SEQ ID NO: 10, SEQ ID NO: 12, SEQ ID NO: 14, SEQ ID NO: 41, SEQ ID NO: 43, SEQ ID NO: 45, SEQ ID NO: 47, or SEQ ID NO: 61, wherein the Y-family polymerase has polymerase activity. Also encompassed by this disclosure are isolated nucleic acid molecules encoding these polymerases, as well as recombinant nucleic acid molecules that include a promoter sequence operably linked to the Y-family polymerase-encoding nucleic acid molecules, and cells transformed with these recombinant nucleic acid molecules.

Also disclosed herein are chimeric Y-family polymerases: Dpo4LFDbh (SEQ ID NO: 2), DbhLFDpo4 (SEQ ID NO: 4), AiLFSte (AiDpo4/SteDpo4LF) (SEQ ID NO: 57), and AiLFDpo4 (AiDpo4/SsoDpo4LF) (SEQ ID NO: 59). These chimeric polymerases include the thumb, palm, and finger domains of one Y-family polymerase and the little finger (LF) domain of another Y-family polymerase. Also encompassed by this disclosure are chimeric Y-family polymerase amino acid sequences having at least 95% sequence identity to SEQ ID NO: 2, SEQ ID NO: 4, SEQ ID NO: 57, or SEQ ID NO: 59, or conservative variants of SEQ ID NO: 2, SEQ ID NO: 4, SEQ ID NO: 57, or SEQ ID NO: 59. These chimeric Y-family polymerases retain polymerase activity. Also encompassed are isolated nucleic acid molecules encoding these chimeric polymerases, as well as recombinant nucleic acid molecules that include a promoter sequence operably linked to the Y-polymerase-encoding nucleic acid molecules, and cells transformed with these recombinant nucleic acid molecules.

The disclosure also provides a method of generating a chimeric Y-family polymerase. The method includes replacing a first LF domain of a first Y-family polymerase with a second LF domain of a second Y-family polymerase.

Also provided is a method of using a Y-family polymerase or a chimeric Y-family polymerase to add a nucleotide to a polynucleotide, the method comprising incubating a polynucleotide with a Y-family polymerase, thereby adding the nucleotide to the polynucleotide. In the disclosed embodiments, the Y-family polymerase or chimeric Y-family polymerase is *Acidianus infernus* Dpo4 (SEQ ID NO: 6), *Stygiolobus azoricus* Dpo4 (SEQ ID NO: 8), *Sulfurisphaera ohwakuensis* Dpo4 (SEQ ID NO: 10), *Sulfolobus shibatae* Dpo4 (SEQ ID NO: 12), *Sulfolobus tengchongensis* Dpo4 (SEQ ID NO: 14), *Thermoascus aurantiacus* Pol eta (SEQ ID NO: 41), *Thermomyces lanuginosus* Pol eta (SEQ ID NO: 43), *Thermomyces lanuginosus* Pol iota (SEQ ID NO: 45), *Thermoascus aurantiacus* Pol iota (SEQ ID NO: 47), *Thermomyces lanuginosus* Pol kappa (SEQ ID NO: 61), Dpo4LFDbh (SEQ ID NO: 2), DbhLFDpo4 (SEQ ID NO: 4), AiLFSte (AiDpo4/SteDpo4LF) (SEQ ID NO: 57), and AiLFDpo4 (AiDpo4/SsoDpo4LF) (SEQ ID NO: 59).

In addition, the disclosure provides a method of identifying a Y-family polymerase. The method includes amplifying a suspected Y-family polymerase DNA molecule with a first degenerate primer and a second degenerate primer, wherein the first degenerate primer hybridizes with a DNA sequence upstream of a known locus of the suspected Y-family polymerase DNA molecule, and wherein the second degenerate primer hybridizes with a DNA sequence downstream of the known locus of the suspected Y-family polymerase DNA molecule; and sequencing the amplified suspected Y-family polymerase DNA molecule, thereby identifying the Y-family polymerase.

Also disclosed are methods of amplifying ancient or damaged DNA, and methods of incorporating fluorescent or modified nucleotides into a DNA molecule. The methods include thermocycling a DNA molecule with a first primer, a second primer, and an amount of one of the Y-family polymerases disclosed herein sufficient to amplify the DNA molecule, wherein the first primer hybridizes with a DNA sequence at the 3'-end of the DNA molecule, and the second primer hybridizes with a DNA sequence at the 5'-end of the DNA molecule.

The foregoing and other features and advantages will become more apparent from the following detailed description of several embodiments, which proceeds with reference to the accompanying figures.

BRIEF DESCRIPTION OF THE FIGURES

FIG. 4 is a set of three digital images of three gels showing the ability of the Sso Dpo4, Sac Dbh, and the Dpo4LFDbh (SEQ ID NO: 2) and DbhLFDpo4 (SEQ ID NO: 4) chimeras to replicate undamaged DNA and to bypass a synthetic abasic site or a cis-syn cyclobutane pyrimidine dimer. Reactions were performed at 60° C. for 5 minutes (undamaged DNA) or 10 minutes (abasic and CPD-templates) in the presence of all four dNTPs (100 µM each) and contained 10 nM primer template and 1, 10 or 100 nM of enzyme. The local sequence context is given at the left hand side of each panel.

FIG. 5 is a pair of digital images of gels showing the specificity of Sso Dpo4-, Sac Dbh-, Dpo4LFDbh (SEQ ID NO: 2)-, and DbhLFDpo4 (SEQ ID NO: 4)-dependent nucleotide incorporation on an undamaged template. Standard 10 µl reactions were performed at 37° C. or 60° C. for 2 minutes and contained 10 nM of radiolabeled primer/template; primer: 5'-GTG TCG GGG CGA GTG CGC CG-3' (SEQ ID NO: 20), template: 5'-CTC TCA CAA GCA GCT AAG CAG CGGCGCACTCGCCCCGACACC GC-3' (SEQ ID NO: 21), with the position of the annealed primer underlined, and various amounts of polymerase. Reactions at 37° C.

FIG. 6A is a graph showing the ratio of single-base deletion to single-base substitution error rates for each polymerase (from Table 1). FIG. 6B is a graph showing a comparison of deletion rates within repetitive versus non-repetitive sequences for each of the polymerases. Error rates are given as deletions per nucleotide copied, and are calculated as described by Bebenek and Kunkel (*Meth-*

*ods. Enzymol.* 262:217-32, 1995) to correct for differences in the number of repetitive versus non-repetitive nucleotides in the targets.

Figure 7:
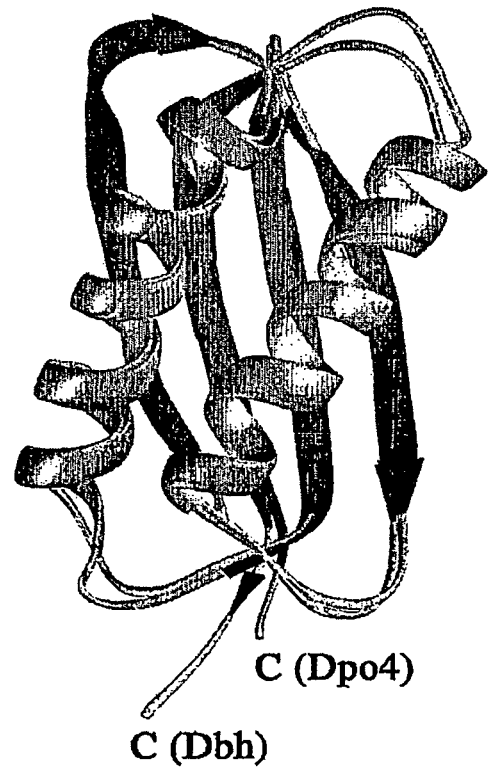

FIG. 7 is a diagram showing the superposition of the Sso Dpo4 and Sac Dbh LF domains. Although greatest primary amino acid sequence variation occurs in their respective LF domains, after superposition of the catalytic cores of Sso Dpo4 and Sac Dbh polymerases by rotating the Sac Dbh LF finger domain by 62.7° and translating it by 6.2 Å, the α-carbon backbone of the Sso Dpo4 and Sac Dbh LF domains was found to be virtually superimposable. This figure was generated using the program RIBBONS (Carson, *J. Mol. Graphics* 5:103-06, 1987).

FIG. 8 is an alignment of Sa_ribo (SEQ ID NO: 64), Ss_ribo (SEQ ID NO: 65), and St_ribo (SEQ ID NO: 66) using the Clustal method with a PAM250 residue weight table. Sequences upstream of dpo4-like genes in *Sulfolobus acidocaldarius* (Sa), *Sulfolobus solfataricus* (Ss) and *Sulfolobus tokodaii* (St) are shown.

FIG. 9 is an alignment of Sa_hypo (SEQ ID NO: 67), Ss_hypo (SEQ ID NO: 68) and St_hypo (SEQ ID NO: 69) using the Clustal method with a PAM250 residue weight table. Sequences downstream of dpo4-like genes in *Sulfolobus acidocaldarius* (Sa), *Sulfolobus solfataricus* (Ss) and *Sulfolobus tokodaii* (St) are shown.

Figure 10:
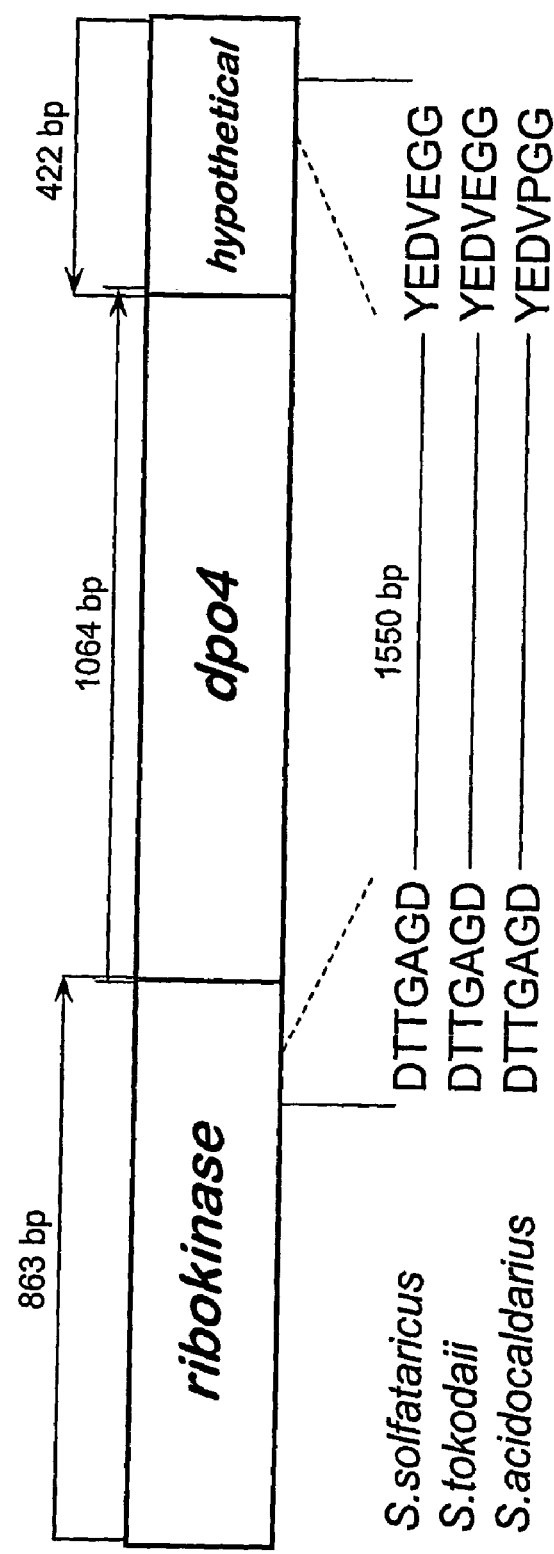

FIG. 10 is a diagrammatic representation of the cloning strategy used to clone the newly-identified Y-family polymerases. Sequences upstream (ribokinase) and downstream (hypothetical) of a dpo4-like gene are illustrated. The upstream consensus region DTTGAGD (SEQ ID NO: 22) and the downstream consensus region YEDVEGG (SEQ ID NO: 25) are also shown.

FIG. 11 is a digital image of a gel showing the expression of four of the five newly-identified Y-family polymerases. IPTG was not added to the cultures to induce expression, and the cells were grown overnight. The Y-family polymerase band is indicated by the arrow. Column C is the expression strain without plasmid. Ai: *Acidianus infernus* Dpo4 (SEQ ID NO: 6); Saz: *Stygiolobus azoricus* Dpo4 (SEQ ID NO: 8); So: *Sulfurisphaera ohwakuensis* Dpo4 (SEQ ID NO: 10); Ssh: *Sulfolobus shibatae* Dpo4 (SEQ ID NO: 12).

FIG. 12 is a digital image of a gel showing the expression of four of the five newly-identified Y-family polymerases. 0.01 mM IPTG was added to the cultures to induce expression, and the cells were grown overnight. Column C is the expression strain without plasmid. Ai: *Acidianus infernus* Dpo4 (SEQ ID NO: 6); Saz: *Stygiolobus azoricus* Dpo4 (SEQ ID NO: 8); So: *Sulfurisphaera ohwakuensis* Dpo4 (SEQ ID NO: 10); Ssh: *Sulfolobus shibatae* Dpo4 (SEQ ID NO: 12).

Figure 13:
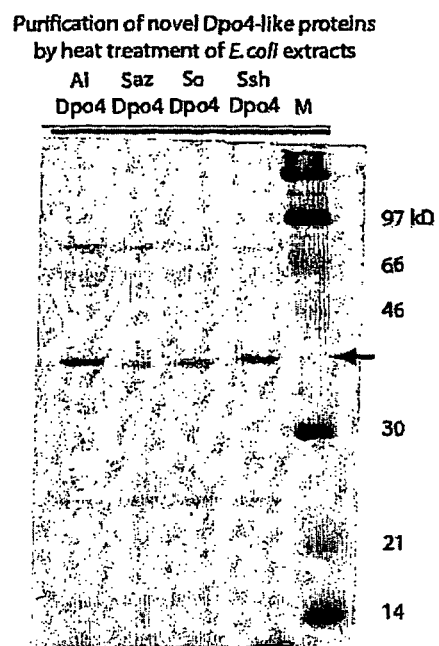

FIG. 13 is a digital image of a gel showing the thermostability of Dpo4. The extract can be enriched by heating the crude cell lysate to 70° C. for 10 minutes. This causes many of the *E. coli* proteins to precipitate. A band of the right molecular weight for the newly-identified Y-family polymerases is visible in all four extracts. The intensity and size of the protein changes in the various extracts and is consistent with the expression in the whole cell extract. The amount loaded corresponds to about 0.5-1.0 μg of the new protein.

Figure 14:
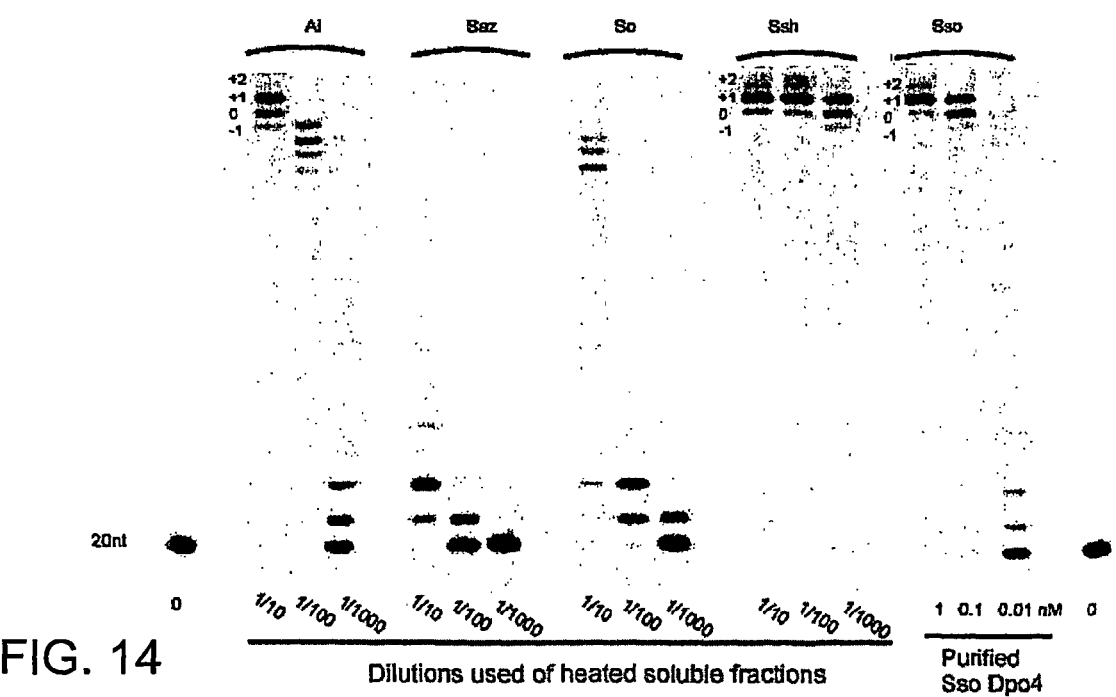

FIG. 14 is a digital image of a gel showing the results of a polymerase assay. Various amounts of the crude (heat treated) extract were included in replication assays (radiolabeled primer and unlabeled template at 70° C.). All four extracts have polymerase activity. Although polymerase activity from endogenous *E. coli* polymerases cannot be formally excluded, *E. coli* polymerases should not be active at 60° C. Also, the activity of the enzymes varies and roughly corresponds to the amount of protein added to the reaction. The *Sulfolobus shibatae* Dpo4 polymerase (SEQ ID NO: 12) is particularly active.

Figure 15:
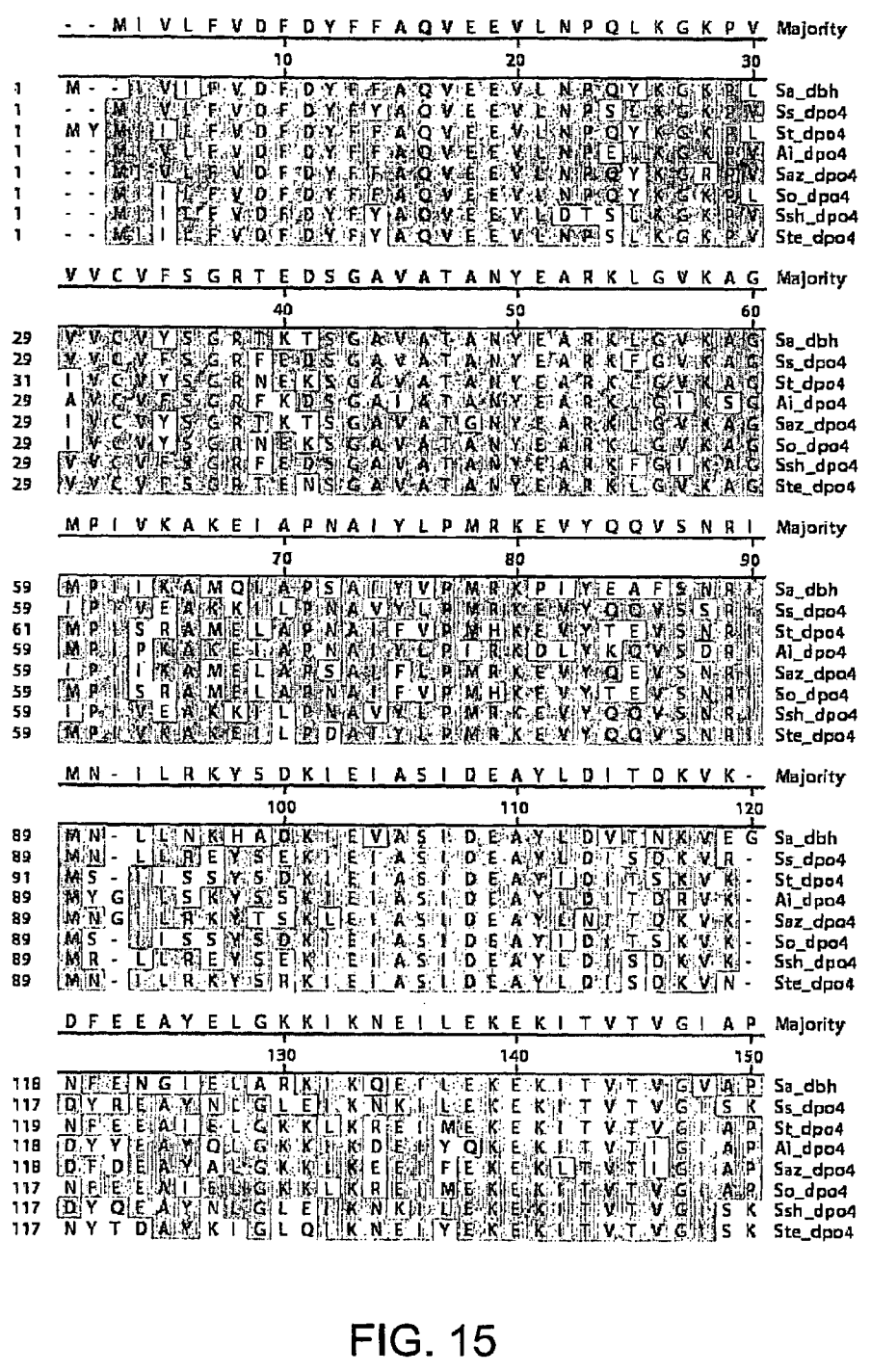
Figure 15:
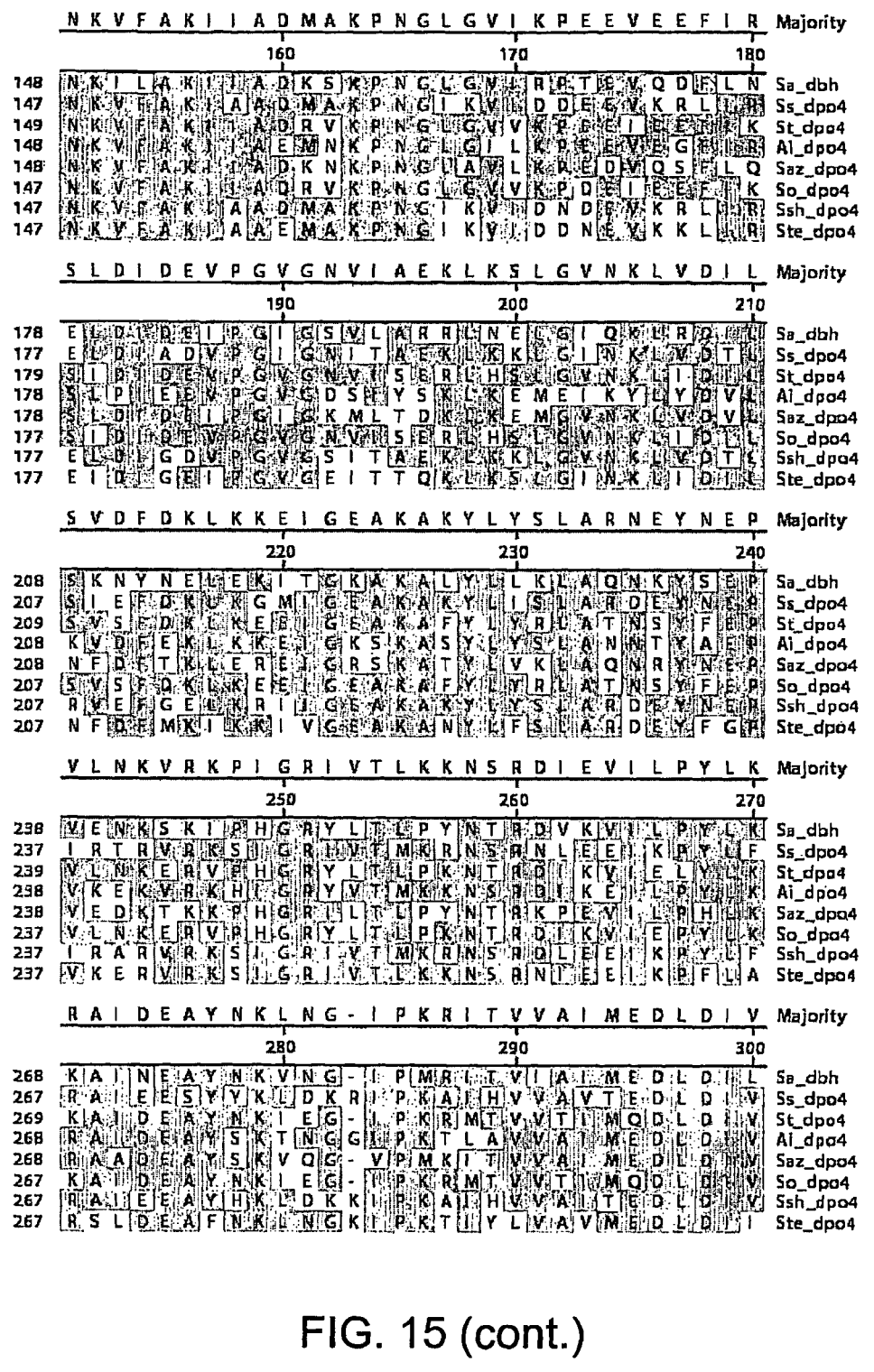

FIG. 15 is a diagram showing the alignment of the newly-identified Y-family polymerases. The alignment was performed using the Clustal method with a PAM250 weight residue weight table. Sa: *Sulfolobus acidocaldarius* Dbh (SEQ ID NO: 70); Ss: *Sulfolobus solfataricus* Dpo4 (SEQ ID NO: 71); St: *Sulfolobus tokodaii* Dpo4 (SEQ ID NO: 72); Ai: *Acidianus infernus* Dpo4 (SEQ ID NO: 6); Saz: *Stygiolobus azoricus* Dpo4 (SEQ ID NO: 8); So: *Sulfurisphaera ohwakuensis* Dpo4 (SEQ ID NO: 10); Ssh: *Sulfolobus shibatae* Dpo4 (SEQ ID NO: 12); Ste: *Sulfolobus tengchongensis* Dpo4 (SEQ ID NO: 14).

Figure 16:
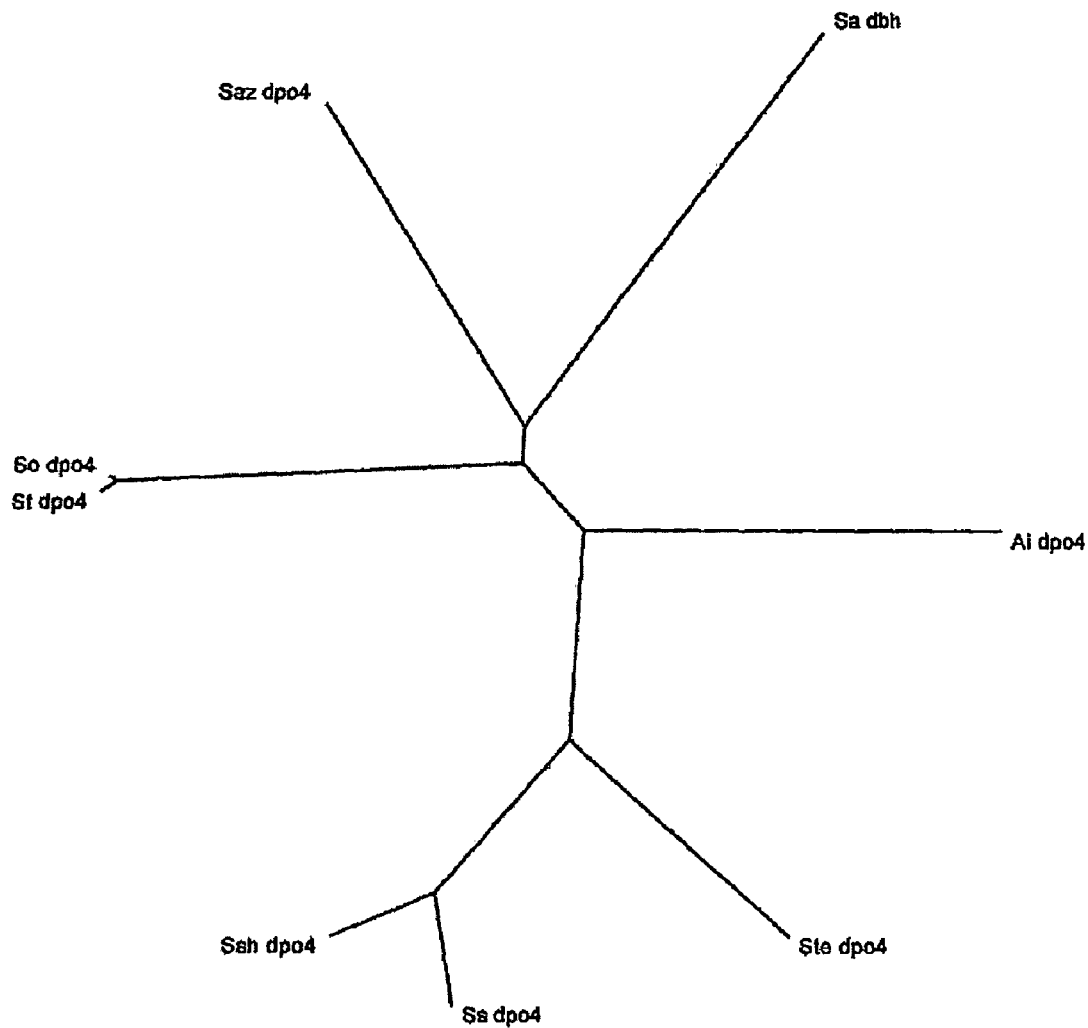

FIG. 16 is a phylogenetic tree showing the several recently identified members of the Y-polymerase family. Sa: *Sulfolobus acidocaldarius*; Ai: *Acidianus infernus*; Ste: *Sulfolobus tengchongensis*; Ss: *Sulfolobus solfataricus*; Ssh: *Sulfolobus shibatae*; St: *Sulfolobus tokodaii*; So: *Sulfurisphaera ohwakuensis*; Saz: *Stygiolobus azoricus*.

Figure 17:
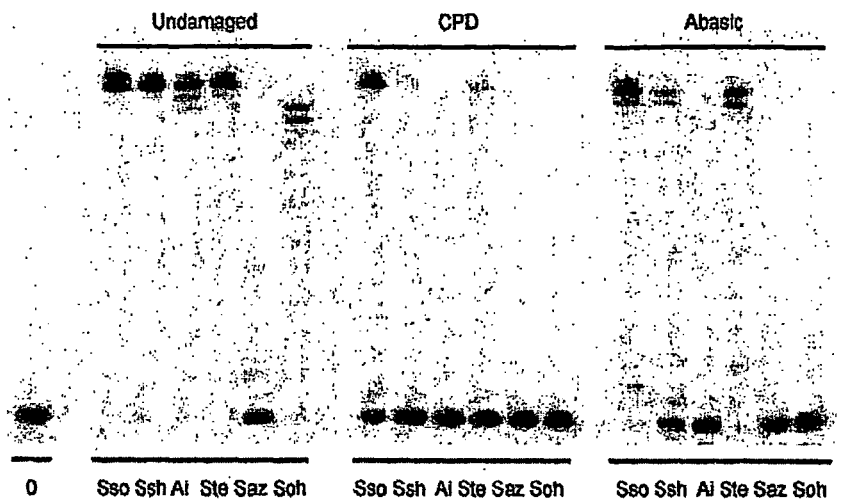

FIG. 17 is a digital image of a gel showing primer extension of undamaged and damaged templates by Dpo4 enzymes. The "undamaged" panel shows primer extension of the SSHTP2/HTU50 primer/template substrate (SEQ ID NOs: 54 and 55) by the various Dpo4 enzymes. The "CPD" panel shows primer extension of the SSHTP2/HMTT50 primer/template substrate (SEQ ID NOs: 54 and 56) containing a TT CPD dimer in the HMTT50 template. The "abasic" panel shows primer extension of the SSHTP2/HTX50 primer/template substrate (SEQ ID NOs: 54 and 56) containing an abasic site in the HTX50 template. Dpo4 is from *Sulfolobus solfataricus*; Ssh: *Sulfolobus shibatae* Dpo4, Ai: *Acidianus infernus* Dpo4; Ste: *Sulfolobus tengchongensis* Dpo4; Saz: *Stygiolobus azoricus* Dpo4; and Soh: *Sulfurisphaera ohwakuensis* Dpo4.

Figure 18:
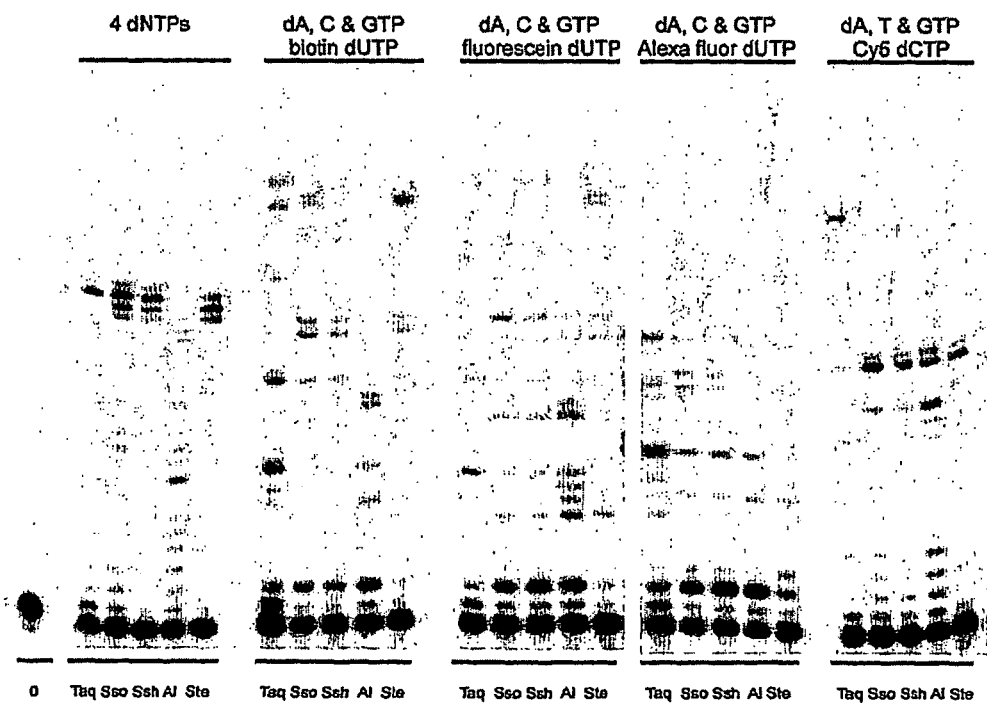

FIG. 18 is a digital image of a set of gels showing labeled nucleotide incorporation by Dpo4 enzymes during primer extension. The "4 dNTPs" panel shows primer extension in the presence of all four unmodified nucleotides. The "biotin dUTP" panel shows primer extension where dTTP was replaced with biotin-aha-dUTP (Molecular Probes, Eugene Oreg.). The "fluorescein dUTP" panel shows primer extension where dTTP was replaced with fluorescein-aha-dUTP (Molecular Probes, Eugene, Oreg.). The "Alexa fluor dUTP" panel shows primer extension where dTTP was replaced with Alexa Fluor® 647-aha-dUTP (Molecular Probes, Eugene, Oreg.). Lastly, the "Cy5 dCTP" panel shows primer extension where dCTP was replaced with Cy5-dCTP (Amersham Biosciences, Piscataway, N.J.).

Figure 19:
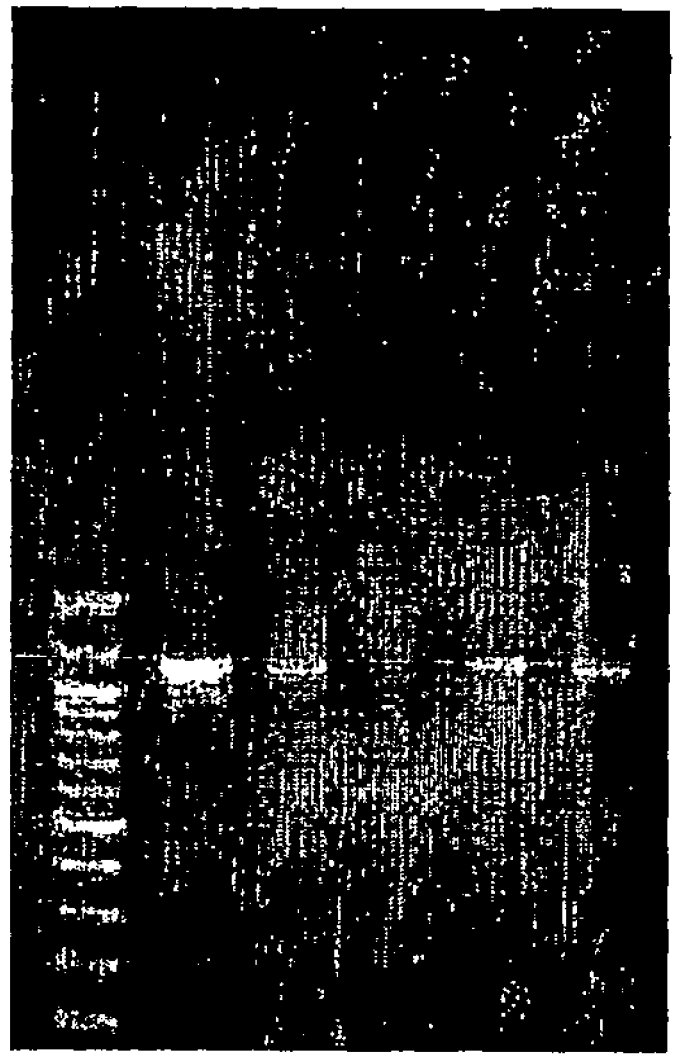

FIG. 19 is a digital image of a gel showing PCR amplification of the 1.1 kb *Sulfolobus tengchongensis* dpo4 gene. Dpo4 is from *Sulfolobus solfataricus*; Ssh: *Sulfolobus shibatae* Dpo4; Ai: *Acidianus infernus* Dpo4; Ste: *Sulfolobus tengchongensis* Dpo4. The gel shows that Sso Dpo4, Ai and Ste can all function in a "closed tube" PCR reaction and that the reaction is sufficiently robust to amplify at least a 1.1 kb amplicon.

Figure 20:
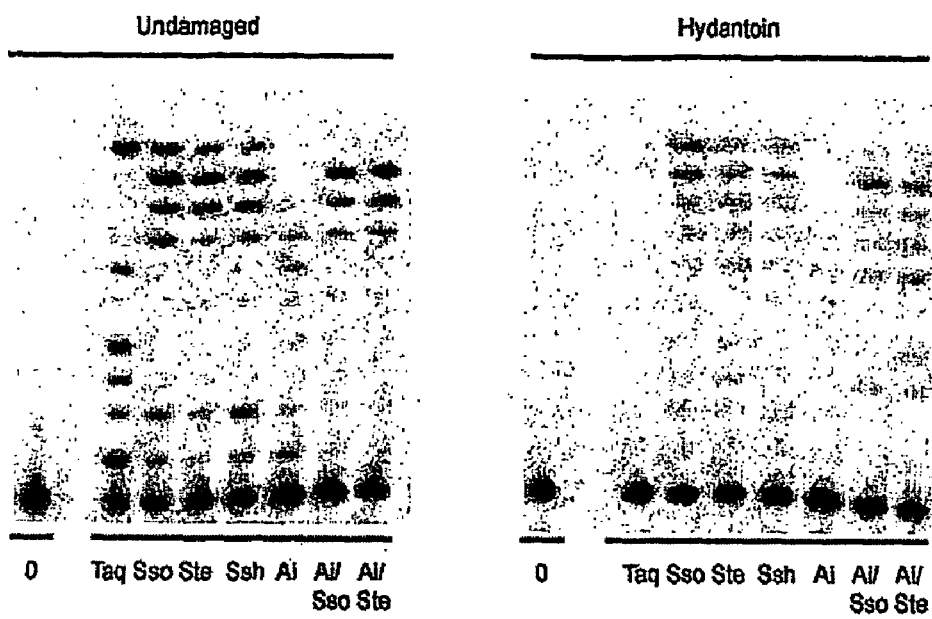

FIG. 20 is a digital image of a gel illustrating primer extension of undamaged and hydantoin containing templates by the Dpo4 enzymes from *Acidianus infernus* (SEQ ID NO: 6), *Sulfolobus shibatae* (SEQ ID NO: 12), *Sulfolobus tengchongensis* (SEQ ID NO: 14), and the AiLFSte (AiDpo4/SteDpo4LF) (SEQ ID NO: 57) and AiLFDpo4 (AiDpo4/SsoDpo4LF) (SEQ ID NO: 59) chimeras. The "undamaged" panel shows primer extension of the SSHydP/HydU22 primer/template substrate by the various Dpo4 enzymes and chimeric enzymes. The "Hydantoin" panel shows primer extension of the SSHydP/ODN primer/template substrate containing a 5-hydroxy-5-methyl hydantoin adduct in the ODN template.

Figure 21:
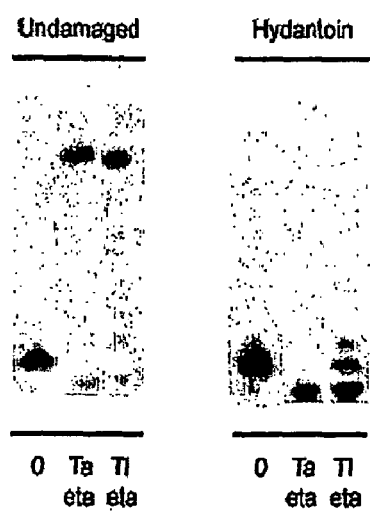

FIG. 21 is a digital image of a gel illustrating primer extension of undamaged and hydantoin containing templates by the *Thermoascus aurantiacus* Pol eta (SEQ ID NO: 41) and *Thermomyces lanuginosus* Pol eta (SEQ ID NO: 43) enzymes. The "undamaged" panel shows primer extension of the SSHydP/HydU22 primer/template substrate by the *Thermoascus aurantiacus* Pol eta and *Thermomyces lanuginosus* Pol eta enzymes. The "Hydantoin" panel shows primer extension of the SSHydP/ODN primer/template substrate containing a 5-hydroxy-5-methyl hydantoin adduct in the ODN template.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOs: 1 and 2 show the nucleic acid and amino acid sequence, respectively, of Y-family polymerase chimera Dpo4LFDbh.

SEQ ID NOs: 3 and 4 show the nucleic acid and amino acid sequence, respectively, of Y-family polymerase chimera DbhLFDpo4.

SEQ ID NOs: 5 and 6 show the nucleic acid and amino acid sequence, respectively, of Y-family polymerase *Acidianus infernus* Dpo4.

SEQ ID NOs: 7 and 8 show the nucleic acid and amino acid sequence, respectively, of Y-family polymerase *Stygiolobus azoricus* Dpo4.

SEQ ID NOs: 9 and 10 show the nucleic acid and amino acid sequence, respectively, of Y-family polymerase *Sulfurisphaera ohwakuensis* Dpo4.

SEQ ID NOs: 11 and 12 show the nucleic acid and amino acid sequence, respectively, of Y-family polymerase *Sulfolobus shibatae* Dpo4.

SEQ ID NOs: 13 and 14 show the nucleic acid and amino acid sequence, respectively, of Y-family polymerase *Sulfolobus tengchongensis* Dpo4.

SEQ ID NO: 15 shows the nucleic acid sequence of an oligonucleotide primer/probe.

SEQ ID NO: 16 shows the nucleic acid sequence of an oligonucleotide primer/probe.

SEQ ID NO: 17 shows the nucleic acid sequence of an oligonucleotide template.

SEQ ID NO: 18 shows the nucleic acid sequence of an oligonucleotide template.

SEQ ID NO: 19 shows the nucleic acid sequence of an oligonucleotide abasic (N)-containing template.

SEQ ID NO: 20 shows the nucleic acid sequence of an oligonucleotide primer/probe.

SEQ ID NO: 21 shows the nucleic acid sequence of an oligonucleotide template.

SEQ ID NO: 22 shows the amino acid sequence of a Y-family polymerase consensus region.

SEQ ID NO: 23 shows the nucleic acid sequence of an oligonucleotide primer/probe.

SEQ ID NO: 24 shows the nucleic acid sequence of an oligonucleotide primer/probe.

SEQ ID NO: 25 shows the amino acid sequence of a Y-family polymerase consensus region.

SEQ ID NO: 26 shows the nucleic acid sequence of an oligonucleotide primer/probe.

SEQ ID NO: 27 shows the nucleic acid sequence of an oligonucleotide primer/probe.

SEQ ID NO: 28 shows the nucleic acid sequence of a degenerate 5'-primer used in cloning *S. tengchongensis* Dpo4.

SEQ ID NO: 29 shows the nucleic acid sequence of a degenerate 3'-primer used in cloning *S. tengchongensis* Dpo4.

SEQ ID NO: 30 shows the nucleic acid sequence of a degenerate 5'-primer used in cloning *S. tengchongensis* Dpo4.

SEQ ID NO: 31 shows the nucleic acid sequence of a degenerate 3'-primer used in cloning *S. tengchongensis* Dpo4.

SEQ ID NO: 32 shows the nucleic acid sequence of a primer (ssdbhbam) used in cloning the *S. acidocaldarius* dbh gene.

SEQ ID NO: 33 shows the nucleic acid sequence of a primer (ssdbhbsp) used in cloning the *S. acidocaldarius* dbh gene.

SEQ ID NO: 34 shows the nucleic acid sequence of a primer (P2SWDW) used in generating a BalI/MscI restriction site in the *S. acidocaldarius* dbh gene.

SEQ ID NO: 35 shows the nucleic acid sequence of a primer (P2SWUP) used in generating a BalI restriction site in the *S. acidocaldarius* dbh gene.

SEQ ID NO: 36 shows the nucleic acid sequence of a primer (P1ndeIup) used in cloning DbhLFDpo4.

SEQ ID NO: 37 shows the nucleic acid sequence of a primer (P1bal2dw) used in cloning DbhLFDpo4.

SEQ ID NO: 38 shows the nucleic acid sequence of the primer P1balIup.

SEQ ID NO: 39 shows the nucleic acid sequence of the primer P1bam2dw.

SEQ ID NOs: 40 and 41 show the nucleic acid and amino acid sequence, respectively, of *Thermoascus aurantiacus* Pol eta.

SEQ ID NOs: 42 and 43 show the nucleic acid and amino acid sequence, respectively, of *Thermomyces lanuginosus* Pol eta.

SEQ ID NOs: 44 and 45 show the partial nucleic acid and amino acid sequence, respectively, of *Thermomyces lanuginosus* Pol iota.

SEQ ID NOs: 46 and 47 show the partial nucleic acid and amino acid sequence, respectively, of *Thermoascus aurantiacus* Pol iota.

SEQ ID NOs: 48-51 show several amino acid sequences used to generate PCR primers for amplifying polymerase eta genes.

SEQ ID NO: 52 shows an amino acid sequence used to generate PCR primers for amplifying polymerase iota genes.

SEQ ID NO: 53 shows an amino acid sequence used to generate PCR primers for amplifying polymerase iota genes.

SEQ ID NO: 54 shows a nucleic acid sequence (SSHTP2) useful as a template for primer extension assays.

SEQ ID NO: 55 shows a nucleic acid sequence (HTU50) useful as a template for primer extension assays.

SEQ ID NOs: 56 and 57 show the nucleic acid and amino acid sequence, respectively, of Y-family polymerase chimera AiLFSte (AiDpo4/SteDpo4LF).

SEQ ID NOs: 58 and 59 show the nucleic acid and amino acid sequence, respectively, of Y-family polymerase chimera AiLFDpo4 (AiDpo4/SsoDpo4LF).

SEQ ID NOs: 60 and 61 show the partial nucleic acid and amino acid sequence, respectively, of *Thermomyces lanuginosus* Pol kappa.

SEQ ID NO: 62 shows the nucleic acid sequence of an oligonucleotide template.

SEQ ID NO: 63 shows the nucleic acid sequence of an oligonucleotide primer/probe.

SEQ ID NO: 64 shows the amino acid sequence of Sa_ribo.

SEQ ID NO: 65 shows the amino acid sequence of Ss_ribo.

SEQ ID NO: 66 shows the amino acid sequence of St_ribo.

SEQ ID NO: 67 shows the amino acid sequence of Sa_hypo.

SEQ ID NO: 68 shows the amino acid sequence of Ss_hypo.

SEQ ID NO: 69 shows the amino acid sequence of St_hypo.

SEQ ID NO: 70 shows the amino acid sequence of *Sulfolobus acidocaldarius* Dbh.

SEQ ID NO: 71 shows the amino acid sequence of *Sulfolobus solfataricus* Dpo4.

SEQ ID NO: 72 shows the amino acid sequence of *Sulfolobus tokodaii* Dpo4.

SEQ ID NOs: 73-76 show the nucleic acid sequences of several oligonucleotide primers.

SEQ ID NO: 77 shows an amino acid sequence used to generate PCR primers for amplifying polymerase kappa genes.

SEQ ID NO: 78 shows the nucleic acid sequence of an oligonucleotide primer.

SEQ ID NO: 79 shows an amino acid sequence used to generate PCR primers for amplifying polymerase kappa genes.

SEQ ID NOs: 80-82 show the nucleic acid sequences of several oligonucleotide primers.

DETAILED DESCRIPTION

I. Abbreviations

Ai: *Acidianus infernus* Dpo4
° C.: degrees Celsius
cDNA: complementary DNA
CPD: cyclobutane pyrimidine dimer
g: gram
LF: little finger
min: minute(s)
ml: milliliter
ODN: oligodeoxynucleotide
PCR: polymerase chain reaction
Sac/Sa: *Sulfolobus acidocaldarius* Dbh
Saz: *Stygiolobus azoricus* Dpo4
Soh/So: *Sulfurisphaera ohwakuensis* Dpo4
Ssh: *Sulfolobus shibatae* Dpo4
Sso/Ss: *Sulfolobus solfataricus* Dpo4
Sto/St: *Sulfolobus tokodaii* Dpo4
Ste: *Sulfolobus tengchongensis* Dpo4
μg: microgram(s)
μl: microliter(s)

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the invention, the following explanations of specific terms are provided:

Animal: Living multi-cellular vertebrate organisms, a category that includes for example, mammals and birds.

Amplification: When used in reference to a nucleic acid, any technique that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification can be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain-reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Antisense, sense, and antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target.

Catalytic activity or activity: When used in reference to a polymerase, these terms refer to the enzymatic properties of a polymerase. Catalytic activity includes, for example: enzymatic properties such as the rate of synthesis of nucleic acid polymers; the Km for substrates such as nucleoside triphosphates and template strand; the fidelity of template-directed incorporation of nucleotides, where the frequency of incorporation of non-complementary nucleotides is compared to that of complementary nucleotides; processivity, the number of nucleotides synthesized by a polymerase prior to dissociation from the DNA template; discrimination of the ribose sugar; and stability, for example, at elevated temperatures. "Measurable polymerase activity" refers to polymerase activity, such as one or more of the enzymatic properties of a polymerase (e.g., the catalytic activities described above), that can be detected using methods well know to those of ordinary skill in the art.

Polymerases can discriminate between templates, for example, DNA polymerases generally use DNA templates and RNA polymerases generally use RNA templates, whereas reverse transcriptases use both RNA and DNA templates. DNA polymerases also discriminate between deoxyribonucleoside triphosphates and dideoxyribonucleoside triphosphates. Any of these distinct enzymatic properties can be included in the meaning of the term catalytic activity, including any single property, any combination of properties or all of the properties.

Chimera: A nucleic acid sequence, amino acid sequence, or protein that comprises nucleic acid sequence, amino acid sequence, or protein from two or more sources, for example amino acid sequence from two or more different species. In general, chimeric sequences are the result of genetic engineering.

Chimeric Y-family polymerases can be created by replacing a portion of a native Y-family polymerase with an orthologous portion of another Y-family polymerase. Specific, non-limiting examples of chimeric Y-family polymerases include DbhLFDpo4, Dpo4LFDbh, AiLFSte (AiDpo4/SteDpo4LF), and AiLFDpo4 (AiDpo4/SsoDpo4LF). Other chimeric Y-family polymerases can be created using the Y-family polymerases disclosed herein, for example *Acidianus infernus* Dpo4, *Stygiolobus azoricus* Dpo4, *Sulfurisphaera ohwakuensis* Dpo4, *Sulfolobus shibatae* Dpo4, or *Sulfolobus tengchongensis* Dpo4. In some chimeric Y-family polymerases, the LF domain of one Y-family polymerase has been substituted for the LF domain of another Y-family polymerase. In other chimeric Y-family polymerases, the finger domain of one Y-family polymerase has been substituted for the finger domain of another Y-family polymerase. In still other chimeric Y-family polymerases, both substitutions have been made.

DNA (deoxyribonucleic acid): A long chain polymer which comprises the genetic material of most living organisms (some viruses have genes comprising ribonucleic acid (RNA)). The repeating units in DNA polymers are four different nucleotides, each of which comprises one of the four bases, adenine, guanine, cytosine and thymine bound to a deoxyribose sugar to which a phosphate group is attached. Triplets of nucleotides (referred to as codons) code for each amino acid in a polypeptide. The term codon is also used for the corresponding (and complementary) sequences of three nucleotides in the mRNA into which the DNA sequence is transcribed.

Unless otherwise specified, any reference to a DNA molecule is intended to include the reverse complement of that DNA molecule. Except where single-strandedness is required by the text herein, DNA molecules, though written to depict only a single strand, encompass both strands of a double-stranded DNA molecule. Thus, a reference to the nucleic acid molecule that encodes a specific protein, or a fragment thereof, encompasses both the sense strand and its reverse complement. Thus, for instance, it is appropriate to generate probes or primers from the reverse complement sequence of the disclosed nucleic acid molecules.

Deletion: The removal of a sequence of DNA, the regions on either side being joined together.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Fidelity: When used in reference to a polymerase, fidelity refers to the accuracy of template-directed incorporation of complementary bases in a synthesized DNA strand relative to the template strand. Fidelity is measured based on the frequency of incorporation of incorrect bases in the newly-synthesized nucleic acid strand. The incorporation of incorrect bases can result in point mutations, insertions or deletions. Fidelity can be calculated according to the procedures described in Tindall and Kunkel (*Biochemistry* 27:6008-13, 1988). Methods for determining fidelity are well known in the art. A polymerase can exhibit high fidelity or low fidelity. As used herein, the term "high fidelity" is intended to mean a frequency of accurate base incorporation that exceeds a predetermined value. Similarly, the term "low fidelity" is intended to mean a frequency of accurate base incorporation that is lower than a predetermined value. The predetermined value can be, for example, a desired frequency of accurate base incorporation or the fidelity of a known polymerase.

As used herein, the term "altered fidelity" refers to the fidelity of a chimeric polymerase that differs from the fidelity of one or both of the parent polymerases from which the chimeric polymerase is derived. The altered fidelity can either be higher or lower than the fidelity of a parent polymerase. Thus, chimeric polymerases with altered fidelity can be classified as high fidelity polymerases or low fidelity polymerases. Altered fidelity can be determined by assaying the parent and chimeric polymerases and comparing their activities using any assay that measures the accuracy of template directed incorporation of complementary bases. Such methods are known to those skilled in the art.

Finger domain: Although they share little primary amino acid sequence homology with DNA polymerases from other families, structural studies of two archaeal DinB-like polymerases, Sac Dbh and Sso Dpo4, and of the catalytic core of *Saccharomyces cerevisiae* Polη (also referred to herein as "Pol eta") reveal they are topologically similar to classical polymerases in that they resemble a right hand and possess "finger", "palm" and "thumb" sub-domains. In addition, they possess a unique domain that has been termed the "little finger" (LF; Ling et al., *Cell* 107:91-102, 2001), "wrist" (Silvian et al., *Nat. Struct. Biol.* 8:984-89, 2001) or "PAD: polymerase associated domain" (Trincao et al., *Mol. Cell.* 8:417-26, 2001).

In one specific, non-limiting example, the finger domain of Dpo4 is represented by amino acids 11-78 of the Dpo4 amino acid sequence. In another specific, non-limiting example, the finger domain of Dbh is represented by amino acids 11-78 of the Dbh amino acid sequence.

Functional fragments and variants of a polypeptide: Included are those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential functions of a protein. See Stryer, *Biochemistry* 3rd Ed., (c) 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *Short Protocols in Molecular Biology*, 4$^{th}$ ed., John Wiley & Sons, Inc., 1999). Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications, as will be readily appreciated by those well skilled in the art. A variety of methods for labeling polypeptides and labels useful for such purposes are well known in the art, and include radioactive isotopes such as $^{32}$P, ligands which bind to or are bound by labeled specific binding partners (e.g., antibodies), fluorophores, chemiluminescent agents, enzymes, and antiligands. Functional fragments and variants can be of varying length. For example, some fragments have at least 10, 25, 50, 75, 100, or 200 amino acid residues.

A functional fragment or variant of a thermostable Y-family polymerase is defined herein as a polypeptide which retains measurable polymerase activity.

Heterologous: A type of sequence that is not normally (i.e. in the wild-type sequence) found adjacent to a second sequence. In one embodiment, the sequence is from a different genetic source, such as a virus or organism, than the second sequence.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as base pairing. More specifically, A will hydrogen bond to T or U, and G will bond to C. Complementary refers to the base pairing that occurs between to distinct nucleic acid sequences or two distinct regions of the same nucleic acid sequence.

Isolated: A biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

Little finger domain: Although they share little primary amino acid sequence homology with DNA polymerases from other families, structural studies of two archaeal DinB-like polymerases, Dbh and Dpo4, and of the catalytic core of *Saccharomyces cerevisiae* Polη reveal they are topologically similar to classical polymerases in that they resemble a right hand and possess "fingers", "palm" and "thumb" sub-domains. In addition, they possess a unique domain that has been termed the "little finger" (LF; Ling et al., *Cell* 107:91-102, 2001), "wrist" (Silvian et al., *Nat. Struct. Biol.* 8:984-89, 2001) or "PAD: polymerase associated domain" (Trincao et al., *Mol. Cell.* 8:417-26, 2001).

The LF domain is the least conserved of the four domains in the Y-family polymerases, and the variable LF domain plays a major role in determining the enzymatic and biological properties of each individual Y-family member.

In one specific, non-limiting example, the LF domain of the chimeras and Y-family polymerases disclosed herein is found at codons 245-353 (DbhLFDpo4), 244-353 (Dpo4LFDbh), 245-354 (*Acidianus infernus* Dpo4), 245-350 (*Stygiolobus azoricus* Dpo4), 244-351 (*Sulfurisphaera ohwakuensis* Dpo4), 244-352 (*Sulfolobus shibatae* Dpo4), and 244-351 (*Sulfolobus tengchongensis* Dpo4). The LF domain is connected to the thumb domain of the proteins by a 14 amino acid linker protein. Thus the LF domain and linker region that connects it to the thumb domain of the chimeras and Y-family polymerases disclosed herein are found at codons 231-353 (DbhLFDpo4), 230-353 (Dpo4LFDbh), 231-354 (*Acidianus infernus* Dpo4), 231-350 (*Stygiolobus azoricus* Dpo4), 230-351 (*Sulfurisphaera ohwakuensis* Dpo4), 230-352 (*Sulfolobus shibatae* Dpo4), and 230-351 (*Sulfolobus tengchongensis* Dpo4).

Label: A biomolecule attached covalently or noncovalently to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989 and Ausubel et al. *Short Protocols in Molecular Biology*, 4$^{th}$ ed., John Wiley & Sons, Inc., 1999. For example, ATP can be labeled in any one of its three phosphate groups with radioisotopes such as $^{32}$P or $^{33}$P, or in its sugar moiety with a radioisotope such as $^{35}$S.

Linker region: A segment of DNA or amino acid sequence connecting domains. In one specific, non-limiting example, the LF domain of a Y-family polymerase is joined to the thumb domain by a 14 amino acid linker region. In another specific, non-limiting example, the LF domain of Dpo4 is joined to the thumb domain by a linker region comprising amino acids 230-244.

Mammal: This term includes both human and non-human mammals. Similarly, the term subject includes both human and veterinary subjects.

Nucleotide: This term includes, but is not limited to, a monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Oligonucleotide: A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules.

Particular oligonucleotides and oligonucleotide analogs can include linear sequences up to about 200 nucleotides in length, for example a sequence (such as DNA or RNA) that is at least 6 bases, for example at least 8, 10, 15, 20, 25, 30, 35, 40, 45, 50, 100 or even 200 bases long, or from about 6 to about 50 bases, for example about 10-25 bases, such as 12, 15 or 20 bases.

Open reading frame: A series of nucleotide triplets (codons) coding for amino acids without any internal termination codons. These sequences are usually translatable into a peptide.

Polymerase: An enzyme that polymerizes nucleoside triphosphates. Polymerases use a template nucleic acid strand to synthesize a complementary nucleic acid strand. The template strand and synthesized nucleic acid strand can independently be either DNA or RNA. Polymerases can include, for example, DNA polymerases such as *Escherichia coli* DNA polymerase I and *Thermus aquaticus* (Taq) DNA polymerase I, DNA-dependent RNA polymerases and reverse transcriptases. A polymerase need not contain all of the amino acids found in a native enzyme, but only those which are sufficient to allow the polymerase to carry out a desired catalytic activity. Catalytic activities include, for example, 5'-3' polymerization, 5'-3' exonuclease, and 3'-5' exonuclease activities.

Polypeptide: A polymer in which the monomers are amino acid residues which are joined together through amide bonds. When the amino acids are alpha-amino acids, either the L-optical isomer or the D-optical isomer can be used, the L-isomers being preferred. The term polypeptide or protein as used herein encompasses any amino acid sequence and includes modified sequences such as glycoproteins. The term polypeptide is specifically intended to cover naturally occurring proteins, as well as those that are recombinantly or synthetically produced.

The term polypeptide fragment refers to a portion of a polypeptide which exhibits at least one useful epitope. The phrase "functional fragments of a polypeptide" refers to all fragments of a polypeptide that retain an activity, or a measurable portion of an activity, of the polypeptide from which the fragment is derived. Fragments, for example, can vary in size from a polypeptide fragment as small as an epitope capable of binding an antibody molecule to a large polypeptide capable of participating in the characteristic induction or programming of phenotypic changes within a cell. An epitope is a region of a polypeptide capable of binding an immunoglobulin generated in response to contact with an antigen. Thus, smaller peptides containing the biological activity of insulin, or conservative variants of the insulin, are thus included as being of use.

The term substantially purified polypeptide as used herein refers to a polypeptide that is substantially free of other proteins, lipids, carbohydrates or other materials with which it is naturally associated. In one embodiment the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Variations in the cDNA sequence that result in amino acid changes, whether conservative or not, are usually minimized in order to preserve the functional and immunologic identity of the encoded protein. The immunologic identity of the protein may be assessed by determining whether it is recognized by an antibody; a variant that is recognized by such an antibody is immunologically conserved. Any cDNA sequence variant will preferably introduce no more than twenty, and preferably fewer than ten amino acid substitutions into the encoded polypeptide. Variant amino acid sequences may, for example, be 80%, 90% or even 95% or 98% identical to the native amino acid sequence. Programs and algorithms for determining percentage identity can be found at the NCBI website.

Probes and primers: Nucleic acid probes and primers can be readily prepared based on the nucleic acid molecules provided in this invention. A probe comprises an isolated nucleic acid attached to a detectable label or reporter molecule. Typical labels include radioactive isotopes, enzyme substrates, co-factors, ligands, chemiluminescent or fluorescent agents, haptens, and enzymes. Methods for labeling and guidance in the choice of labels appropriate for various purposes are discussed, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989 and Ausubel et al. *Short Protocols in Molecular Biology*, $4^{th}$ ed., John Wiley & Sons, Inc., 1999.

Primers are short nucleic acid molecules, preferably DNA oligonucleotides 10 nucleotides or more in length. More preferably, longer DNA oligonucleotides can be about 15, 17, 20, or 23 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, e.g., by the PCR or other nucleic-acid amplification methods known in the art.

Methods for preparing and using nucleic acid primers and probes are described, for example, in Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989; Ausubel et al. *Short Protocols in Molecular Biology*, $4^{th}$ ed., John Wiley & Sons, Inc., 1999; and Innis et al. *PCR Protocols, A Guide to Methods and Applications*, Academic Press, Inc., San Diego, Calif., 1990. PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular probe or primer increases with its length. Thus, for example, a primer comprising 30 consecutive nucleotides of a Y-family polymerase-encoding nucleotide will anneal to a target sequence, such as a Y-family polymerase gene homolog from the gene family contained within a human genomic DNA library, with a higher specificity than a corresponding primer of only 15 nucleotides. Thus, in order to obtain greater specificity, probes and primers can be selected that comprise at least 17, 20, 23, 25, 30, 35, 40, 45, 50 or more consecutive nucleotides of Y-family polymerase nucleotide sequences.

Processivity: The ability of an enzyme to repetitively continue its catalytic function without dissociating from its substrate.

Protein: A biological molecule expressed by a gene and comprised of amino acids.

Purified: The term purified does not require absolute purity; rather, it is intended as a relative term. Thus, for example, a purified protein preparation is one in which the protein referred to is more pure than the protein in its natural environment within a cell.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are. Homologs or orthologs of a Y-family polymerase protein, and the corresponding cDNA sequence, will possess a relatively high degree of sequence identity when aligned using standard methods. This homology will be more significant when the orthologous proteins or cDNAs are derived from species which are more closely related (e.g., human and chimpanzee sequences), compared to species more distantly related (e.g., human and *C. elegans* sequences).

Methods of alignment of sequences for comparison are well known in the art. Various programs and alignment algorithms are described in: Smith & Waterman *Adv. Appl. Math.* 2:482, 1981; Needleman & Wunsch *J. Mol. Biol.* 48:443-53, 1970; Pearson & Lipman *Proc. Natl. Acad. Sci. USA* 85:2444-48, 1988; Higgins & Sharp *Gene,* 73:237-44, 1988; Higgins & Sharp *CABIOS* 5:151-53, 1989; Corpet et al., *Nuc. Acids Res.* 16:10881-90, 1988; Huang et al., *Computer Appls. in the Biosciences* 8:155-65, 1992; and Pearson et al., *Meth. Mol. Bio.* 24:307-31, 1994. Altschul et al. (*J. Mol. Biol.* 215: 403-10, 1990) present a detailed consideration of sequence alignment methods and homology calculations.

The NCBI Basic Local Alignment Search Tool (BLAST) (Altschul et al. *J. Mol. Biol.* 215:403-10, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI website, together with a description of how to determine sequence identity using this program.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence remains hybridized to a perfectly matched probe or complementary strand. Conditions for nucleic acid hybridization and calculation of stringencies can be found in Sambrook et al. (ed.), *Molecular Cloning: A Laboratory Manual,* 2$^{nd}$ ed., vol. 1-3, Cold Spring Harbor Laboratory Press, Cold Spring Harbor, N.Y., 1989, and Tijssen *Laboratory Techniques in Biochemistry and Molecular Biology—Hybridization with Nucleic Acid Probes* Part I, Chapter 2, Elsevier, N.Y., 1993.

Nucleic acid sequences that do not show a high degree of identity can nevertheless encode similar amino acid sequences, due to the degeneracy of the genetic code. It is understood that changes in nucleic acid sequence can be made using this degeneracy to produce multiple nucleic acid molecules that all encode substantially the same protein.

Thermostability: an enzyme that is thermostable is relatively unaffected by relatively high temperatures. In one specific, non-limiting example, a polymerase with a high degree of thermostability is unaffected by a temperature of at least 80° C., for example, 82° C., 85° C., 88° C., 90° C., 92° C., 95° C., or even higher temperatures.

Transfected: A process by which a nucleic acid molecule is introduced into cell, for instance by molecular biology techniques, resulting in a transfected cell. As used herein, the term transfection encompasses all techniques by which a nucleic acid molecule might be introduced into such a cell, including transduction with viral vectors, transfection with plasmid vectors, and introduction of DNA by electroporation, lipofection, and particle gun acceleration.

Translesion synthesis: Translesion synthesis is an important cellular mechanism to overcome replication blockage by DNA damage. To copy damaged DNA templates during replication, specialized DNA polymerases are required. In one specific, non-limiting example, a Y-family polymerase is used for translesion synthesis.

Translesion synthesis can be error-free or error-prone. From *E. coli* to humans, error-prone translesion synthesis constitutes a major mechanism of DNA damage-induced mutagenesis. As a response to DNA damage during replication, translesion synthesis contributes to cell survival and induced mutagenesis.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Y-family polymerase: Based on phylogenetic relationships, DNA polymerases can be broadly classified into five families. The A-family is typified by *E. coli* polymerase I; the B-family by *E. coli* polymerase II; the C-family by the *E. coli* polymerase III α-catalytic subunit; the D-family by archeal polymerases; and the X-family by eukaryotic polymerase β. Recently, a large number of new DNA polymerases have been identified, which although sharing significant amino acid sequence and similarity amongst themselves, exhibit little homology to any of the five previously identified polymerase families. This new family of polymerases has been described in the literature as the UmuC/DinB/Rev1/Rad30 superfamily. At the present time, these enzymes are best characterized in terms of their low-fidelity synthesis on undamaged DNA and their ability to bypass DNA lesions in vitro which normally block replication by members of the A-, B-, C-, D-, or X-family of polymerases. This family of polymerases has been re-named the Y-family of polymerases.

Many Y-family polymerases are known in the art. For a more thorough discussion of Y-family polymerases, see Ohmori et al., *Mol. Cell.* 8:7-8, 2001, which is herein incorporated by reference. In specific, non-limiting examples, a Y-family polymerase is Sac Dbh, Sso Dpo4, Dpo4LFDbh, DbhLFDpo4, AiLFSte (AiDpo4/SteDpo4LF), AiLFDpo4 (AiDpo4/SsoDpo4LF), *Acidianus infernus* Dpo4, *Stygiolobus azoricus* Dpo4, *Sulfurisphaera ohwakuensis* Dpo4, *Sulfolobus shibatae* Dpo4, *Sulfolobus tengchongensis* Dpo4, *Thermoascus aurantiacus* Pol eta, *Thermomyces lanuginosus* Pol eta, *Thermomyces lanuginosus* Pol iota, *Thermoascus aurantiacus* Pol iota, *Thermomyces lanuginosus* Pol kappa, or *Thermoascus aurantiacus* Pol kappa.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Provided herein are novel Y-family polymerases and chimeras that are particularly well adapted for the PCR amplification of ancient or degraded DNA samples, such as from an ancient biological sample, mitochondrial DNA or forensic samples (e.g., paraffin-embedded samples). The Y-family polymerases (and chimeras) disclosed herein can enhance PCR-based recovery of forensic DNA samples or ancient DNAs from extinct organisms by promoting replication past DNA lesions refractory to standard DNA polymerases. A number of replication-blocking DNA lesions are known to accumulate in unprotected (or poorly preserved) DNA as it ages, for instance, due to exposure to oxygen, background radiation, and other genotoxic agents. These types of lesions are thus prevalent in old forensic DNA samples and ancient DNA samples, making standard PCR-based analysis difficult. Inclusion of a lesion-bypassing Y-family polymerase along with a conventional thermostable polymerase in a PCR protocol designed to amplify old DNA samples can greatly increase recoverability, accuracy and length of products. Exemplary Y-family polymerases include *Acidianus infernus* Dpo4 (SEQ ID NO: 6), *Stygiolobus azoricus* Dpo4 (SEQ ID NO: 8), *Sulfurisphaera ohwakuensis* Dpo4 (SEQ ID NO: 10), *Sulfolobus shibatae* Dpo4 (SEQ ID NO: 12), *Sulfolobus tengchongensis* Dpo4 (SEQ ID NO: 14), *Thermoascus aurantiacus* Pol eta (SEQ ID NO: 41), *Thermomyces lanuginosus* Pol eta (SEQ ID NO: 43), *Thermomyces lanuginosus* Pol iota (SEQ ID NO: 45), *Thermoascus aurantiacus* Pol iota (SEQ ID NO: 47), *Thermomyces lanuginosus* Pol kappa (SEQ ID NO: 61), as well as the Dpo4LFDbh (SEQ ID NO: 2), DbhLFDpo4 (SEQ ID NO: 4), AiLFSte (AiDpo4/SteDpo4LF) (SEQ ID NO: 57), and AiLFDpo4 (AiDpo4/SsoDpo4LF) (SEQ ID NO: 59) chimeras.

In one embodiment, a Y-family polymerase is used independently to amplify damaged DNA. In another embodiment, a Y-family polymerase is combined with a standard thermostable polymerase, so as to promote bypass replication of inhibitory DNA lesions within the target molecule by the Y-family polymerase during the first one, a few or several rounds of thermocycling. Thereafter, the standard thermostable polymerase substantially or wholly takes over to complete the amplification process. Exemplary ratios of Y-family polymerase to standard thermostable polymerase include at least 1:1, such as at least 1:2, 1:5, 1:10, 1:25, 1:50, 1:100, 1:250, 1:500, and 1:1000, and such as at least 2:1, 5:1, 10:1, 25:1, 50:1, 100:1, 250:1, 500:1, and 1000:1.

In a specific, non-limiting example, one of the Dpo4 polymerases described herein (e.g., *Acidianus infernus* Dpo4 (SEQ ID NO: 6), *Stygiolobus azoricus* Dpo4 (SEQ ID NO: 8), *Sulfurisphaera ohwakuensis* Dpo4 (SEQ ID NO: 10), *Sulfolobus shibatae* Dpo4 (SEQ ID NO: 12), or *Sulfolobus tengchongensis* Dpo4 (SEQ ID NO: 14)) is used for a typical PCR protocol in place of a standard high-fidelity polymerase, such as Taq polymerase. The DNA is denatured, and a long first extension cycle is employed at approximately 60° C. (for instance, about 57° C. to about 63° C.) for approximately 30-60 minutes. After this extension cycle, a PCR thermocycling protocol is carried out as usual. Alternatively, this long extension step can be carried out at lower temperatures (for instance about 45° C. to about 55° C.) when one or more of the eukaryotic Y-family polymerases disclosed herein (e.g., *Thermoascus aurantiacus* Pol eta (SEQ ID NO: 41), *Thermomyces lanuginosus* Pol eta (SEQ ID NO: 43), *Thermomyces lanuginosus* Pol iota (SEQ ID NO: 45), *Thermoascus aurantiacus* Pol iota (SEQ ID NO: 47), or *Thermomyces lanuginosus* Pol kappa (SEQ ID NO: 61)) is used for the long extension step. In another specific, non-limiting example, a chimeric Y-family polymerase is used (e.g., Dpo4LFDbh (SEQ ID NO: 2), DbhLFDpo4 (SEQ ID NO: 4), AiLFSte (AiDpo4/SteDpo4LF) (SEQ ID NO: 57), or AiLFDpo4 (AiDpo4/SsoDpo4LF) (SEQ ID NO: 59)). In yet another specific, non-limiting example, a mixture of two or more of the Y-family polymerases (and/or chimeras) is used.

In a further, non-limiting example, Taq polymerase (or any other relatively high-fidelity polymerase) is added to the reaction mixture following the first extension cycle (which used the Y-family polymerase), and then a PCR thermocycling protocol is carried out as usual. In some embodiments, several PCR cycles are carried out with the Y-family polymerase(s) alone before a high-fidelity polymerase (or mixture of thereof) is added, for example 3-7 cycles (for instance 5 cycles) of 5-15 minutes each (for instance 10 minutes each). In yet a further, non-limiting example, a high-fidelity polymerase (e.g., Taq polymerase) and a Y-family polymerase are added to the reaction tube prior to the first extension cycle, and the entire PCR reaction is completed in a single "closed" reaction. The Taq polymerase (or another relatively high-fidelity polymerase) will compete with the Y-family polymerase for primer extension, but when it encounters a lesion in the template, it will terminate synthesis and fall off, allowing the Y-family polymerase to access the damaged DNA. Thus, the Y-family polymerases (and/or chimeras) disclosed herein, alone, or in combination with any other PCR enzyme, can amplify DNA targets that were previously "unamplifiable" or marginally amplifiable using conventional PCR methods.

In other embodiments, the Y-family polymerases (and chimeras) disclosed herein are used for making labeled DNA probes for molecular biology, either at high or low temperatures. The Y-family polymerases described herein are able to incorporate several different labeled DNA nucleotides into DNA during replication or primer extension. Thus, the novel Y-family polymerases disclosed herein provide a good substitute for Taq and other relatively high-fidelity polymerases in applications utilizing, for example, fluorescent nucleoside triphosphate derivatives or other labels. Such applications include, but are not limited to, production of fluorescent nucleic acid probes for DNA or RNA hybridization blots, DNA sequencing, flow sorting, fluorescence in situ hybridization, and microarray analysis.

In general, labeled nucleic acid molecules may be amplified using techniques well known to one of skill in the art, but a fluorescent derivative is substituted for an unmodified dNTP. The derivative can either be 100% substituted (i.e., all fluorescent or otherwise modified or labeled nucleotides), or used in a ratio (e.g., 1:100 of unmodified dNTP versus fluorescent dNTP), to generate an optimal fluorescent amplification product. In addition, many amplification techniques are automated and rely heavily on computer analyzed hybridization of fluorescent probes to specific genes or markers. By generating a probe with higher specific fluorescence, as is possible using the Y-family polymerases/chimeras described herein, the sensitivity of such assays is increased.

Furthermore, in addition to amplifying nucleotides while incorporating fluorescent or other labels, the Y-family polymerases/chimeras disclosed herein are also useful for amplifying a variety of other modified nucleotides and DNA analogues, for example, dinucleotide triphosphates, non-canonical base pairs (such as mispairs), as well as base analogues incorporated in the damaged or opposite strand to monitor structural and dynamic changes in the DNA. This approach also can be used to incorporate non-natural DNA nucleotides to expand the genetic "alphabet."

In still other embodiments, the biochemical characteristics of the Y-family polymerases disclosed herein can be altered, enhanced, or augmented to tailor their activities to suit specific applications by constructing chimeric proteins or using directed-evolution techniques. Exemplary chimeras include Dpo4LFDbh (SEQ ID NO: 2), DbhLFDpo4 (SEQ ID NO: 4), AiLFSte (AiDpo4/SteDpo4LF) (SEQ ID NO: 57), and AiL-FDpo4 (AiDpo4/SsoDpo4LF) (SEQ ID NO: 59). Dpo4 has been crystallized in a ternary complex with DNA and incoming nucleoside triphosphate. Therefore, the domain architecture of the enzyme is known, as are the residues likely to be important for DNA binding and substrate specificity. For example, the LF domain is important for DNA binding, whereas residues in the "fingers" domain are important for substrate specificity (Ling et al., Cell 107:91-102, 2001; Silvian et al., Nat. Struct. Biol. 8:984-89, 2001).

In the case of the LF domain, generation of such chimeras is demonstrated herein by swapping the LF of the poorly processive Dbh enzyme with the more processive Dpo4 enzyme, which creates a chimeric enzyme more Dpo4-like in its lesion bypass and processivity. Based upon the amino acid alignments of the various polymerases, it is clear where the "breakpoints" between the various sub-domains of the polymerase lie. For example, the LF domain of the Y-family polymerases disclosed herein starts at codons 245 (*Sulfolobus acidocaldarius* Dbh); 244 (*Sulfolobus solfataricus* Dpo4); 245 (*Acidianus infernus* Dpo4); 245 (*Stygiolobus azoricus* Dpo4); 244 (*Sulfurisphaera ohwakuensis* Dpo4); 244 (*Sulfolobus shibatae* Dpo4), and 244 (*Sulfolobus tengchongensis* Dpo4). Thus, one specific example involves replacing the LF domain of the *Acidianus infernus* Dpo4 enzyme, which is less processive than *Sulfolobus solfataricus* Dpo4 or the *Sulfolobus tengchongensis* Dpo4, with the littler finger domain from either *Sulfolobus solfataricus* Dpo4 or *Sulfolobus tengchongensis* Dpo4, thereby creating a more robust polymerase. Similarly, the *Stygiolobus azoricus* Dpo4 and *Sulfurisphaera ohwakuensis* Dpo4 enzymes are poorly processive (like *Sulfolobus acidocaldarius* Dbh), but their activity is increased dramatically if the LF domain of either of these two enzymes is swapped with that from *Sulfolobus solfataricus* or *Sulfolobus tengchongensis*.

The same approach can be utilized to domain-swap the "fingers" domain. The *Acidianus infernus* Dpo4 enzyme has many beneficial properties (e.g., it is thermostable and performs well in PCR), but it does not bypass lesions as well as *Sulfolobus solfataricus* Dpo4 or *Sulfolobus tengchongensis* Dpo4. Thus, the *Acidianus infernus* fingers domain can be swapped with, for example, that from *Sulfolobus solfataricus* Dpo4 or *Sulfolobus tengchongensis* Dpo4 in order to create an enzyme that bypasses lesions well. In addition, a "DNA shuffling" approach can be used to create a better polymerase, or a polymerase with specific desired characteristics. This technique uses randomly sheared DNA from homologous organisms to generate chimeras with enhanced properties.

Another approach to modify the Y-family polymerases described herein is called "compartmentalized self-replication". In this technique, a Y-family polymerase gene (e.g. a Dpo4 gene) is used as a template for self replication in PCR For example, to "evolve" a polymerase that is better at bypassing a CPD, primers are designed to the Y-family polymerase gene in question that contain a CPD in the oligonucleotide. Enzymes that have evolved to bypass the CPD better are more efficiently amplified and then cloned and isolated. Several cycles are performed until the enzyme is much better at CPD bypass. Examples of this method can be found in, for example, Ghadassy et al. (*Nat. Biotechnol.* 22:755-59, 2004), which is incorporated by reference in its entirety. In addition to the Dpo4 polymerase, this approach can be used to perform compartmentalized self-replication of the fungal Pol eta, Pol iota and Pol kappa polymerases described herein.

Other applications for which the Y-family polymerases and chimeras disclosed herein are useful include, but are not limited to, labeling or tagging DNA, real-time PCR, detection of SNPs, mismatches or DNA lesions, mutagenic PCR, directed-evolution methods, and expanding the DNA "alphabet" utilizing non-natural nucleotides. In addition, any fragment of any of the Y-family polymerases disclosed herein can be used as part of a fusion protein.

IV. Chimeric Y-Family Polymerases

Although they share little primary amino acid sequence homology with DNA polymerases from other families, structural studies of two archaeal DinB-like polymerases, Dbh and Dpo4, and of the catalytic core of *Saccharomyces cerevisiae* Polη, reveal that they are topologically similar to classical polymerases in that they resemble a right hand and possess "fingers," "palm" and "thumb" sub-domains. In addition these polymerases possess a unique domain that has been termed the "little finger" (Ling et al., *Cell* 107:91-102, 2001), "wrist" (Silvian et al., *Nat. Struct. Biol.* 8:984-89, 2001) or "PAD" (polymerase associated domain) (Trincao et al., *Mol. Cell.* 8:417-26, 2001) domain. The thumb and finger domains are smaller than those found in high-fidelity polymerases, and in the ternary complex of Dpo4 with DNA and an incoming nucleotide, the primer-template is held between the thumb and little finger (LF) domains and buttresses against the finger domain (Ling et al., *Cell* 107:91-102, 2001). The importance of the LF-DNA contact is highlighted by the fact that a proteolytic fragment of Dpo4 which retains the fingers, palm and thumb sub-domains, but lacks the LF domain, is much less active than the full-length polymerase (Ling et al., *Cell* 107:91-102, 2001). Interestingly, the LF domain is the least conserved of the four domains in the Y-family polymerases, and it is hypothesized that such divergence may, in part, contribute to the assorted biochemical properties reported in the literature for the various Y-family polymerases (Ling et al., *Cell* 107:91-102, 2001).

To further investigate the role that the LF domain contributes to the overall enzymatic properties of Y-family polymerases, the fact that both structural and biochemical data are available for two closely related archaeal DinB-like polymerases, Dbh and Dpo4, was taken advantage of. Dbh (DinB homolog) was identified and cloned by Kulaeva et al. using degenerate PCR primers designed against the *E. coli* uwuC and dinB genes (*Mutat. Res.* 357:245-53, 1996). The genomic DNA used in those studies was from an archaeal strain obtained from the American Type Culture Collection (ATCC, Manassas, Va.) that was originally believed to be *Sulfolobus solfataricus* P1. However, the entire genome of *Sulfolobus acidocaldarius* has recently been determined and the ~2.5 kb dbh-containing sequence reported by Kulaeva et al. matches perfectly with the genomic sequence from *S. acidocaldarius*. Dbh therefore originates from *S. acidocaldarius*, not *S. solfataricus* P1. DNA polymerase IV (Dpo4) was identified in the genome of *Sulfolobus solfataricus* P2, through BLAST searches (Altschul et al., *J. Mol. Biol.* 215:403-10, 1990) of the complete P2 genome (She et al., *Proc. Natl. Acad. Sci. USA* 98:7835-40, 2001), using the dbh gene as a search query (Boudsocq et al., *Nucleic Acids Res.* 29:4607-16, 2001). Overall, the Dbh and Dpo4 proteins share 54% identity, yet the two polymerases exhibit different enzymatic properties (Boudsocq et al., *Nucleic Acids Res.* 29:4607-16, 2001; Gruz et al., *J. Biol. Chem.* 276:47394-401, 2001; Potapova, et al., *J. Biol. Chem.* 277:28157-66, 2002). Dpo4 is thermostable and exhibits robust polymerase activity. At high enzyme to template ratios it can synthesize more than 1 kb of DNA, thereby allowing it to substitute for Taq polymerase in PCR assays (Boudsocq et al., *Nucleic Acids Res.* 29:4607-16, 2001). In addition, the lesion bypass properties of Dpo4 are somewhat like that of the eukaryotic translesion polymerases, in that Dpo4 can bypass thymine-thymine cyclobutane pyrimidine dimers (CPDs) (Boudsocq et al., *Nucleic Acids Res.* 29:4607-16, 2001; Ling et al., *Nature* 424:1083-87, 2003; McCulloch et al., *Nature* 428:97-100, 2004) and abasic sites (Boudsocq et al., *Nucleic Acids Res.* 29:4607-16; Kokoska et al., *J. Biol. Chem.* 278:50537-45, 2003). In contrast, Dbh is a much more distributive polymerase when replicating undamaged DNA, and is unable to incorporate a base opposite a CPD and bypasses an abasic site with very low efficiency (Gruz et al., *J. Biol. Chem.* 276:47394-401, 2001; Potapova, et al., *J. Biol. Chem.* 277:28157-66, 2002; Zhou et al., *Mol. Cell.* 8:427-37, 2001).

Structural studies of the two polymerases reveal that, in addition to sharing high sequence homology, the fingers, palm and thumb domains of the proteins are virtually superimposable. Without being bound by theory, this suggests that the different enzymatic properties of the two enzymes lie more in their sequence-divergent and structurally mobile LF domains. For example, in the Dpo4-DNA complex, the linker connecting the thumb and LF domains interacts only with DNA (Ling et al., *Cell* 107:91-102, 2001). In the apo-form of Dbh, however, this linker is hydrogen bonded to the β-sheets in the palm domain, as well as the β-sheets in the LF domain, thereby pinning the LF domain to the catalytic core (Silvian et al., *Nat. Struct. Biol.* 8:984-89, 2001). In order for Dbh to bind substrate, this linker has to peel off from the palm domain to allow the LF domain to reorient.

Figure 1:
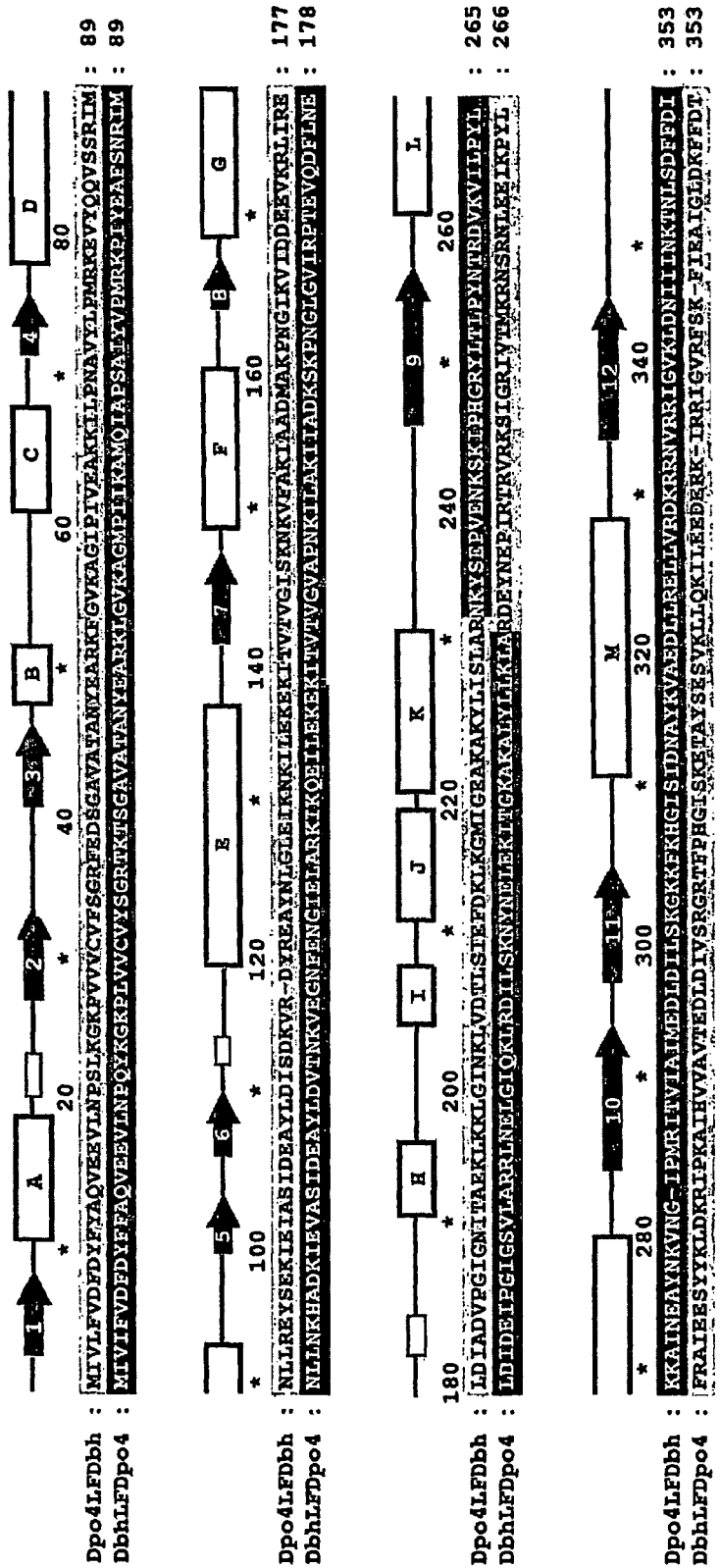
FIG. 1 is a diagram showing the alignment of the Dpo4LFDbh (SEQ ID NO: 2) and DbhLFDpo4 (SEQ ID NO: 4) chimeras. The secondary structures of the finger (~residues 11-78), thumb (~residues 164-231), palm (~residues 1-10 & 79-163), and LF (~residues 232-353) domains are indicated as boxes (α-helices) and arrows (β-sheets) above the aligned primary amino acid sequence. The primary amino acid sequence of the *Sulfolobus solfataricus* Dpo4 (Sso) is shown in a black typeface, while that of *Sulfolobus acidocaldarius* Dbh (Sac) is shown in a white typeface. Dpo4LFDbh consists of Sso Dpo4 finger, palm and thumb residues and the LF domain from Sac Dbh. DbhLFDpo4 consists of Sac Dbh finger, palm and thumb residues and the LF domain of Sso Dpo4.

To investigate the role that the LF domain plays in determining the enzymatic properties of Y-family polymerases in general, Dbh-Dpo4 chimeras were constructed in which the LF domains and the preceding linker have been interchanged (FIG. 1). Exemplary chimeras include Dpo4LFDbh (SEQ ID NO: 2), DbhLFDpo4 (SEQ ID NO: 4), AiLFSte (AiDpo4/SteDpo4LF) (SEQ ID NO: 57), and AiLFDpo4 (AiDpo4/SsoDpo4LF) (SEQ ID NO: 59). Studies revealed that by replacing Dpo4's LF domain with that from Dbh, the enzyme became more "Dbh-like." Conversely, by replacing Dbh's LF with that of Dpo4, the enzyme became more "Dpo4-like," indicating that the LF domain is a major factor in determining the physical and enzymatic properties of each polymerase. These observations are discussed herein in light of the crystal structure of Dbh and of various Dpo4-DNA complexes.

V. Cloning Novel Y-Family Polymerases

In addition, disclosed herein are several novel Y-family polymerases, including: *Acidianus infernus* Dpo4 (SEQ ID NO: 6), *Stygiolobus azoricus* Dpo4 (SEQ ID NO: 8), *Sulfu-* *risphaera ohwakuensis* Dpo4 (SEQ ID NO: 10), *Sulfolobus shibatae* Dpo4 (SEQ ID NO: 12), and *Sulfolobus tengchongensis* Dpo4 (SEQ ED NO: 14). Not only do these enzymes each have unique physical and enzymatic properties useful in, for instance, research and medical applications, but each of these Y-family polymerases also can be used to make chimeric Y-family polymerases that have still more unique physical and enzymatic properties.

By mutating or replacing the LF domains of these and other Y-family polymerases, polymerases can be created with the characteristics needed for a particular application. For example, altering the LF domain using the methods disclosed herein, a polymerase can be created that has a particular thermostability, fidelity, processivity, or ability to carry out translesion synthesis.

In addition to mutating or replacing the LF domain, the finger domain can be mutated or replaced with another Y-family polymerase finger domain. The finger domain is important as it makes a "substrate-lid." Some of the Y-family polymerases have a more open or closed active site and may or may not be able to accommodate a variety of lesions or nucleoside analogs. Mutant or chimeric Y-family polymerases can also be created in which both the finger and LF domains have been mutated or replaced with domains from other Y-family polymerases.

Furthermore, processivity of the Y-family polymerases can be increased by modifying the PCNA binding site on the polymerase. PCNA is a "sliding-clamp" that helps to hold the polymerase on to DNA. The appropriate binding sites can be engineered into the chimeras so as to increase processivity at high temperature.

Several additional newly-identified Y-family polymerases are disclosed herein as well, for example *Thermoascus aurantiacus* Pol eta (SEQ ID NO: 41), *Thermomyces lanuginosus* Pol eta (SEQ ID NO: 43), *Thermomyces lanuginosus* Pol iota (SEQ ID NO: 45), *Thermoascus aurantiacus* Pol iota (SEQ ID NO: 47), and *Thermomyces lanuginosus* Pol kappa (SEQ ID NO: 61). Because the functions and properties of human and yeast Pol eta are so well conserved, these enzymes have properties similar to other Pol eta family members. In addition, because these newly-identified Y-family polymerases originate in organisms that grow at relatively high temperatures (for example, approximately 45-50° C.), they are good candidate polymerases for protocols requiring thermostability.

These newly-identified Pol eta, Pol iota and Pol kappa polymerases can be used to form chimeric molecules with each other, as well as with other fungal or yeast Pol eta, iota and kappa genes. Using an approach similar to that described for the other Y-family polymerases described herein, one or more domains, for example a LF domain, can be swapped between the Pol eta (or iota/kappa) polymerases in order to create chimeric polymerase with a desired processivity and/or thermostability.

The following examples are provided to illustrate certain particular features and/or embodiments. These examples should not be construed to limit the invention to the particular features or embodiments described.

EXAMPLES

Example 1

Chimeric Y-Family Polymerases

This example describes the design and construction of chimeric Y-family polymerases.

Overproduction of *Sulfolobus acidocaldarius* Dbh

The dbh gene from *Sulfolobus acidocaldarius* was PCR-amplified from pOS21 (Kulaeva et al., *Mutat. Res.* 357:245-

53, 1996) with two oligonucleotides, ssdbhbam 5'-CGC GGA TCC TTA AAT GTC GAA GAA ATC AGA TAA ATT TG-3' (SEQ ID NO: 32) and ssdbhbsp: 5'-CAT GTC ATG ATA GTG ATA TTC GTT GAT TTT G-3' (SEQ ID NO: 33) containing a BamHI and BspHI restriction enzyme site respectively. The ~1050 bp PCR fragment was digested with BamHI and BspHI and the fragment gel purified before cloning into pET16b (Novagen, Madison, Wis.) digested with NcoI and BamHI. The sequence of the dbh gene in the recombinant plasmid, called pJM349, was verified and subsequently introduced into E. coli strain RW382, a ΔumuDC595::cat derivative of BL21(λDE3) (McDonald et al., Proc. Natl. Acad Sci. USA 95:1478-83, 1998).

Generation of DbhLFDpo4 and Dpo4LFDbh Chimeras

Native Sulfolobus acidocaldarius Dbh is a 354 amino acid protein with an estimated pI of 9.37. Sulfolobus solfataricus Dpo4 is two amino acids shorter and has an estimated pI of 9.11. Alignment of the two primary amino acid sequences reveals that although both proteins originate from related Sulfolobaceae, they only share 54% identity overall. Interestingly, most identity is found in the fingers, palm and thumb sub-domains of the polymerases, which are 59% identical. In contrast, the LF domain is least conserved, with only 41% primary amino acid sequence identity (FIG. 1). To investigate the role that the LF domain plays in the enzymatic properties of Y-family polymerases, chimeric proteins were constructed in which the respective LF domains and the flexible linker that tethers it to the thumb domain were interchanged (FIG. 1).

The first step toward generating Dbh/Dpo4 chimeras was to introduce a unique restriction enzyme site at the junction of the of the LF domain in Dpo4. This was achieved by site-directed mutagenesis (Quick Change, Stratagene, La Jolla, Calif.) of Leu228 (CTA→CTG) and Ala229 (GCT→GCC) codons, so as to produce a novel BalI/MscI restriction enzyme site within the Dpo4 gene. The BalI/MscI restriction site was generated in the Dpo4 over-expressing plasmid, p1914 (Boudsocq et al., Nucleic Acids Res. 29:4607-16, 2001) using oligonucleotides P2SWDW: 5'-CTC GTC TCT GGC CAG AGA GAT CAA ATA TTT AGC C-3' (SEQ ID NO: 34) and P2SWUP: 5'-TTG ATC TCT CTG GCC AGA GAC GAG TAT AAC GAG CC-3' (SEQ ID NO: 35) and gave rise to plasmid p1941. Chimeras were subsequently generated by domain swapping as follows: an ~700 bp NdeI-BalI/MscI fragment was amplified using pJM349 (Dbh) DNA as a template with primers P1ndelup: 5'-GGG GGG CATATG ATA GTG ATA TTC GTT GAT-3' (SEQ ID NO: 36) and P1bal2dw: 5'-GGG GGG ATT CTTGGCCAA CTT TAG TAG ATA TAA GGC TAA GGC-3' (SEQ ID NO: 37) (NdeI and BalI/MscI restriction sites are underlined). The amplicon was then digested with NdeI and BalI/MscI and cloned into the similarly digested plasmid, p1941. The resulting plasmid, called p1947, therefore expresses a chimeric polymerase consisting of the thumb, finger and palm domains of Dbh, and the LF domain of the Dpo4 polymerase (DbhLFDpo4; SEQ ID NO: 4) (FIG. 1).

A second plasmid, p1946, expressing the thumb, finger and palm domains of Dpo4 and the LF domain of the Dbh polymerase (Dpo4LFDbh; SEQ ID NO: 2) (FIG. 1) was obtained by amplification of a dbh fragment from pJM349 with oligonucleotides P1balIup: 5'-GGG AAG TTGGCCAGA AAT AAA TAT AGT-3' (SEQ ID NO: 38) and P1bam2dw: 5'-CCC CCC GGATCC TTA AAT GTC GAA GAA ATC AGA-3' (SEQ ID NO: 39) containing BalI/MscI and BamHI sites respectively (underlined). The amplicon was digested with BamHI and BalI/MscI and cloned into the similarly digested p1941 plasmid. The sequence of the chimeric Dpo4LFDbh and DbhLFDpo4 genes in p1946 and p1947, respectively, were verified and the plasmids were subsequently introduced into RW382.

Generation of AiLFSte (AiDpo4/SteDpo4LF) and AiLFDpo4 (AiDpo4/SsoDpo4LF) Chimeras The AiLFSte (AiDpo4/SteDpo4LF) (SEQ ID NO: 57) and AiLFDpo4 (AiDpo4/SsoDpo4LF) (SEQ ID NO: 59) chimeras consist of the finger, thumb and palm domain from the Acidianus infernus Dpo4 and LF domain from the Sulfolobus tengchongensis Dpo4 or the Sulfolobus solfataricus Dpo4, respectively. These chimeras were prepared in a manner similar to the Dbh/Dpo4 chimeras described herein. Briefly, a BalI/MscI restriction site was generated in the Acidianus infernus dpo4 gene using oligonucleotides Ai_FMsc711: 5'-TAT TCT CTGGCCAAC AAT ACC TAT GCT GAA CCG-3' (SEQ ID NO: 73) and Ai_RMsc667: 5'-GGT ATT GT TGGCCAG AGA ATA CAA GTA ACT AGC-3' (SEQ ID NO: 74), and generated in the Sulfolobus tengchongensis dpo4 gene using oligonucleotides Ste_FMsc708b: 5'-TTC TCG CTGGCCAGA GAT GAA TAT TMT GAA CCA-3' (SEQ ID NO: 75) and Ste_RMsc644: 5'-TTC ATC TCT GGC CAG CGA GAA TAA GTA ATT AGC-3' (SEQ ID NO: 76). The LF domain of the Acidianus infernus dpo4 gene was then replaced from the BalI/MscI site to the BamHI site with either the Sulfolobus tengchongensis dpo4 BalI/MscI to BamHI LF domain fragment, or the Sulfolobus solfataricus dpo4 BalI/MscI to BamHI LF domain fragment to create the AiLFSte (AiDpo4/SteDpo4LF) (SEQ ID NO: 57) or the AiLFDpo4 (AiDpo4/SsoDpo4LF) (SEQ ID NO: 59) chimeras.

Purification of Dpo4, Dbh, and Chimeric Proteins

The protocol utilized to purify all of the polymerases was based upon that described for Sulfolobus solfataricus Dpo4 (Boudsocq et al., Nucleic Acids Res. 29:4607-16, 2001), but includes several modifications. Although all of the recombinant genes are under the control of an IPTG-inducible T7 promoter (in the parental pET vector), significant expression of the recombinant proteins was found in the absence of induction. Furthermore, the Sulfolobaceae proteins are very stable in E. coli and significant quantities of the recombinant proteins was recovered by simply harvesting uninduced stationary phase overnight cultures of RW382 harboring the Dpo4/Dbh-expressing plasmids. Soluble cell extracts were made, but the heat-denaturation step that removes significant quantities of the thermolabile E. coli proteins was reduced from 85° C. to 75° C. for 5 min. Each polymerase was purified to homogeneity in three chromatographic steps using HiTrapQ, Hydroxylapatite and Mono S columns, except that the phosphate buffer used in the HiTrapQ column was replaced by a 20 mM HEPES buffer at pH 7.0, containing 100 mM NaCl, 1 mM DTT and 0.1 mM EDTA.

DNA Templates for in Vitro Primer Extension Assays

Most of the synthetic oligonucleotides used in the in vitro replication assays were synthesized by Lofstrand Laboratories (Gaithersburg, Md.) using standard techniques and were gel purified prior to use. Where utilized, the synthetic abasic site (dSpacer) was purchased from Glen Research (Sterling, Va.) and was incorporated into oligonucleotide templates using standard protocols by Lofstrand Laboratories (Gaithersburg, Md.). The exception was the cis-syn cyclobutane pyrimidine dimer-containing oligonucleotide that was synthesized and purified by Phoenix Biotechnologies (Huntsville, Ala.). Primers were 5'-labeled with [γ-$^{32}$P]ATP (5000 Ci/mmole; 1 Ci=37 GBq) (Amersham Biosciences, Piscataway, N.J.) using T4 polynucleotide kinase (Invitrogen, Carlsbad, Calif.). The sequence of each primer/template is given in the legend of the respective figure in which it was used. Single-stranded M13mp18 DNA was purchased from Invitrogen (Carlsbad, Calif.).

In Vitro Primer Extension Assays

Radiolabeled primer-template DNAs were prepared by annealing the 5'-[$^{32}$P]-labeled primer to the unlabeled template DNA at a molar ratio of 1:1.5. Standard 10 μl reactions contained 40 mM Tris•HCl at pH 8.0, 5 mM MgCl$_2$, 100 μM of each ultrapure dNTP (Amersham Biosciences, Piscatway, N.J.), 10 mM DTT, 250 μg/ml BSA, 2.5% glycerol, and 10 nM primer-template DNA. The concentration of polymerase added varied and is given in the respective figure legend. After incubation at 37° C. or 60° C. for various times, reactions were terminated by the addition of 10 μl of 95% formamide/ 10 mM EDTA and the samples heated to 100° C. for 5 min and briefly chilled on ice. Reaction mixtures (5 μl) were subjected to polyacrylamide/8 M Urea gel electrophoresis and replication products visualized by PhosphorImager analysis.

Forward Mutation Assay

Reaction mixtures (30 μl) contained 1 nM gel-purified M13mp2 gapped DNA substrate, 40 mM Tris•HCl (pH 9.0 at 22° C.), 5 mM MgCl$_2$, 10 mM dithiothreitol, 7.5 μg bovine serum albumin, 2.5% glycerol and 1 mM each of dATP, dGTP, dCTP and dTTP. Polymerization reactions were initiated by adding 20 nM Dpo4LFDbh or 1.5 nM DbhLFDpo4, incubated at 70° C. for 1 hour and terminated by adding EDTA to 15 mM. DNA products were analyzed by agarose gel electrophoresis and assayed for the frequency of lacZ mutants as described by Bebenek et al. (*Methods Enzymol.* 262:217-32, 1995) and Kokoska et al. (*J. Biol. Chem.* 277: 19633-38, 2002). DNA samples from independent lacZ mutant phage were sequenced to identify the sequence changes generated during gap-filling synthesis. Error rates were calculated as described by Bebenek et al. (*Methods Enzymol.* 262:217-32, 1995) and Kokoska et al. (*J. Biol. Chem.* 277:19633-38, 2002).

Figure 2:
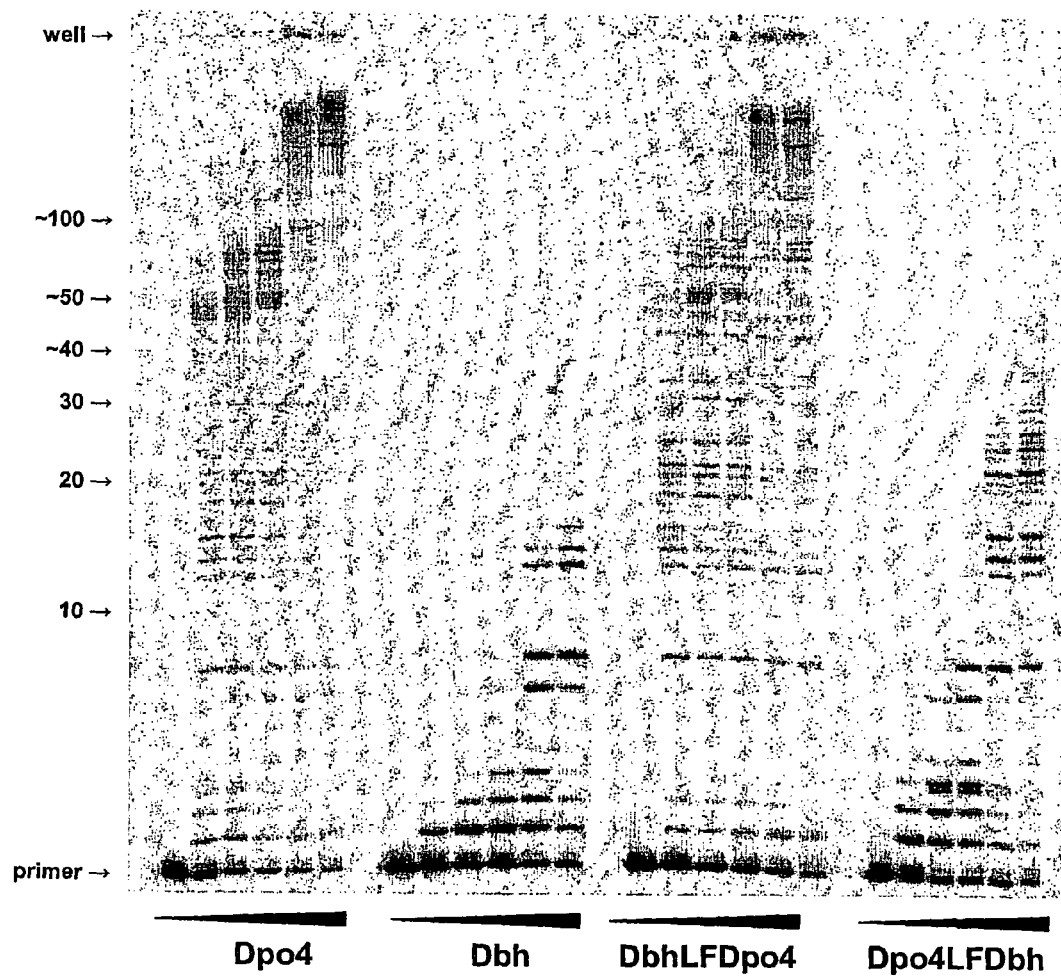
FIG. 2 is a digital image of a gel showing the ability of Sso Dpo4, Sac Dbh and the Dpo4LFDbh (SEQ ID NO: 2) and DbhLFDpo4 (SEQ ID NO: 4) chimeras to extend a radiolabeled 16-mer primer (5'-CTT GAA AAC ATA GCG A-3') (SEQ ID NO: 15) annealed to the single-stranded M13mp18 DNA (7.2 kb) (GenBank Accession No. M77815). The primer/template was fixed at 10 nM and elongation of the primer was assayed over a wide range of enzyme concentrations (0, 10 nM, 50 nM, 100 nM, 1 µM, 2 µM). Reactions contained all four dNTPs (100 µM each) and were performed for 5 minutes at 37° C. Replication products were separated on a 12%/8M Urea polyacrylamide gel and visualized by PhosphorImager analysis. Size markers are given on the left hand side of the figure.
Figure 3:
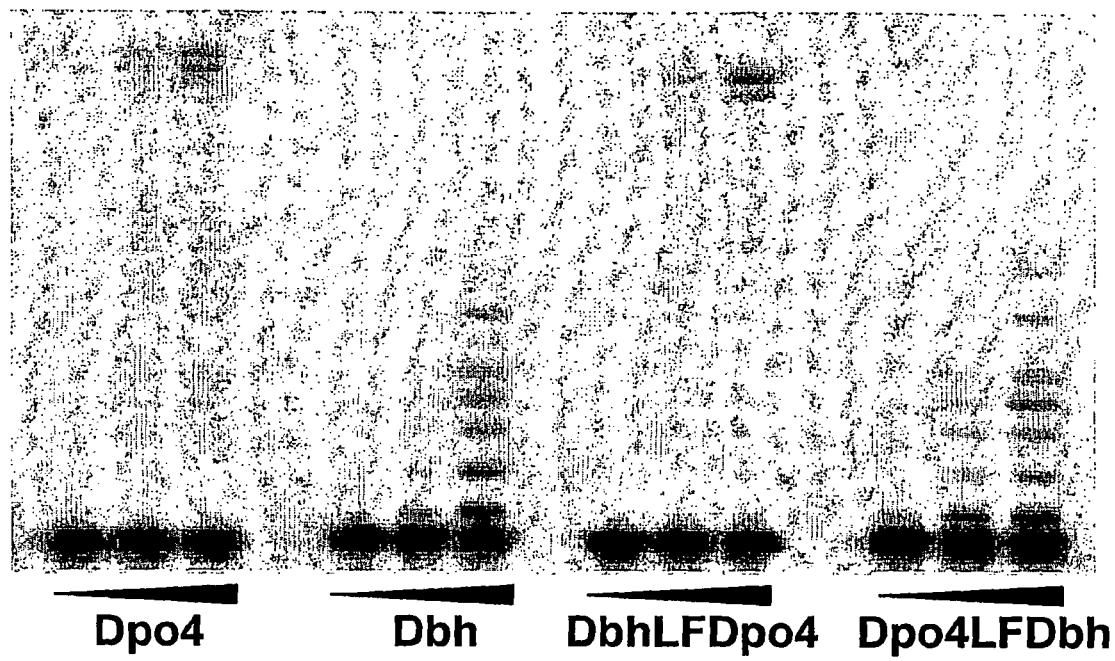
FIG. 3 is a digital image of a gel showing the processivity of Sso Dpo4, Sac Dbh and the Dpo4LFDbh (SEQ ID NO: 2) and DbhLFDpo4 (SEQ ID NO: 4) chimeras. Reactions were performed at 60° C. for 3 minutes in the presence of all four dNTPs (100 µM each) and contained 10 nM primer-template and limiting amounts of polymerase. The primer for these assays was a radiolabeled 23-mer (5'-GCG GTG TAG AGA CGA GTG CGG AG-3') (SEQ ID NO: 16) that was annealed to a 50-mer template (5'-CTC TCA CAA GCA GCC AGG CAA GCTCCGCACTCGTCTCTACACCGC TCC GC-3' (SEQ ID NO: 17), where the location of the annealed primer is underlined. The concentration of enzyme in these reactions varied considerably and was determined empirically so as to allow us to compare the size distribution of replication products under conditions where the percentage of primers extended was comparable between the four enzymes. The concentration of enzyme in the 10 µl reaction was as follows: Dbh; 0.2 nM, 0.8 nM and 3.3 nM: DbhLFDpo4; 0.03 nM, 0.17 nM and 0.83 nM: Dpo4; 0.017 nM, 0.08 nM and 0.4 nM; Dpo4LFDbh; 5.5 nM, 7.7 nM and 11 nM. Based upon these assays, both Sso Dpo4 and DbhLFDpo4 are more processive than either Sac Dbh or Dpo4LFDbh.

Size Distribution of Replication Products Synthesized by Native and Chimeric Dpo4 and Dbh Polymerases In vitro replication reactions with Y-family polymerases have clearly established that they are less processive than high-fidelity replicative polymerases. However, the absolute number of nucleotides incorporated per DNA binding event varies considerably among Y-family polymerases. For example, recent studies suggest that archaeal Dpo4 is more processive than human Polη (Kokoska et al., *J. Biol. Chem.* 278:50537-45, 2003). Indeed, when replicating circular M13 DNA at high enzyme to template ratios, Dpo4 synthesizes replication products that are several hundred nucleotides in length (FIG. 2). Under the same assay conditions, Dbh-dependent replication products are much shorter. Moreover, in contrast to Dpo4, adding a large molar excess of Dbh to the reaction does not dramatically change the size distribution of replication products on the circular M13 primer/template. The size distribution of replication products appears to be largely dependent upon the LF domain. Replacing the native LF domain of Dbh with that of Dpo4 leads to a dramatic increase in the size of the overall length of the replication products. Conversely, replacing the native LF domain of Dpo4 with that of Dbh reduces the size distribution of replication products from several hundred nucleotides at a 20-fold molar excess, to ~50 nucleotides or less at the same enzyme to template ratio (FIG. 2). Similar results were obtained in experiments performed at 60° C. with a shorter linear DNA template and a large molar excess of substrate over enzyme, so as to more accurately measure processivity of each enzyme during a single extension reaction (FIG. 3). Under reaction conditions where primer usage is minimal, full-length replication products are only observed in the presence of Dpo4 and the chimeric DbhLFDpo4, whereas those generated by either Dbh or Dpo4LFDbh, are considerably shorter. Based upon these observations, the respective LF domain of Dpo4/Dbh is the major factor determining the overall processivity of the two enzymes. Such conclusions are consistent with the crystallized ternary structure of Dpo4-DNA and incoming nucleotide, which revealed that Dpo4's LF domain in conjunction with the thumb domain wraps around DNA and helps hold the polymerase on to the primer-terminus (Ling et al., *Cell* 107: 91-102, 2001).

Figure 4A:
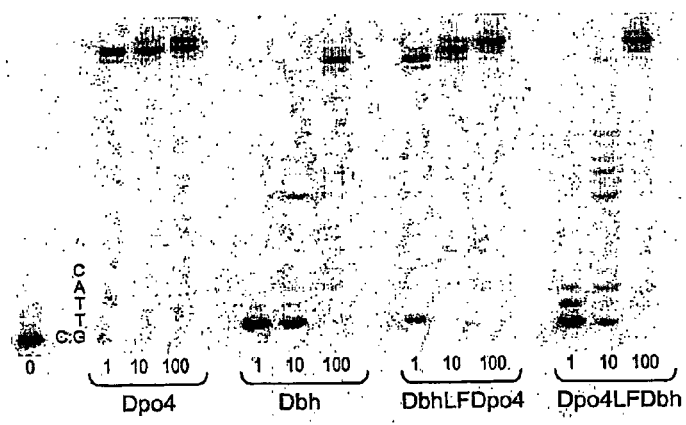
FIG. 4A is a digital image of a gel showing undamaged DNA.
Figure 4B:
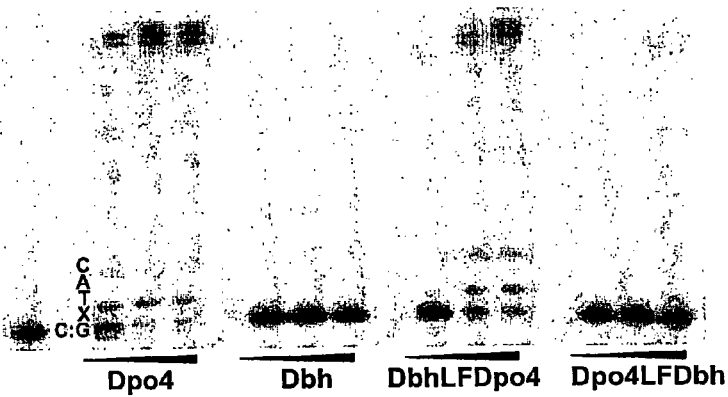
FIG. 4B is a digital image of a gel showing abasic site-containing DNA.
Figure 4C:
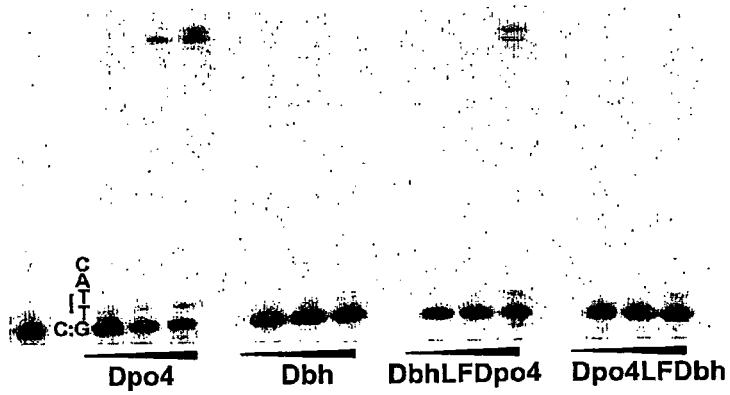
FIG. 4C is a digital image of a gel showing CPD-containing DNA. The complete sequence of the undamaged template was 5'-CTC TCA CAA GCA GCC AGG CAT TCT CCG CAC TCG TCT CTA CAC CGC TCC GC-3' (SEQ ID NO: 18). The 50-mer cis-syn dimer-containing template was identical, except that it contained a single CPD located at the adjacent Ts indicated in bold font. The 50-mer abasic (N)-containing template was 5'-CTC TCA CAA GCA GCC AGG CAT NCT CCG CAC TCG TCT CTA CAC CGC TCC GC-3' (SEQ ID NO: 19). All three templates were primed with a radiolabeled 23-mer with the following sequence 5'-GCG GTG TAG AGA CGA GTG CGG AG-3' (SEQ ID NO: 16) and replication products were separated on a 12%/8M Urea polyacrylamide gel and replication products visualized by PhosphorImager analysis.

Effect of LF Domain Swapping on Translesion DNA Synthesis of CPD and Abasic Sites Previous studies have shown that although Dpo4 is phylogenetically located in the DinB branch of the Y-family polymerases, it actually has enzymatic properties that are reminiscent of Polη-like enzymes, in that it can bypass cis-syn cyclobutane pyrimidine dimers (CPDs). The efficiency of Dpo4-dependent bypass of a CPD has been estimated to be approximately one tenth of that of human Polη (McCulloch et al., *Nature* 428:97-100, 2004). The reduced ability of Dpo4 to bypass a CPD compared to Polη appears to be largely due to stearic clashes between the 5'-T of the CPD and Dpo4, when the enzyme attempts to incorporate a nucleotide opposite the covalently linked 3'-T of the CPD (Ling et al., *Nature* 424: 1083-87, 2003). Nevertheless, the ability of Dpo4 to bypass a CPD is greater than that of the related Pol IV (Tang et al., *Nature* 404:1014-18, 2000), Pol kappa (Johnson et al., *Proc. Natl. Acad. Sci. USA* 97:3838-43, 2000; Ohashi et al., *Genes & Dev.* 14:1589-94, 2000; Zhang et al., *Nucleic Acids Res.* 28:4138-46, 2000) or Dbh polymerases (FIG. 4), which have little ability to incorporate a base opposite the 3'-T of the dimer. Likewise, Dpo4 can bypass a synthetic abasic site (Boudsocq et al., *Nucleic Acids Res.* 29:4607-16, 2001; Kokoska et al., *J. Biol. Chem.* 278:50537-45, 2003) (FIG. 4), yet Dbh only does so at high enzyme to template ratios and high levels of dNTPs (Potapova et al., *J. Biol. Chem.* 277: 28157-66, 2002) (FIG. 4). Similar to the results above with undamaged DNAs (FIG. 2 & FIG. 3), lesion bypass appears to depend upon the LF domain of the protein. While Dpo4 bypasses both CPDs and an abasic site, Dbh and the Dpo4LFDbh chimera showed only a limited ability to incorporate a base opposite either lesion even when they were present at a 10-fold excess of enzyme to template (FIG. 4). In contrast, replacing the Dbh LF domain with that of Dpo4 allowed the chimera to bypass an abasic site and a CPD, albeit with somewhat lower efficiency than wild-type Dpo4 (FIG. 4). These observations suggest that like Dpo4, the active site of Dbh can accommodate both adducts, but that the efficiency with which the chimeras bypass these lesions is largely determined by their LF domain.

Effects of LF Domain Swapping on Fidelity

Figure 5A:
(FIG. 5A) contained 30 nM Dbh, 75 nM Dpo4LFDbh, 5 nM Dpo4, and 10 nM DbhLFDpo4 respectively. Those performed at 60° C.
Figure 5B:
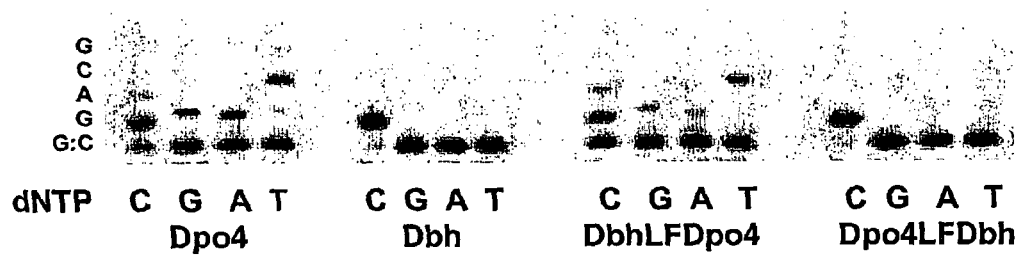
(FIG. 5B) contained 10 nM Dbh, 25 nM Dpo4LFDbh, 2.5 nM Dpo4 or 5 nM DbhLFDpo4. Products were resolved by denaturing polyacrylamide gel electrophoresis (8 M urea/15% acrylamide) and subsequently visualized using a Molecular Dynamics PhosphorImager.

Since the processivity and lesion-bypassing properties of the chimeras is strongly influenced by the LF domain, determining if the LF might also effect the fidelity of the enzymes when replicating undamaged DNA was also investigated. To examine this possibility, the pattern of insertion of each of the four nucleotides opposite template Guanine by Dpo4, Dbh and the LF chimeras in primer extension assays that were performed at 37° C. or 60° C. were analyzed. Similar to the temperature-dependent increase in catalytic activity reported for Dbh (Potapova et al., *J. Biol. Chem.* 277:28157-66, 2002), all four polymerases are more active at 60° C. as compared to 37° C. Using amounts of each enzyme yielding roughly similar levels of primer extension, it was found that at both temperatures, Dbh favors incorporation of correct dCMP rather than any of the three incorrect nucleotides, whereas Dpo4 extends the radiolabeled primer by one or more bases in the presence of either correct dCTP or any of the three incorrect dNTPs (FIG. 5). This difference in insertion specificity largely depends on the LF domain because Dpo4LFDbh gave a pattern similar to wild-type Dbh, whereas DbhLFDpo4 was more similar to Dpo4 than to Dbh. These qualitative misinsertion results at a single template nucleotide suggest that the LF domain can influence the fidelity with which Y-family polymerases replicate undamaged DNA.

To test this hypothesis quantitatively and at a large number of template positions, the effects of LF domain swapping on fidelity during synthesis of a 407-base single-stranded gap in M13mp2 DNA that contains the lacZ α-complementation gene sequence was determined. Base substitution, addition and deletion error rates for the two chimeric polymerases to those previously reported for Dpo4 using the same assay were compared (Kokoska et al., *J. Biol. Chem.* 277:19633-38, 2002). Owing to an inability to fill the lacZ gapped substrate with Dbh under any condition examined, for comparison to the other three enzymes, the error rates for Dbh obtained using a 203-base substrate containing the HSV-tk target gene were used (Potapova et al., *J. Biol. Chem.* 277:28157-66, 2002). Although the lacZ and HSV-tk gene sequences are not identical, both mutational targets score many different types of errors in numerous sequence contexts, such that overall average error rates are representative when considering major classes of events, as described herein. Results of the fidelity assays for all four polymerases are shown in Table 1.

TABLE 1

Fidelity of Dpo4, DbhLFDpo4, Dpo4LFDbh and Dbh polymerases.

|  | Dpo4 | DbhLFDpo4 | Dpo4LFDbh | Dbh |
|---|---|---|---|---|
| Total plaques | 6253 | 1782 | 4574 |  |
| Total mutants | 975 | 233 | 2077 |  |
| Frequency | $1.56 \times 10^{-1}$ | $1.31 \times 10^{-1}$ | $4.54 \times 10^{-1}$ | $1.7 \times 10^{-1}$ |
| Mutants sequenced | 182 | 78 | 68 | 46 |
| Total bases sequenced | 50050 | 21450 | 18700 | 7682 |
| Total seq changes | 476 | 154 | 140 | 290 |
| Changes/mutant | 2.6 | 2.0 | 2.1 | 6.3 |
| # of substitutions | 326 | 102 | 37 | 42 |
| # 1 bp deletions | 116 | 41 | 91 | 228 |
| # 1 bp additions | 9 | 5 | 1 | 3 |
| Other | 25 | 6 | 11 | 7 |
| Rate of substitutions | $6.5 \times 10^{-3}$ | $4.8 \times 10^{-3}$ | $2.0 \times 10^{-3}$ | $5.5 \times 10^{-3}$ |
| Rate 1 bp deletions | $2.3 \times 10^{-3}$ | $1.9 \times 10^{-3}$ | $4.9 \times 10^{-3}$ | $3.0 \times 10^{-2}$ |

Figure 6:
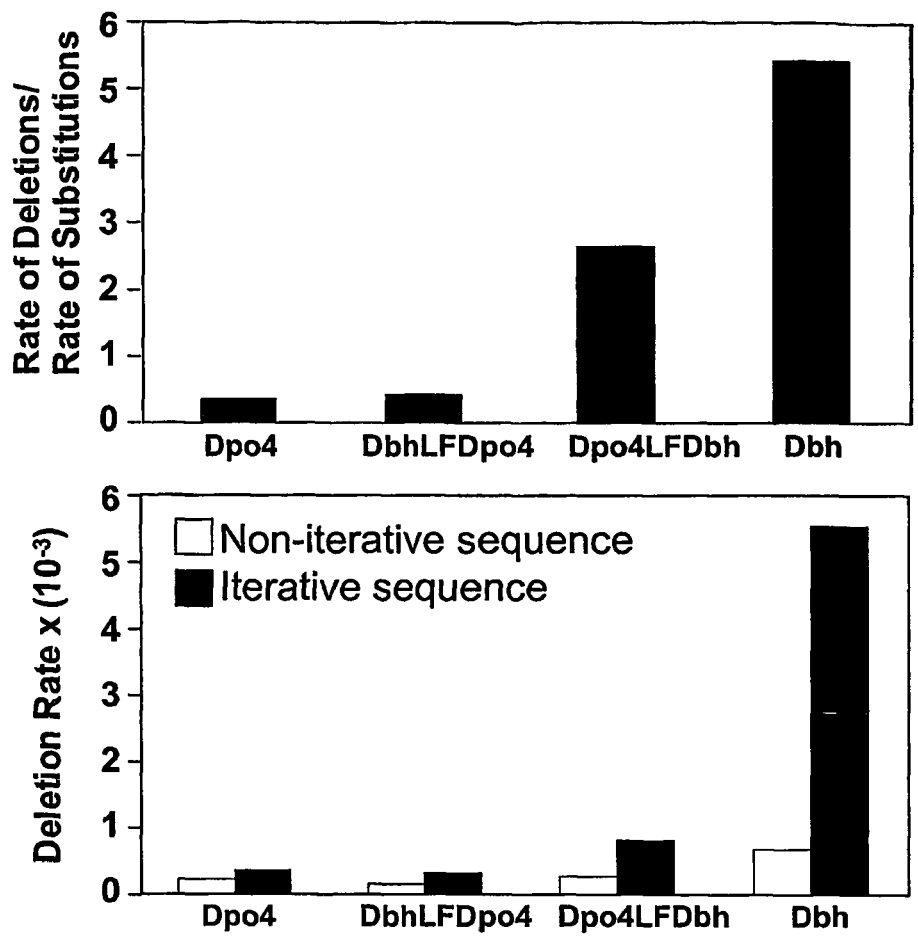
FIG. 6 is a pair of graphs showing the fidelity characteristics of Sso Dpo4, Sac Dbh, Dpo4LFDbh (SEQ ID NO: 2), and DbhLFDpo4 (SEQ ID NO: 4).

As reported by Kokoska et al. (*J. Biol. Chem.* 277:19633-38, 2002), Dpo4 has low fidelity and an average error rate for single-base deletions about 3-fold lower than for single base substitutions (FIG. 6A). When averaged for all 12 mispairs at many different template locations, the overall single-base substitution error rate of Dbh is similar to that of Dpo4 (Table 1; from Boudsocq et al., *Nucleic Acids Res.* 29:4607-16, 2001). However, Dbh is 13-fold less accurate than Dpo4 for single base deletions (Table 1), such that the ratio of single-base deletions to single-base substitutions (FIG. 6A) is much higher for Dbh (5.5 to 1) than for Dpo4 (0.35:1). Moreover, Dbh generates single-base deletions within repetitive sequence tracts at a rate that is about 8-fold higher than for single-base deletions of non-repeated nucleotides (FIG. 6B). In contrast, the Dpo4 rates for deleting iterated and non-iterated nucleotides differ by less than 2-fold. These results suggest that, despite their sequence homology and structural similarities, Dpo4 and Dbh differ in single-base deletion fidelity, with Dbh being particularly prone to deleting nucleotides in mononucleotide runs.

In this analysis, swapping the LF domains had little effect on the overall average single-base substitution error rates of Dpo4 and Dbh (Table 1). This does not exclude an effect of the LF on error rates for specific base substitutions at specific sites (as suggested by the data in FIG. 5). When the Dpo4 LF is swapped into Dbh, the ratio of the deletion to substitution rate is more similar to that of Dpo4 than Dbh (Table 1 and FIG. 6A), as are the error rates for deleting iterated and non-iterated bases (Table 1 and FIG. 6B). In contrast, when the Dbh LF is swapped into Dpo4, the ratio of deletion to substitution rate is higher (Table 1 and FIG. 6A), and the rate of deleting iterated bases is about 3-fold higher than the rate of deletion of non-iterated bases (Table 1 and FIG. 6B). The LF domains of Dpo4 and Dbh differentially influence error rates, primarily for deletion of single nucleotides, within repetitive sequences.

Structural Aspects of the LF Domain that Lead to DNA Binding and Translocation

Data presented herein shows that the LF domain of the polymerase has a significant effect on the processivity, fidelity and lesion-bypassing potential of the Y-family polymerases. By generating chimeras in which the LF domain of the Dpo4 and Dbh polymerases were interchanged, it was demonstrated that certain biochemical characteristics of the recombinant chimeras are similar to the polymerase from which the LF originated. For example, DbhLFDpo4 is similar to native Dpo4 in its processivity and ability to bypass a CPD or an abasic site. Conversely, swapping Dpo4's LF domain with that of Dbh (Dpo4LFDbh) reduces the catalytic activity of the enzyme on undamaged DNA and its ability to bypass a CPD and abasic site (FIGS. 2, 3 & 4). The fidelity results with undamaged DNA templates (FIG. 6; Table 1) indicate that error rates for single nucleotide deletions within repetitive sequences are differentially influenced by the identity of the LF domain. Dpo4LFDbh, which deletes single nucleotides within repetitive sequences at higher rates than Dpo4 is quite distributive (FIG. 3) and is unable to generate long DNA chains in reactions involving multiple cycles of DNA binding-synthesis-dissociation (FIG. 2). This correlation is noteworthy in light of extensive evidence with polymerases in other families (Bebenek et al., *Cold Spring Harb. Symp. Quant. Biol.* 65:81-91, 2000), suggesting that single-base deletion intermediates in repetitive sequences arise as the polymerase dissociates and/or reassociates with the primer-template. This suggests that for Y-family polymerases with generally low-fidelity for single-base deletion errors (Kokoska et al., *J. Biol. Chem.* 277:19633-38, 2002, and references therein), LF domain-specific interactions with the duplex primer-template region that control enzyme processivity, can also influence DNA strand alignment.

Alignment of the primary amino acid sequence of the Dpo4 and Dbh LF domains (residues 245-352 and 244-354, respectively) reveals that they are much less conserved than their catalytic cores (41% versus 59%), yet superposition of the LF domains in the Dpo4-DNA and apo-Dbh structures shows that the alpha-carbon backbone of the two domains is nearly indistinguishable (FIG. 7). However, despite their overall structural similarity, the LF domains of Dbh and Dpo4 differ in their surface curvature and electropotential. In particular, the LF domain of Dpo4 is more positively charged, especially at key residues shown to contact the DNA backbone in the Dpo4 ternary complex structures. These subtle changes, combined with the slightly different curvature of the surface, may alter the ability of the domain to interact with DNA. In addition, the linker region (residues 232-245) that connects the LF and thumb domains of each polymerase is highly variable and has a very different electrostatic potential. The 14 amino acid Dbh linker has an estimated pI of 8.6, but the corresponding region in Dpo4 is much more basic (estimated pI of 10), which may alter the interactions with a DNA substrate. Furthermore, the Dbh linker appears to be sandwiched between the β-sheets of both the palm and LF domains. This particular conformation would make it difficult for the LF to dissociate from the catalytic core of Dbh and to subsequently interact with DNA. In the absence of a crystal structure of apo-Dpo4, the possibility that in the absence of a DNA substrate, Dpo4 may also retract its LF domain in the same manner as Dbh, cannot be excluded.

Several structures of Dpo4 in a ternary complex with undamaged (Ling et al., *Cell* 107:91-102, 2001) and lesion-containing DNA (Ling et al., *Nature* 424:1083-87, 2003; Ling et al., *Mol. Cell.* 13:751-62, 2004; Ling et al., *PNAS* 101: 2265-69, 2004) have been solved. Comparison of these structures reveal that tertiary structures are very similar in nature with only modest variations in their finger, palm and thumb domains. There is, however, substantial movement in the LF domain to accommodate the various types of DNA lesions encountered. One of these structures (Ab-5) (Ling et al., *Mol. Cell.* 13:751-62, 2004), which depicts an abortive complex of Dpo4 attempting to replicate an abasic lesion, reveals that the Dpo4 LF undergoes a rotation of 54° and a 4.1 Å translation, similar in magnitude to the movement that would be required for the Dbh LF to dissociate from the catalytic core and to bind substrate. In the Ab-5 structure, the DNA template makes a "U-turn" and the base 3' to the abasic lesion becomes the template for replication. These observations suggest that the LF domain not only helps the polymerase bind to DNA, but physical movement of the domain also facilitates DNA translocation along the primer-template. Such observations are therefore in good agreement with findings that the LF domain plays an important role in determining the processivity of the polymerase (FIG. 4).

By making chimeras in which the LF domains of two closely related archaeal Y-family polymerases were interchanged, a hitherto pivotal role of the LF domain in determining the enzymatic properties of the enzymes has been uncovered. This includes effects on their processivity, ability to bypass template lesions, and their capacity to generate base-pair substitutions versus single-base deletions during low-fidelity DNA synthesis of undamaged DNA. The LF domain of Y-family polymerases is the least conserved among their four structural domains, but like the two diverged LF domains from Dpo4 and Dbh, they undoubtedly share common structural features. Therefore, just like Dpo4 or Dbh polymerases, subtle amino acid variations in the LF domains of the various polymerases likely contributes to a wide variety of enzymatic properties previously attributed to Y-family polymerases.

Example 2

Cloning of a Y-Family Polymerases from *Acidianus infernus, Stygiolobus azoricus, Sulfurisphaera ohwakuensis, Sulfolobus shibatae*, and *Sulfolobus tengchongensis*

This example describes the cloning of Y-family polymerases from *Acidianus infernus, Stygiolobus azoricus, Sulfurisphaera ohwakuensis, Sulfolobus shibatae*, and *Sulfolobus tengchongensis*. One of ordinary skill in the art will recognize that similar methods can be used to clone Y-family polymerases from other Archaea.

A set of degenerate primers were generated and used to obtain sequences 5'- and 3'- to dpo4 from *Acidianus infernus, Stygiolobus azoricus, Sulfurisphaera ohwakuensis, Sulfolobus shibatae*, and *Sulfolobus tengchongensis*. The degenerate primers are based on conserved sequences upstream (FIG. 8) and downstream (FIG. 9) of dpo4-like genes in *Sulfolobus acidocaldarius, Sulfolobus solfataricus* and *Sulfolobus tokodaii*. The consensus or "majority" amino acid sequence upstream and downstream of Dpo4 based on these three sequences is shown in FIGS. 8 and 9. To obtain an approximately 500 bp fragment of a 5'-section from *Acidianus infernus, Stygiolobus azoricus, Sulfurisphaera ohwakuensis, Sulfolobus shibatae*, or *Sulfolobus tengchongensis*, the following degenerate primers were used to amplify the consensus region DTTGAGD (SEQ ID NO: 22; see FIG. 8): 5'-CCG GAATTC GAY ACI ACI GGI GCI GGI GAY-3' (SEQ ID NO: 23) and 5'-GCC GCTCGAGTC IAD RWA IGC YTC RTC IAY ISW IRY-3' (SEQ ID NO: 24) (FIG. 10). To obtain an approximately 1100 bp fragment of a 3'-section from *Acidianus infernus, Stygiolobus azoricus, Sulfurisphaera ohwakuensis, Sulfolobus shibatae*, or *Sulfolobus tengchongensis*, the following degenerate primers were generated to amplify the consensus region YEDVEGG (SEQ ID NO: 25; see FIG. 9): 5'-CCG GAATTC RYI WSI RTI GAY GAR GCI TWY HTI GA-3' (SEQ ID NO: 26) and 5'-GCC G CTCGAGTA YGA RGA YGT IGA RGG IGG-3' (SEQ ID NO: 27) (FIG. 10).

The primers were incubated with DNA obtained from *Acidianus infernus, Stygiolobus azoricus, Sulfurisphaera ohwakuensis, Sulfolobus shibatae*, or *Sulfolobus tengchongensis*, and PCR amplification performed using standard methods. Briefly, the samples were thermocycled using the following reaction conditions: 95° C. for 30 seconds, 50° C. for 1 minute, 71° C. for 2 minutes, for a total of 55 cycles. The reaction mix included 50 µl Rx, 200-300 ng of DNA, 0.4 µM primer, and 3 mM MgCl2. The resulting PCR amplification products were sequenced, and gene specific primers designed to the start and end of the Dpo4-like gene from each organism. The primers designed also included restriction sites for subcloning the gene into an expression vector. They have an NdeI site at the start of the gene and a BamHI site at the 3'-end, so as to clone into pET22 derivatives.

Using the PCR conditions described above, the full-length Y-family polymerase gene from *Acidianus infernus* (SEQ ID NO: 5), *Stygiolobus azoricus* (SEQ ID NO: 7), *Sulfurisphaera ohwakuensis* (SEQ ID NO: 9), *Sulfolobus shibatae* (SEQ ID NO: 11), and *Sulfolobus tengchongensis* (SEQ ID NO: 13) was re-amplified with a high fidelity PCR polymerase. An amino acid alignment of the polymerases is shown in FIG. 15.

Example 3

Cloning of Y-Family Polymerases from *Thermoascus aurantiacus* and *Thermomyces lanuginosus*

This example describes the cloning of Y-family polymerases from *Thermoascus aurantiacus* and *Thermomyces lanuginosus*.

Additional newly-identified Y-family polymerases are disclosed herein, including *Thermoascus aurantiacus* Pol eta (SEQ ID NO: 41), *Thermomyces lanuginosus* Pol eta (SEQ ID NO: 43), *Thermomyces lanuginosus* Pol iota (SEQ ID NO:

45), *Thermoascus aurantiacus* Pol iota (SEQ ID NO: 47), and *Thermomyces lanuginosus* Pol kappa (SEQ ID NO: 61). Because the functions and properties of human and yeast Pol eta are so well conserved, these enzymes have properties similar to other Pol eta family members. In addition, because these newly-identified Y-family polymerases originate in organisms that grow at relatively high temperatures (for example, approximately 45-50° C.), they are good candidate polymerases for protocols requiring or benefiting from thermostability. For example, the *Thermoascus aurantiacus* polymerases function optimally at approximately 49-52° C. and have a maximum operating temperature of about 61° C., while the *Thermomyces lanuginosus* polymerases function optimally at approximately 45-50° C. and have a maximum operating temperature of about 60° C. An example of the activity of the *Thermoascus aurantiacus* Pol eta (SEQ ID NO: 41) and *Thermomyces lanuginosus* Pol eta (SEQ ID NO: 43) polymerases is shown in Example 9.

These newly-identified Pol eta, Pol iota and Pol kappa polymerases can be used to form chimeric molecules with each other, as well as with other fungal or yeast Pol eta, iota and kappa genes. Using an approach similar to that described for the other Y-family polymerases described herein, one or more domains, for example a LF domain, can be swapped between the Pol eta (or iota/kappa) polymerases in order to create chimeric polymerase with a desired processivity and/or thermostability.

The *Thermoascus aurantiacus* Pol eta (SEQ ID NO: 41) and *Thermomyces lanuginosus* Pol eta (SEQ ID NO: 43) polymerases were isolated using degenerate PCR primers based on other fungal polymerase eta genes from *Aspergillus fumigatus, Aspergillus nidulans, Coccidioides posadasii, Gibberella zeae, Magnaporthe grisea*, and *Neurospora crassa*. The first degenerate primers that successfully PCR amplified a piece of these genes were based on the following two amino acid sequences: (D/N)(A/C)F(F/Y)AQCE (SEQ ID NO: 48) and DEVF(I/M)DL (SEQ ID NO: 49). Amino acids shown in the parentheses are alternative sequences used to generate the degenerate primers. Additional gene-specific PCR primers and additional degenerate PCR primers were designed, including primers based on the following amino acid sequences: GGKLG(E/D)Q (SEQ ID NO: 50) and GFEDG(V/T/I)(T/S/N) (SEQ ID NO: 51). Inverse PCR was employed to obtain the complete 5'-end of the *Thermomyces lanuginosus* gene. Inverse PCR was also used to obtain a portion of the *Thermoascus aurantiacus* 3'-end. Flanking sequence PCR was employed to complete the beginning and end of these genes.

The *Thermomyces lanuginosus* Pol iota (SEQ ID NO: 45) and *Thermoascus aurantiacus* Pol iota (SEQ ID NO: 47) polymerases were isolated using degenerate PCR primers based on other fungal polymerase iota genes from *Aspergillus fumigatus, Aspergillus nidulans, Coccidioides posadasii, Gibberella zeae, Magnaporthe grisea*, and *Neurospora crassa*. The first degenerate primers that successfully PCR amplified a piece of these genes were based on the following two amino acid sequences: DYDCFYA (SEQ ID NO: 52) and GEDLT(RKP)F (SEQ ID NO: 53). Amino acids shown in the parentheses are alternative sequences used to generate the degenerate primers. Additional sequences of the *Thermomyces lanuginosus* Pol iota gene and the *Thermoascus aurantiacus* Pol iota gene were obtained by performing flanking-sequence PCR as described by Sørensen et al. (*J. Virol.* 67:7118-24, 1993). The functions and properties of human and *Drosophila* polymerase iota are very different (e.g., human DNA polymerase iota bypasses a CPD inefficiently and with low-fidelity, whereas *Drosophila* Pol iota does so efficiently and accurately), and it is likely that *Thermomyces lanuginosus* Pol iota and *Thermoascus aurantiacus* Pol iota have properties similar to either lower eukaryotes (e.g., *Drosophila*) or higher eukaryotes (e.g., humans and mice). In addition, like other Y-family polymerases, they are good candidates for protocols requiring thermostability.

The *Thermomyces lanuginosus* Pol kappa (SEQ ID NO: 61) polymerase (partial) was isolated by performing degenerate PCR using primers that were based on the following two amino acid sequences: GVLTTCNY (SEQ ID NO: 77) [Funkappa_FRIDegen3 5'-CCG GAA TTC GGI GTI YTI ACI ACI TGY AAY TAY-3' (SEQ ID NO: 78)] and NKPNGQ (FY) (SEQ ID NO: 79) [Funkappa_RXhDegen2 5'-GCC GCT CGA GRW AYT GIC CRT TIG GYT TRT T-3' (SEQ ID NO: 80)]. Amino acids shown in the parentheses are alternative sequences used to generate the degenerate primers.

Example 4

Cloning Other Y-Family Polymerase Sequences

This example describes methods that can be used to identify Y-family polymerases from other organisms, such as other Archaea, for example, members of the phyla Crenarchaeota. As described herein in Example 2, *Acidianus infernus, Stygiolobus azoricus, Sulfurisphaera ohwakuensis, Sulfolobus shibatae*, and *Sulfolobus tengchongensis* Y-family polymerases were cloned using degenerate primers that recognize a consensus sequence upstream and downstream of dpo4. Using identical or similar methods, additional Y-family polymerases can be identified.

For example, using the two-step PCR approach described in Example 2, Y-family polymerases can be cloned from other organisms. Briefly, DNA of the desired organism is PCR amplified in the presence of SEQ ID NOs: 23 and 24 or SEQ ID NOs: 26 and 27 to obtain sequences 5'- and 3'- to the Y-family polymerase, respectively, using the PCR conditions described in Example 2. Based on the sequence of each of the resulting two products, gene-specific primers are designed to the start and end of the Dpo4-like gene. The primers can also include restriction sites for sub-cloning the gene into an expression vector. Using standard PCR conditions, a full-length Y-family polymerase gene is re-amplified using a high fidelity PCR polymerase.

A one-step PCR approach can also be used to clone other Y-family polymerases. Briefly, DNA of the desired Archaea organism is PCR amplified in the presence of two primers, for example, SEQ ID NOs: 23 and 27, under standard PCR conditions, such as those described in Example 2.

DNA does not need to be isolated from an organism prior to PCR amplification. In some examples, the organism is incubated directly with the PCR primers, dNTPs, and other PCR reagents. In other examples, isolated DNA is incubated with the PCR primers, dNTPs, and other PCR reagents.

One skilled in the art will understand that degenerate primers that vary from SEQ ID NOs: 23, 24, 26, and 27 can also be used to practice the methods disclosed herein. For example, other degenerate primers that vary from SEQ ID NOs: 23, 24, 26, and 27 by one, two, three, four, or more nucleic acid residues, can still retain the ability to amplify a consensus sequence.

Example 5

Expression of Y-Family Polymerase Sequences

This example describes the expression of Y-family polymerases and chimeras.

The newly-identified Y-family polymerase genes were expressed from an IPTG-inducible promoter. As expression of Dpo4 is "leaky" and significant amounts of the protein accumulate by simply growing cells overnight without, the newly-identified Y-family polymerases were also grown in this fashion. The *Acidianus infernus* (two separate cultures) and *Sulfolobus shibatae* cultures gave strong signals (FIG. 11; "M," marker and "C," strain without plasmid). Expression in the *Stygiolobus azoricus* and *Sulfurisphaera ohwakuensis* cultures was lower, but was increased by induction with IPTG (FIG. 12).

Example 6

Partial Purification via Heat Denaturation of *E. coli* Proteins

This example describes the partial purification of Y-family polymerases using heat denaturation.

Dpo4-like enzymes are thermostable and when expressed in *E. coli*, cell extracts can be enriched for the thermostable polymerase by simply heating a crude cell lysate to 70° C. for 10 minutes. This causes many of the endogenous *E. coli* proteins to denature and precipitate. The denatured proteins can be removed by centrifugation, leaving the desired thermostable polymerase in solution.

Following heat treatment and centrifugation, the *Acidianus infernus, Sulfolobus shibatae*, and *Sulfolobus tengchongensis*, extracts were applied to a 10 ml Hydroxyapatite Bio-Gel HTP Gel column (Bio-Rad, Hercules, Calif.), and were eluted in a 10 mM to 500 mM KHPO4 (pH 7.5) gradient The three peak Dpo4-like containing fractions were pooled and applied to a 50 mL HiPrep 26/10 desalting column (Amersham Biosciences, Piscatway, N.J.) and eluted with 20 mM NaCl, 20 mM Tris pH 7.5, 0.1 mM EDTA and 1 mM DTT. Six fractions containing the Dpo4-like enzyme were then loaded onto an 8.5 ml SP Sepharose HP column (Amersham Biosciences, Piscatway, N.J.) and eluted with a 20 mM to 1M NaCl gradient. A band of the right molecular weight for the corresponding new Y-family polymerases was visible in all four extracts (FIG. 13). The intensity and size of the polymerase changes in the various extracts and is consistent with the level of overall expression in the whole cell extract. The amount loaded corresponds to about 0.5-1.0 µg of the polymerase.

Several fractions containing pure Dpo4-like enzymes were pooled, concentrated and 10% glycerol added to a final concentration before samples were frozen for long-term storage at −80° C. Purification of the Dpo4-like enzymes from *Stygiolobus azoricus* and *Sulfurisphaera ohwakuensis* was identical to that described above, except that an additional HiLoad 26/60 Superdex 75 column (Amersham Biosciences, Piscatway, N.J.) was utilized as the final step of purification prior to pooling samples, adding glycerol and freezing for long term storage.

Example 7

Polymerase Assays

This example describes the polymerase activity of isolated Y-family polymerases (Dpo4), such as from *Acidianus infernus, Stygiolobus azoricus, Sulfurisphaera ohwakuensis*, and *Sulfolobus shibatae*.

Various amounts of the heat treated extract were included in replication assays (see Example 1). Purified *Sulfolobus solfataricus* Dpo4 was used as a standard. All four extracts have polymerase activity as measured by this assay (FIG. 14). This activity is roughly proportional to the amount of protein added to the reaction. The *Sulfolobus shibatae* Dpo4-polymerase is particularly active (FIG. 14).

Additional examples of the polymerase activity of *Acidianus infernus* Dpo4, *Sulfolobus shibatae* Dpo4, *Sulfolobus tengchongensis* Dpo4, *Thermoascus aurantiacus* Pol eta, *Thermomyces lanuginosus* Pol eta, and the AiLFSte (AiDpo4/SteDpo4LF) and AiLFDpo4 (AiDpo4/SsoDpo4LF) chimeras are shown in Example 9.

Example 8

Functional Characteristics of the Novel Y-Family Polymerases

This example describes some of the functional characteristics of the newly-isolated Y-family polymerases, such as *Acidianus infernus* Dpo4, *Stygiolobus azoricus* Dpo4, *Sulfurisphaera ohwakuensis* Dpo4, *Sulfolobus shibatae* Dpo4, and *Sulfolobus tengchongensis* Dpo4.

Y-family polymerases are characterized by their ability to bypass lesions in DNA that would otherwise block replication by high fidelity DNA polymerases. They are ubiquitous and are found in all kingdoms of life: bacteria, archaea and eukaryotes. Y-family polymerase from thermostable organisms are of particular interest because the enzymes isolated from such species tend to be more stable, easy to work with, and may have more utility in assays at higher temperature, such as PCR.

Two thermostable Y-family polymerases (Dbh and Dpo4 from Sulfolobaceae) have been identified. Both belong to the DinB branch of the Y-family, have been crystallized and have been extensively studied. As disclosed herein, five additional novel DinB-like genes from five different crenarchaeota have been identified using a degenerate PCR approach: *Acidianus infernus* dpo4 (SEQ ID NO: 6), *Stygiolobus azoricus* dpo4 (SEQ ID NO: 8), *Sulfurisphaera ohwakuensis* dpo4 (SEQ ID NO: 10), *Sulfolobus shibatae* dpo4 (SEQ ID NO: 12), and *Sulfolobus tengchongensis* dpo4 (SEQ ID NO: 14). As described herein in Example 1, the novel DinB-like genes were over-expressed in *E. coli* and the proteins purified employing a similar protocol to that which was described for *Sulfolobus solfataricus* Dpo4 (Boudsocq et al., *Nucleic Acids Res.* 29:4607-16, 2001), with several modifications. First, the crude protein extracts were heat-treated at 70° C. for 10 minutes and centrifuged to remove a majority of the heat labile *E. coli* proteins. Subsequently, the protein extracts were subjected to HPLC, first over a hydroxylapetite column and then over an SP Sepharose column and gel filtration column as a final "polishing" step. Each of the five purified DinB-like proteins is capable of inserting nucleotides to the 3'-hydroxyl of a DNA primer/template duplex at 60° C., demonstrating that they are thermostable DNA polymerases.

Functional characteristics of the five novel DinB-like enzymes were evaluated using the following methods:

Primer Extension Assay

Three template DNA molecules were designed for primer extension experiments. The first, designated HTU50, has the sequence 5'-CTC TCA CAA GCA GCC AGG CAN NCT CCG CAC TCG TCT CTA CAC CGC TCC GC-3' (SEQ ID NO: 55) and contains no damaged bases (i.e., NN=TT). The second template, designated HMTT50, has a sequence identical to that of HTU50, except that it contains a thymine-thymine cyclobutane pyrimidine dimer at positions 21-22 (i.e., NN=a TT CPD). The third template, designated HTX50, also has a sequence identical to that of HTU50, except that it contains thymine paired with an abasic site (X) at positions 21-22 (i.e., NN=TX). The primer designated SSHTP2 has the sequence 5'-GCG GTG TAG AGA CGA GTG CGG AG-3' (SEQ ID NO: 54) and was 5'-end-labeled with $^{32}$P (Lofstrand Laboratories, Gaithersburg, Md.).

Ten pmol of the $^{32}$P-labeled SSHTP2 primer was annealed with an excess (20 pmol) of one of the three templates by heating the mixture to 95° C. for five minutes in 100 µl of 1× annealing buffer (400 mM Tris pH 8.0, 50 mM MgCl$_2$, 5 µg/ml BSA and 14.2 mM 2-mercaptoethanol) and allowing the mixture to slowly cool to room temperature. Primer extension reactions were carried out using 10 nM labeled primer/template in 10 µl reactions containing 1× replication buffer (200 mM Tris pH 8.0, 25 mM MgCl$_2$, 1.25 mg/ml BSA, and 12.5% glycerol), 100 µM each dNTP, and various concentrations of polymerase. Dilutions of polymerase were made in 1× dilution buffer (25 mM Tris pH 7.9, 0.5 mM EDTA, 1 mM dithiothreitol, 0.05% NP-40, and 25% glycerol). For the lesion primer extension experiment, 10 nM of each Dpo4 polymerase was used and the reactions were incubated at 60° C. for 10 minutes. For the labeled nucleotide primer extension experiment 0.2 nM of each Dpo4 protein was used, while 1 µl of a 1 to 1000 dilution of Taq was used. In the reactions containing labeled nucleotides, 100 µM of the labeled dUTP nucleotides (biotin-aha-dUTP, fluorescein-aha-dUTP or Alexa Fluor® 647-aha-dUTP (Molecular Probes, Eugene, Oreg.)) or 100 µM of the Cy5-dCTP nucleotide (Amersham Biosciences, Piscataway, N.J.) replaced either dTTP or dCTP, respectively. The labeled nucleotide reactions were incubated at 60° C. for three minutes. To stop the reactions, 10 µl of 2× loading dye (95% formamide, 10 mM EDTA, 0.1% xylene cyanol and 0.1% bromophenol blue) was added and the reactions were incubated at 95° C. for five minutes and briefly chilled before loading 5 µl onto a 12% acrylamide/7 M urea sequencing gel.

FIG. 17 shows a set of gels that illustrate primer extension of undamaged and damaged templates by the Dpo4 enzymes from *Acidianus infernus*, *Stygiolobus azoricus*, *Sulfurisphaera ohwakuensis*, *Sulfolobus shibatae*, and *Sulfolobus tengchongensis*, with purified *Sulfolobus solfataricus* Dpo4 as a standard. The "undamaged" panel shows primer extension of the SSHTP2/HTU50 primer/template substrate by the various Dpo4 enzymes. The "CPD" panel shows primer extension of the SSHTP2/HMTT50 primer/template substrate containing a TT CPD dimer in the HMTT50 template. The "abasic" panel shows primer extension of the SSHTP2/HTX50 primer/template substrate containing an abasic site in the HTX50 template.

Under the assay conditions used, Ssh (Dpo4 from *Sulfolobus shibatae*), Ai (Dpo4 from *Acidianus infernus*), and Ste (Dpo4 from *Sulfolobus tengchongensis*) have properties similar to Sso (purified Dpo4 from *Sulfolobus solfataricus*) in their ability to efficiently extend primers to the very end of the undamaged DNA template. Soh (Dpo4 from *Sulfurisphaera ohwakuensis*) is less active, and Saz (Dpo4 from *Stygiolobus azoricus*) is much more distributive and only extends the primer by 2-3 nucleotides. On a CPD template, Ssh and Ste are able to bypass the lesion, but to a lesser extent than Sso Dpo4. Ai, Saz and Soh are unable to bypass a CPD lesion. On an abasic template, Ssh and Ste are able to bypass the lesion with a roughly similar efficiency as Sso Dpo4, whereas Ai, Saz and Soh are unable to bypass the lesion. Therefore, the novel polymerases have DNA polymerase activity, and while the enzymatic properties of the enzymes are similar (particularly for Ssh and Ste), each enzyme has its own unique properties.

Both the Ssh and Ste polymerases are comparable to Sso Dpo4 in activity with regard to processivity. The Ai polymerase is somewhat less processive than the Sso Dpo4, while the Saz and Soh polymerases are significantly less active and less processive than Sso Dpo4. The properties of the Saz and Soh polymerases are, in fact, more similar to Dbh than to Dpo4, and these properties may be due to certain amino acids in their structural LF domain. Furthermore, like Sso Dpo4, the Ssh, Ste and Ai polymerases are capable of replication past DNA lesions, such as abasic sites and CPD lesions. The ability to bypass such lesions is confined to Y-family polymerases, since these lesions usually block/terminate replication by other non-Y-family polymerases, such as human DNA polymerases alpha (Masutani et al., *EMBO J.* 19:3100-09, 2000) or delta (McCulloch et al., *Nucleic Acids Res.* 32:4665-75, 2004).

FIG. 18 shows a set of gels that illustrate labeled nucleotide incorporation by Dpo4 enzymes from *Acidianus infernus*, *Sulfolobus shibatae*, and *Sulfolobus tengchongensis*, with purified *Sulfolobus solfataricus* Dpo4 and Taq polymerase as standards, during primer extension. The "4 dNTPs" panel shows primer extension in the presence of all four unmodified nucleotides. The "biotin dUTP" panel shows primer extension where dTTP was replaced with biotin-aha-dUTP (Molecular Probes, Eugene, Oreg.). The "fluorescein dUTP" panel shows primer extension where dTTP was replaced with fluorescein-aha-dUTP (Molecular Probes, Eugene, Oreg.). The "Alexa fluor dUTP" panel shows primer extension where dTTP was replaced with Alexa Fluor® 647-aha-dUTP (Molecular Probes, Eugene, Oreg.). Lastly, the "Cy5 dCTP" panel shows primer extension where dCTP was replaced with Cy5-dCTP (Amersham Biosciences, Piscatway, N.J.).

These gels show that purified Sso Dpo4, Ssh, Ai, and Ste enzymes can all utilize the modified nucleoside triphosphates. Under the assay conditions used, Ai is the least efficient of the enzymes at incorporating modified nucleoside triphosphates. Sso and Ssh are similar to Taq, with Ste being somewhat better than Taq when using biotin dUTP and fluorescein dUTP. Although the primer was extended by Sso, Ssh, Ai, and Ste in the presence of Cy5-dCTP, there was a strong pause when encountering the adjacent Gs (5-6 bases from the 3'-end of the primer), indicating that the Dpo4 enzymes extend tandem Cy5-dCTPs, whereas Taq does not have this pause.

The Ssh, Ai, and Ste polymerases were able to incorporate several different labeled DNA nucleotides into DNA during replication. For all four of the labeled nucleotides, Ste Dpo4 was significantly more active than Taq in insertion of the labeled nucleotide and extension from the labeled nucleotide. In the Alexa Fluor® dUTP reactions, Sso Dpo4, Ssh Dpo4 and Ste Dpo4 were all better than Taq at completing extension of the primer. However, Taq was better that the Dpo4 polymerases at completing extension of the primer in the Cy5 reactions. Thus, the novel Dpo4 enzymes disclosed herein provide a good substitute for Taq polymerase in applications utilizing, for example, fluorescent nucleoside triphosphate derivatives.

PCR Reactions

Fifty microliter PCR reactions were carried out using 200 nM of each of the Dpo4 enzymes from *Acidianus infernus*, *Sulfolobus shibatae*, and *Sulfolobus tengchongensis* (with purified *Sulfolobus solfataricus* Dpo4 as a standard), or 2.5 units of Taq DNA polymerase (also as a standard; New England Biolabs, Beverly, Mass.) in 1× ThermoPol reaction buffer (20 mM Tris pH 8.8, 10 mM KCl, 10 mM (NH$_4$)$_2$SO$_4$, 2 mM MgSO$_4$ and 0.1% Triton X-100; New England Biolabs, Beverly, Mass.), using 1 µM of primers (Ste_FNde5 [5'-A AAA ACC AAA AGT TAT ATG CAT ATG AT-3' (SEQ ID NO: 81)] and Ste_RBam1089 [5'-TTA CCT CAA GGA TCC TAA GGA AAT TG-3' (SEQ ID NO: 82)]), 200 µM each of all four dNTPs and 10 ng of the circular plasmid pJM548 containing the 1.1 kb *Sulfolobus tengchongensis* Dpo4 gene. Thermocycling was performed as follows: 3 minutes at 85° C.

followed, by 35 cycles of 85° C. for 30 seconds (denaturation step) and 60° C. for 7 minutes (annealing and elongation steps).

Two microliters of the 50 µl reactions were electrophoresed through a 0.9% agarose gel and stained with ethidium bromide (FIG. 19). The gel shows that, under the assay conditions used, Sso Dpo4, Ai and Ste can all function in a "closed tube" PCR reaction, and that the reaction is sufficiently robust to amplify at least a 1.1 kb amplicon. Using the *Sulfolobus tengchongensis* Dpo4 gene as a template demonstrates that each of the enzymes can amplify DNA roughly the size of their own gene. This is useful for compartmentalized self replication, which can be utilized to modify the properties of the enzymes.

Example 9

Using Y-Family Polymerases to Amplify Ancient or Damaged DNA

This example illustrates the ability of the Y-family polymerases disclosed herein, such as *Acidianus infernus* Dpo4, *Sulfolobus shibatae* Dpo4, *Sulfolobus tengchongensis* Dpo4, *Thermoascus aurantiacus* Pol eta, *Thermomyces lanuginosus* Pol eta, and the AiLFSte (AiDpo4/SteDpo4LF) and AiLFDpo4 (AiDpo4/SsoDpo4LF) chimeras, to amplify ancient or damaged DNA.

Ancient DNA and/or forensic samples often have lesions that are refractory to PCR amplification by Taq (or any other high-fidelity DNA polymerase). As unprotected DNA ages, a number of replication-blocking DNA lesions accumulate due to exposure to oxygen, background radiation, and other genotoxic agents. Thus, these types of lesions are common in forensic and ancient DNA samples, making PCR-based analysis difficult. One such lesion is 5-hydroxy-5-methyl hydantoin, which is prevalent in ancient DNA. Inclusion of a lesion-bypassing Dpo4 polymerase along with a conventional thermostable polymerase in a PCR protocol designed to amplify old DNA or forensic DNA samples greatly increases recoverability, accuracy and length of amplification products.

The ability of *Acidianus infernus* Dpo4, *Sulfolobus shibatae* Dpo4, *Sulfolobus tengchongensis* Dpo4, *Thermoascus aurantiacus* Pol eta, *Thermomyces lanuginosus* Pol eta, and the AiLFSte (AiDpo4/SteDpo4LF) and AiLFDpo4 (AiDpo4/SsoDpo4LF) chimeras to amplify ancient or damaged DNA were evaluated using the following method:

Primer Extension Assay

Two template DNA molecules were designed for primer extension experiments. The first, designated HydU22, has the sequence 5'-CAC TTC GGA NCG TGA CTG ATC T-3' (SEQ ID NO: 62) and contains no damaged bases (i.e., N=T). The second template, designated ODN, has a sequence identical to that of HydU22, except that it contains a 5-hydroxy-5-methyl hydantoin adduct at position 10 (i.e., N=a hydantoin adduct). The primer designated SSHydP has the sequence 5'-AGA TCA GTC ACG-3' (SEQ ID NO: 63) and was 5'-end-labeled with $^{32}$P (Lofstrand Laboratories, Gaithersburg, Md.).

Ten pmol of the $^{32}$P-labeled SSHydP primer was annealed with an excess (20 pmol) of one of the two templates by heating the mixture to 95° C. for five minutes in 100 µl of 1× annealing buffer (400 mM Tris pH 8.0, 50 mM MgCl$_2$, 5 µg/ml BSA and 14.2 mM 2-mercaptoethanol) and allowing the mixture to slowly cool to room temperature. Primer extension reactions were carried out using 10 nM labeled primer/template in 10 µl reactions containing 1× replication buffer (200 mM Tris pH 8.0, 25 mM MgCl$_2$, 1.25 mg/ml BSA, and 12.5% glycerol), 100 µM each dNTP and the following concentrations of polymerase: Taq (standard), 1 µl of a 1 to 600 dilution; Sso Dpo4 (standard), 0.33 nM; Ste Dpo4, 0.75 nM; Ssh Dpo4, 1 nM; Ai Dpo4 0.5 nM; AiLFDpo4 (AiDpo4/SsoDpo4LF) chimera, 1.25 nM; AiLFSte (AiDpo4/SteDpo4LF) chimera, 1.25 nM; *Thermoascus aurantiacus* Pol eta and *Thermomyces lanuginosus* Pol eta, 100 ng of a 1 to 10 dilution of a soluble *E. coli* extract in which the eta polymerases were over-produced. Dilutions of polymerase were made in 1× dilution buffer (25 mM Tris pH 7.9, 0.5 mM EDTA, 1 mM dithiothreitol, 0.05% NP-40, and 25% glycerol). The reactions were incubated at 37° C. for 10 minutes. To stop the reactions, 10 µl of 2× loading dye (95% formamide, 10 mM EDTA, 0.1% xylene cyanol and 0.1% bromophenol blue) was added and the reactions were incubated at 95° C. for five minutes and briefly chilled before loading 5 µl onto a 12% acrylamide/7 M urea sequencing gel.

FIG. 20 shows a pair of gels that illustrate primer extension of undamaged and hydantoin containing templates by the Dpo4 enzymes from *Acidianus infernus*, *Sulfolobus shibatae*, *Sulfolobus tengchongensis*, and the AiLFSte (AiDpo4/SteDpo4LF) and AiLFDpo4 (AiDpo4/SsoDpo4LF) chimeras. The "undamaged" panel shows primer extension of the SSHydP/HydU22 primer/template substrate by the various Dpo4 enzymes and chimeric enzymes. The "Hydantoin" panel shows primer extension of the SSHydP/ODN primer/template substrate containing a 5-hydroxy-5-methyl hydantoin adduct in the ODN template.

FIG. 20 reveals that under the assay conditions used, Sso (purified Dpo4 from *Sulfolobus solfataricus*), Ste (Dpo4 from *Sulfolobus tengchongensis*), Ssh (Dpo4 from *Sulfolobus shibatae*), Ai (Dpo4 from *Acidianus infernus*), Ai/Sso (the AiLFDpo4 chimeric), and Ai/Ste (the AiLFSte chimeric) are able to bypass the hydantoin lesion with roughly similar efficiency, while Taq DNA polymerase is significantly less able to bypass this lesion. Ai Dpo4 exhibits a reduced processivity, both on the undamaged and the hydantoin containing template, relative to the other Dpo4 enzymes. However, the chimeric enzymes, in which the Ai LF domain has been replaced with either the LF domain from Sso or Ste, have a much enhanced processivity on both the undamaged and the hydantoin containing template, relative to native Ai Dpo4.

FIG. 21 shows a pair of gels that illustrate primer extension of undamaged and hydantoin containing templates by the *Thermoascus aurantiacus* Pol eta and *Thermomyces lanuginosus* Pol eta enzymes. The "undamaged" panel shows primer extension of the SSHydP/HydU22 primer/template substrate by the *Thermoascus aurantiacus* Pol eta and *Thermomyces lanuginosus* Pol eta enzymes. The "Hydantoin" panel shows primer extension of the SSHydP/ODN primer/template substrate containing a 5-hydroxy-5-methyl hydantoin adduct in the ODN template. FIG. 21 reveals that under the assay conditions used, Ta (Pol eta from *Thermoascus aurantiacus*) and Tl (Pol eta from *Thermomyces lanuginosus*) are both DNA polymerases and, similar to the Dpo4 enzymes, are both capable of bypass replication past a hydantoin lesion.

This disclosure provides thermostable Y-family polymerases, in particular several novel Y-family polymerases and chimeras made therefrom, as well as methods of identifying other Y-family polymerases and methods of generating other chimeric Y-family polymerases. It will be apparent that the precise details of the methods described may be varied or modified without departing from the spirit of the described invention. We claim all such modifications and variations that fall within the scope and spirit of the claims below.

We claim:

1. An isolated chimeric Y-family polymerase comprising the amino acid sequence as set forth in
   SEQ ID NO: 57 (AiLFSte (AiDpo4/SteDpo4LF)) or a sequence having at least 95% sequence identity to SEQ ID NO: 57
wherein the chimeric Y-family polymerase has polymerase activity.

2. The polymerase of claim 1, comprising the amino acid sequence as set forth in SEQ ID NO: 57.

3. The polymerase of claim 1, comprising an amino acid sequence having at least 95% sequence identity to SEQ ID NO: 57.

4. A method of using a chimeric Y-family polymerase to add a nucleotide to a polynucleotide, the method comprising incubating a polynucleotide and a nucleotide with a chimeric Y-family polymerase, thereby adding the nucleotide to the polynucleotide, wherein the chimeric Y-family polymerase comprises SEQ ID NO: 57 (AiLFSte (AiDpo4/SteDpo4LF)).

5. A method of amplifying a DNA molecule, the method comprising:
   thermocycling the DNA molecule with a first primer, a second primer and an amount of the chimeric Y-family polymerase of claim 1 sufficient to amplify the DNA molecule, wherein the first primer hybridizes with a DNA sequence at the 3'-end of the DNA molecule, and the second primer hybridizes with a DNA sequence at the 5'-end of the DNA molecule, thereby amplifying the DNA molecule.

6. The method of claim 5, wherein the DNA is ancient or damaged DNA.

7. The method of claim 5, wherein amplifying the DNA molecule comprises incorporating fluorescent or modified nucleotides.

8. The method of claim 5, wherein the method further comprises thermocycling the DNA molecule with an amount of a high-fidelity polymerase sufficient to amplify the DNA molecule.

* * * * *

UNITED STATES PATENT AND TRADEMARK OFFICE
CERTIFICATE OF CORRECTION

| | | |
|---|---|---|
| PATENT NO. | : 7,745,188 B2 | Page 1 of 1 |
| APPLICATION NO. | : 11/596783 | |
| DATED | : June 29, 2010 | |
| INVENTOR(S) | : Woodgate et al. | |

It is certified that error appears in the above-identified patent and that said Letters Patent is hereby corrected as shown below:

In column 11, line 10, "comprises nucleic" should be --comprises a nucleic--.

In column 22, lines 4-5, "PCR For" should be --PCR. For--.

In column 25, lines 31-32, "junction of the of the LF" should be --junction of the LF--.

In column 35, line 31, "gradient The" should be --gradient. The--.

Signed and Sealed this
Fourth Day of January, 2011

David J. Kappos
*Director of the United States Patent and Trademark Office*